United States Patent
McChesney et al.

(10) Patent No.: US 11,643,424 B2
(45) Date of Patent: *May 9, 2023

(54) CARDIOPATHY-REDUCING PHOSPHODIESTER LIPIDS

(71) Applicant: Signpath Pharma, Inc., Sandy, UT (US)

(72) Inventors: James McChesney, Etta, MS (US); Annie Bouchard, Stoke (CA); Saravanan Kappusamy, Bangalore (IN); John Kallikat Augustine, Bangalore (IN); Daniel Emil Levy, San Mateo, CA (US)

(73) Assignee: SignPath Pharma, Inc., Sandy, UT (US)

( * ) Notice: Subject to any disclaimer, the term of this patent is extended or adjusted under 35 U.S.C. 154(b) by 61 days.

This patent is subject to a terminal disclaimer.

(21) Appl. No.: 17/191,214

(22) Filed: Mar. 3, 2021

(65) Prior Publication Data

US 2021/0198294 A1    Jul. 1, 2021

Related U.S. Application Data

(63) Continuation of application No. 16/452,858, filed on Jun. 26, 2019, now Pat. No. 10,975,111.

(60) Provisional application No. 62/690,196, filed on Jun. 26, 2018.

(51) Int. Cl.
*A61K 45/06* (2006.01)
*C07F 9/09* (2006.01)
*A61P 9/00* (2006.01)
*C07F 9/655* (2006.01)

(52) U.S. Cl.
CPC .................. *C07F 9/09* (2013.01); *A61P 9/00* (2018.01); *C07F 9/65515* (2013.01); *A61K 45/06* (2013.01)

(58) Field of Classification Search
CPC ....................................................... A61K 45/06
See application file for complete search history.

(56) References Cited

U.S. PATENT DOCUMENTS

| | | | |
|---|---|---|---|
| 10,975,111 | B2 | 4/2021 | Mchesney et al. |
| 2008/0300418 | A1 | 4/2008 | Ahmad et al. |
| 2015/0343063 | A1 | 12/2015 | Helson et al. |
| 2017/0095489 | A1 | 4/2017 | Helson |

FOREIGN PATENT DOCUMENTS

| | | |
|---|---|---|
| CN | 105273001 A | 1/2016 |
| CN | 106188169 | 7/2016 |
| EP | 3648772 A1 | 5/2020 |
| WO | 2005049587 | 6/2005 |
| WO | 2015095576 A1 | 6/2015 |
| WO | 2015187883 A1 | 10/2015 |
| WO | 2019010352 | 1/2019 |

OTHER PUBLICATIONS

Extended European Search Report for 19826650.4 dated Mar. 31, 2022, 9 pp.
Bersch, B., et al., "Total synthesis of perdeuterated phospholipids," Bulletin de la Societe Chimique de France, 1993, vol. 130, No. 4, pp. 575-583.
Bossi, L., et al., "The Substrate Requirements of Phospholipase D," Journal of Molecular Catalysis B: Enzymatic, 2001, vol. 11, No. 4-6, pp. 433-438.
Gagnon, Marie-Claude, et al., "A Flexible Synthetic Approach to Phosphatidylglycerols," European Journal of Organic Chemistry, 2017, No. 43, pp. 6401-6407.
Registry(STN)[online], Dec. 22, 2004, Date of Search, Mar. 3, 2022, CAS registration No. 801161-44-4.
Registry(STN)[online], Oct. 15, 2015, Date of Search, Mar. 3, 2022, CAS registration No. 1810042-18-2.
Registry(STN)[online], Oct. 15, 2015, Date of Search, Mar. 3, 2022, CAS registration No. 1810042-20-6.
Sato, rina, et al., "Simple Synthesis of Diastereomerically Pure Phosphatidylglycerols by Phospholipase D-catalized transphosphatidylation," Lipids, 2004, vol. 39, No. 10, pp. 1025-1030.
Taniguchi, Tohru et al., "Stereochemical Analysis of Glycerophospholipids by Vibrational Circular Dichroism," Journal of the American Chemical Society, 2015, vol. 137, No. 38, pp. 12191-12194.
Bouwer N., et al. "Cardiac monitoring in HER2-positive patients on trastuzumab treatment: A review and implications for clinical practice," The Breast, Apr. 16, 2020, 52, 33-44.
Cardinale, D., et al., "Anthracycline-Induced Cardiomyopathy," Journal of the American College of Cardiology, Jan. 19, 2010, 55(3), 213-220.

(Continued)

*Primary Examiner* — David K O'Dell

(74) *Attorney, Agent, or Firm* — Edwin S. Flores; Chalker Flores, LLP

(57) ABSTRACT

The present invention includes compound having the following structural formula:

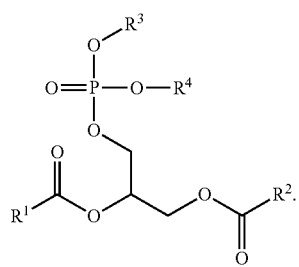

14 Claims, 8 Drawing Sheets

(56) References Cited

OTHER PUBLICATIONS

Keefe, D., "Anthracycline-induced cardiomyopathy," Seminars in Oncology, Aug. 2001, vol. 28, No. 4(12), 2-7.
Lee, K.J., et al., "Cytoprotective Effect of Vitamin D on Doxorubicin-Induced Cardiac Toxicity in Triple Negative Breast Cancer," International Journal of Molecular Sciences, Jul. 12, 2021, 22(14), 7439-7456.
Romond, E., et al., "Trastuzumab plus adjuvant chemotherapy for operable HER2-positive breast cancer," New England Journal of Medicine, Oct. 20, 2005, 353, 1673-1684.
Sordillo, P., et al., "The Prolonged QT Interval: Role of Pro-inflammatory Cytokines, Reactive Oxygen Species and the Ceramide and Sphingosine-1 Phosphate Pathways," In vivo, Sep. 25, 2015, 29(6), 619-636.
Allen, et al., "Pure Phosphatides and the Serodiagnosis of Syphilis," Bull. Worid Health Org., 1958, vol. 19, pp. 547-561.
Bonsen, P.P.M., et al., "The Synthesis of 3-Phosphatidyl-1'-Glycerol," Chem. Phys. Lipids 1, 1966, pp. 33-40.
International Search Report and Written Opinion by the Australian Patent Office for PCT/US2019/039162 dated Oct. 28, 2019, 11 pp.
Pubchem, Substance Record for SID 273112723, Available Dec. 17, 2015 [retrieved on Aug. 6, 2019], https://pubchem.ncbi.nlm.nih.gov/substance/273112723.

CARDIOPATHY-REDUCING PHOSPHODIESTER LIPIDS

CROSS-REFERENCE TO RELATED APPLICATIONS

This application is a continuation of U.S. patent application Ser. No. 16/452,858 filed on Jun. 26, 2019, now U.S. Pat. No. 10,975,111 issued on Apr. 13, 2021, which claims priority to U.S. Provisional Patent Application Ser. No. 62/690,196 filed Jun. 26, 2018, the contents of which is incorporated by reference herein in its entirety.

STATEMENT OF FEDERALLY FUNDED RESEARCH

None.

TECHNICAL FIELD OF THE INVENTION

The present invention relates in general to the field of novel lipids to reduce or eliminate cardiopathies, such as QT prolongation, cardiac muscle damage, or AV block, that are drug-induced or caused by a disease or condition.

BACKGROUND OF THE INVENTION

Without limiting the scope of the invention, its background is described in connection with drug-induced QT prolongation and other cardiopathies and cardio-toxicities.

There are numerous pharmaceutical agents designed for the treatment of various diseases which are commonly prescribed, despite being known or suspecting of having adverse effects on the patient's heart. In addition to cardiac arrhythmias, including QT prolongation, supraventricular tachycardias (SVT), and atrial fibrillation (AF), a number of other cardiac toxicities can occur, including cardiac muscle damage, cardiomyopathy, congestive heart failure, and left ventricular hypertrophy (LVH) as a side effect of pharmaceutical agents.

The cardiotoxicity of those pharmaceutical agents can lead to significant complications that can affect patients being treated for various diseases, such as proliferative malignancies. The severity of such toxicity depends on many factors such as the immediate and cumulative dose, the method of administration, the presence of any underlying cardiac condition, and various congenital or acquired cardiac risk factors unique to a particular patient. Moreover, toxicity can be affected by current or previous treatment with other pharmaceutical agents. Cardiotoxic effects can occur immediately during administration of the drug, or they may not manifest themselves until months or years after the patient has been treated.

High-dose chemotherapy remains the therapy of choice for aggressive malignancies. Countless clinical studies have demonstrated that high-dose chemotherapy can significantly prolong patient survival; however, its use and effectiveness are limited by significant side effects, in particular cardiotoxicity. In mid-to-late phase cardiac toxicity, heart failure can appear many years after chemotherapy has ended. Treatment with chemotherapeutic agents is known to result in pericardial and endomyocardial fibrosis, heart failure, myocarditis, or pericarditis. Chemotherapy has also been associated with hemorrhagic myocardial necrosis and cardiomyopathy.

In addition, antineoplastic monoclonal antibodies are also linked to cardiotoxicity. Infusion-related cardiotoxic effects, such as left ventricular dysfunction, congestive heart failure, and other cardiac dysfunction can occur. The risk of such complications increases if the patient has preexisting cardiac disease, older age, prior cardiotoxic therapy, or radiation to the chest.

Tyrosine Kinase inhibitors (TKIs) have well known cardiotoxic effects. The antracyclins, trastuzumab, imatinib mesylate, dasatinib, nilotinib, sunitinib, sorafenib vandetanib, and lapatinib have all been associated with a range of mechanical and electrical dysfunctions.

Among the toxic effects associated with TKIs are QT prolongation, sudden cardiac death (both considered rhythmic dysfunctions), as well as contractility issues such as reduction in left ventricular ejection fraction (LVEF), congestive heart failure (CHF), acute coronary disease, hypertension, and myocardial infarction (MI). Given the therapeutic potential of drugs such as the tyrosine kinase inhibitors, various strategies have been used to attempt to mitigate the cardiotoxicity of cancer treatment. The primary method for preventing cardiac toxicity is to limit the dose of cardiotoxic drugs. There is also some evidence that the method of drug administration may affect the risk of cardiac toxicity. Rapid administration of cardio toxic agents results in high blood levels, which may cause more heart damage than the same amount of drug given over a longer period of time. Giving smaller doses of drug more frequently can also decrease the toxicity compared to large doses of drugs at longer intervals.

The risk of cardiac toxicity from certain chemotherapy agents has been reduced by encapsulating these drugs in a liposome. For example, studies indicate that cardiotoxicity is considerably lower with liposomal doxorubicin formulations than with conventional doxorubicin.

Dexrazoxane is an aminopolycarboxylic acid that has been shown to prevent or reduce the severity of heart damage caused by doxorubicin. Dexrazoxane is thought to protect the heart muscle by blocking the formation of oxygen free radicals. One of the ways that radiation and chemotherapy drugs damage cells is by forming free radicals. Free radicals are unstable molecules that are formed during many normal cellular processes that involve oxygen, such as burning fuel for energy. They are also formed from exposure to elements in the environment, like tobacco smoke, radiation and chemotherapy drugs.

However, a need remains for new composition and methods for reducing cardiopathies, whether drug-induced, or as a result of a disease or condition.

SUMMARY OF THE INVENTION

The present invention relates to novel cardiopathy-reducing lipids of Formula I:

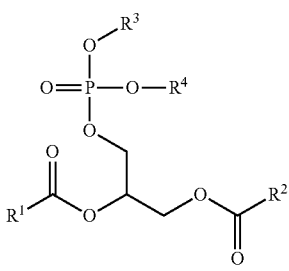

wherein, $R^1$ is a $C_1$-$C_{20}$ branched or unbranched hydrocarbon possessing 0-10 double bonds, 0-10 triple bonds or a combination of 0-10 double and triple bonds;

$R^2$ is a $C_1$-$C_{20}$ branched or unbranched hydrocarbon possessing 0-10 double bonds, 0-10 triple bonds or a combination of 0-10 double and triple bonds;

$R^3$ is

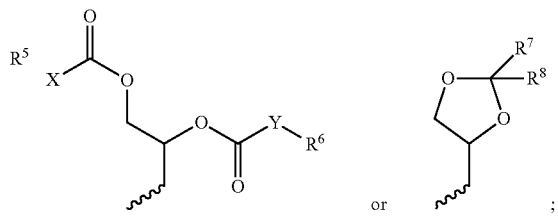

or ;

$R^4$ is H or a pharmaceutically acceptable cation, wherein incorporation of said pharmaceutically acceptable cation results in a salt, e.g., a monomeric salt, a dimeric salt, a trimeric salt, or a multimeric salt;

$R^5$ is a $C_1$-$C_{10}$ branched or unbranched hydrocarbon optionally substituted with one or more groups selected from OH, OAc, OMe, $NH_2$, NHAc, NHMe, $N(Me)_2$, SH, CN, COOH, $CONH_2$, Cl, Br and I;

$R^6$ is a $C_1$-$C_{10}$ branched or unbranched hydrocarbon optionally substituted with one or more groups selected from OH, OAc, OMe, $NH_2$, NHAc, NHMe, $N(Me)_2$, SH, CN, COOH, $CONH_2$, Cl, Br and I;

$R^7$ is a $C_0$-$C_{20}$ branched or unbranched hydrocarbon possessing 0-10 double bonds, 0-10 triple bonds or a combination of 0-10 double and triple bonds;

$R^8$ is H or a $C_0$-$C_{20}$ branched or unbranched hydrocarbon possessing 0-10 double bonds, 0-10 triple bonds or a combination of 0-10 double and triple bonds;

X is a direct linkage, $CH_2$, O or NH;

Y is a direct linkage, $CH_2$, O or NH; and,

Each stereogenic center is independently R, S or racemic.

Another embodiment of this invention relates to a method of preparing a compound of Formula I

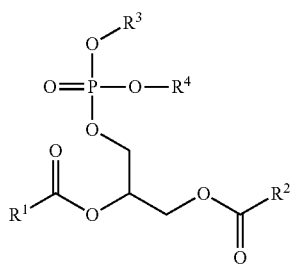

I wherein, $R^1$ is a $C_1$-$C_{20}$ branched or unbranched hydrocarbon possessing 0-10 double bonds, 0-10 triple bonds or a combination of 0-10 double and triple bonds;

$R^2$ is a $C_1$-$C_{20}$ branched or unbranched hydrocarbon possessing 0-10 double bonds, 0-10 triple bonds or a combination of 0-10 double and triple bonds;

$R^3$ is

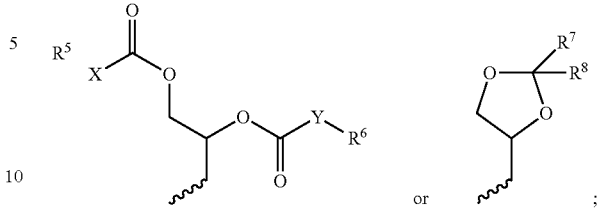

or ;

$R^4$ is H or a pharmaceutically acceptable cation, wherein incorporation of said pharmaceutically acceptable cation results in a salt, e.g., a monomeric salt, a dimeric salt, a trimeric salt, or a multimeric salt;

$R^5$ is a $C_1$-$C_{10}$ branched or unbranched hydrocarbon optionally substituted with one or more groups selected from OH, OAc, OMe, $NH_2$, NHAc, NHMe, $N(Me)_2$, SH, CN, COOH, $CONH_2$, Cl, Br and I;

$R^6$ is a $C_1$-$C_{10}$ branched or unbranched hydrocarbon optionally substituted with one or more groups selected from OH, OAc, OMe, $NH_2$, NHAc, NHMe, $N(Me)_2$, SH, CN, COOH, $CONH_2$, Cl, Br and I;

$R^7$ is a $C_0$-$C_{20}$ branched or unbranched hydrocarbon possessing 0-10 double bonds, 0-10 triple bonds or a combination of 0-10 double and triple bonds;

$R^8$ is H or a $C_0$-$C_{20}$ branched or unbranched hydrocarbon possessing 0-10 double bonds, 0-10 triple bonds or a combination of 0-10 double and triple bonds;

X is a direct linkage, $CH_2$, O or NH;

Y is a direct linkage, $CH_2$, O or NH; and,

Each stereogenic center is independently R, S or racemic;

Comprising the steps of:

(1) Converting the hydroxyl groups of a compound of Formula II to esters, carbonates, carbamates, or collectively to an acetal or a ketal

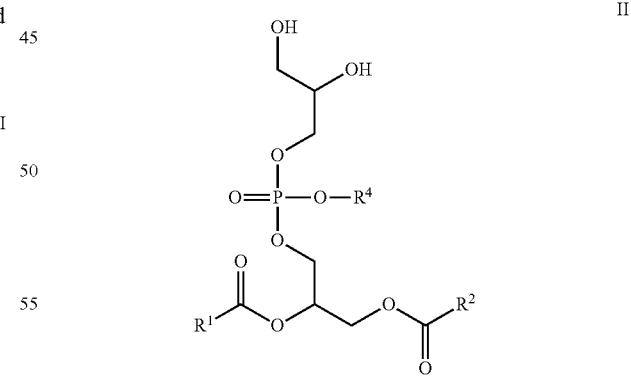

II wherein, all substitutions are defined as above; and (2) Converting a phosphorus-bound OH group to O—$R^4$, wherein $R^4$ is not H; or Comprising the steps of:

(1) Linking a compound of Formula III with a compound of Formula IV or with a compound of Formula V through creation of a phosphate diester bridge

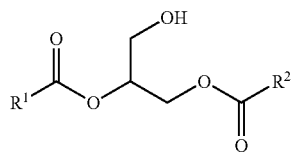

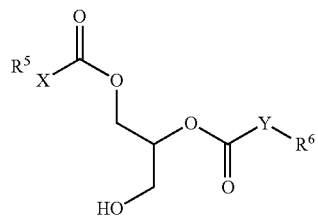

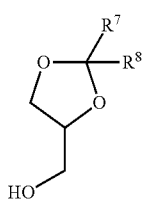

wherein, all substitutions are defined as above; and (2) Converting a phosphorus-bound OH group to O—$R^4$, wherein $R^4$ is not H.

In one aspect, $R^4$ is H, Li, Na, K, Mg, Ca, Zn, Cs, ammonium or tetraalkylammonium. In another aspect, the compound is selected from the compound is selected from compounds 1 to 30.

Another embodiment of this invention relates to pharmaceutical compositions comprising a compound of Formula I and a pharmaceutically acceptable diluent or carrier. The pharmaceutical compositions may also comprise one or more agents that induce a cardiopathy as a side effect, wherein the compound reduces or eliminates the cardiopathy. Furthermore, said pharmaceutical compositions may also comprise one or more excipients, binders, anti-adherents, coatings, disintegrants, fillers, flavors, dyes, colors, glidants, lubricants, preservatives, sorbents, sweeteners, derivatives thereof, or combinations thereof. In one aspect, $R^4$ is H, Li, Na, K, Mg, Ca, Zn, Cs, ammonium or tetraalkylammonium. In one aspect, compound is selected from at least one of:

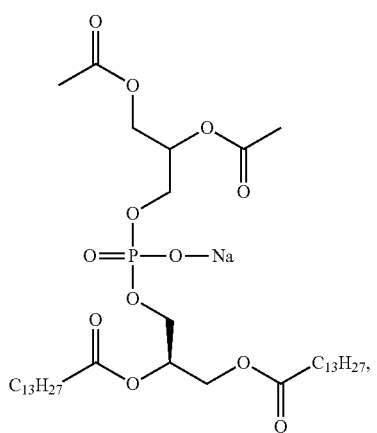

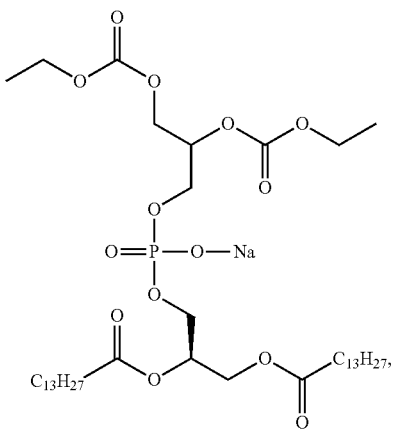

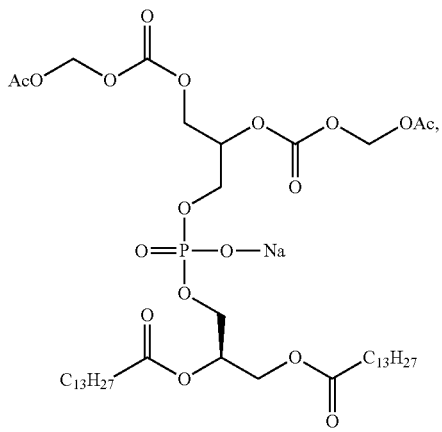

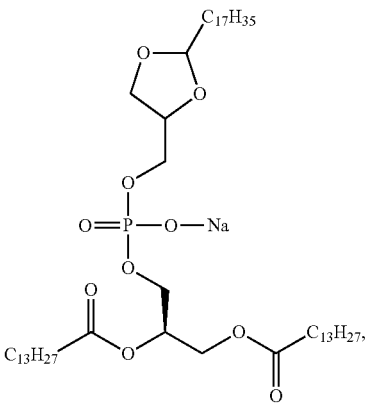

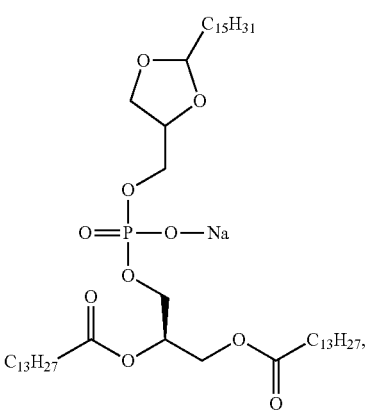

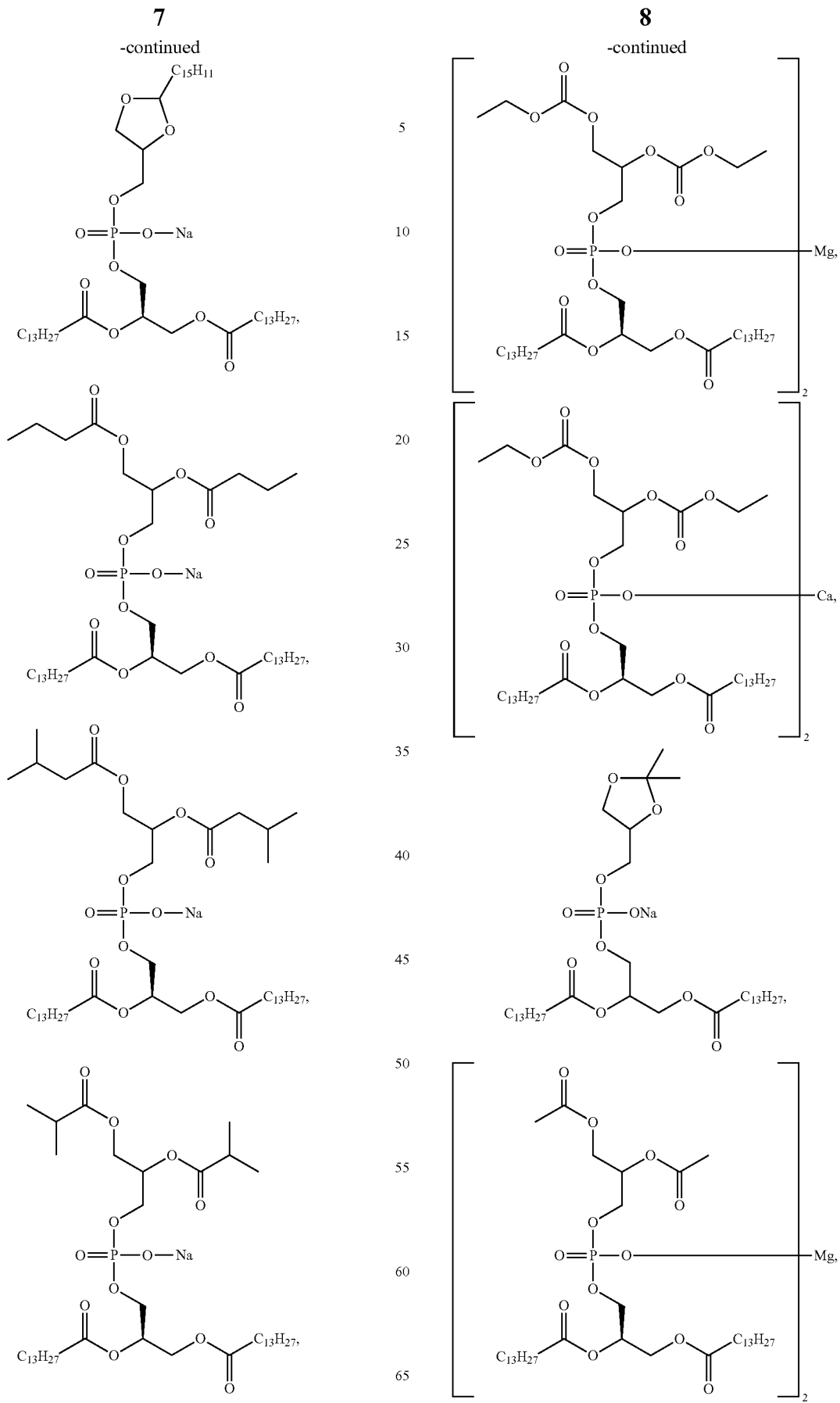

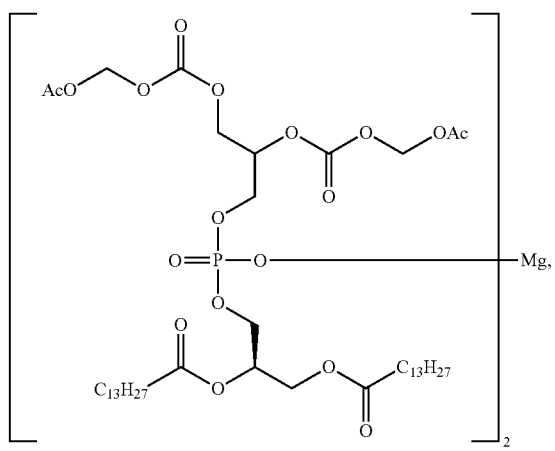
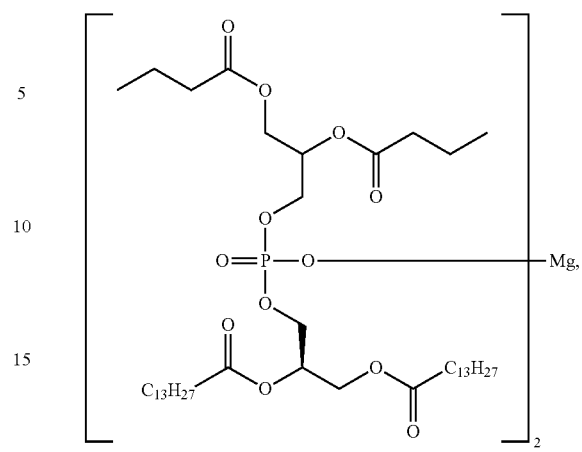
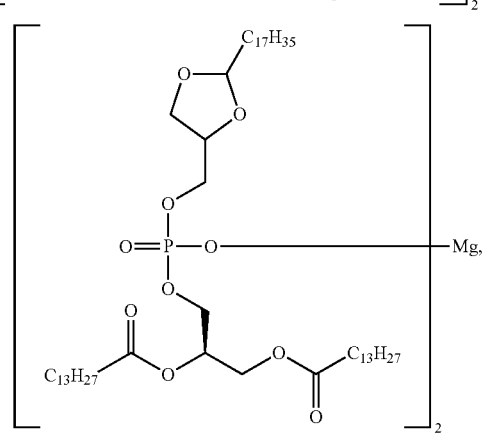
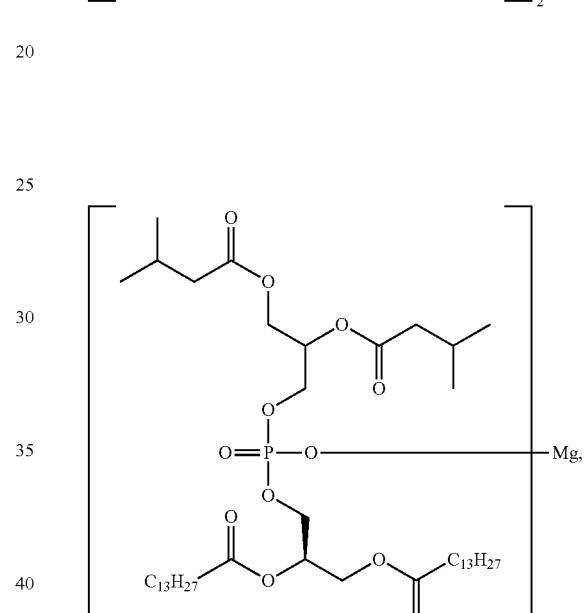
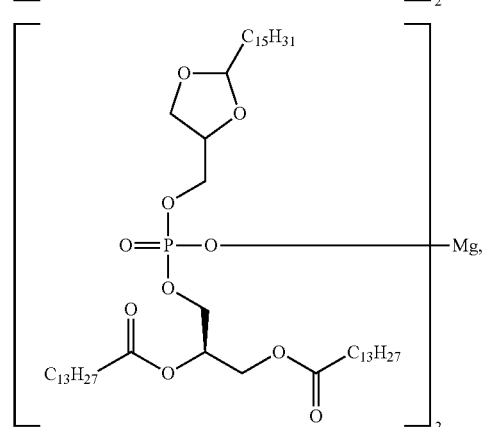
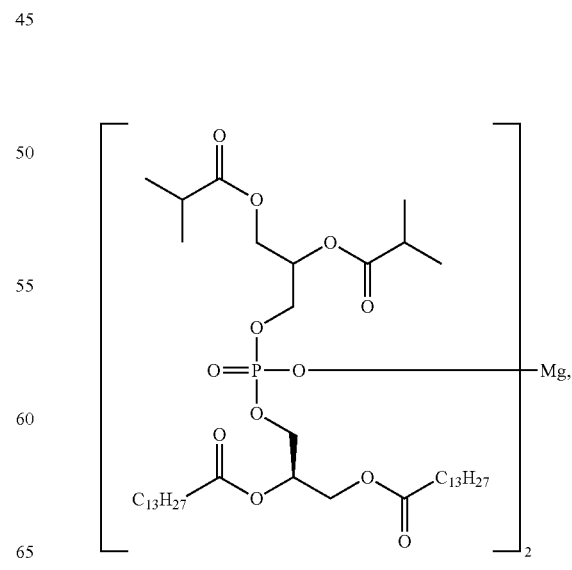
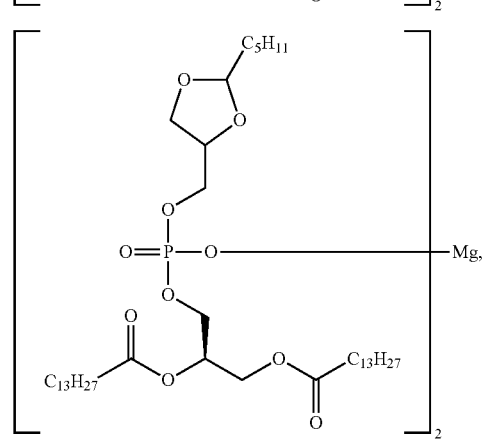

-continued
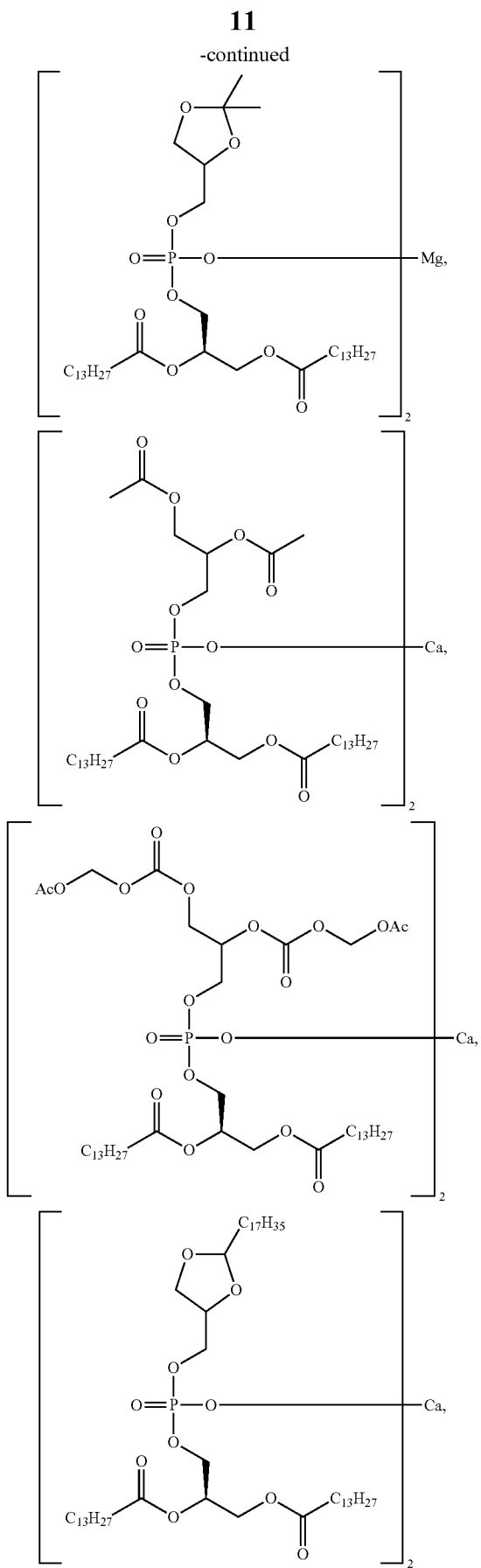
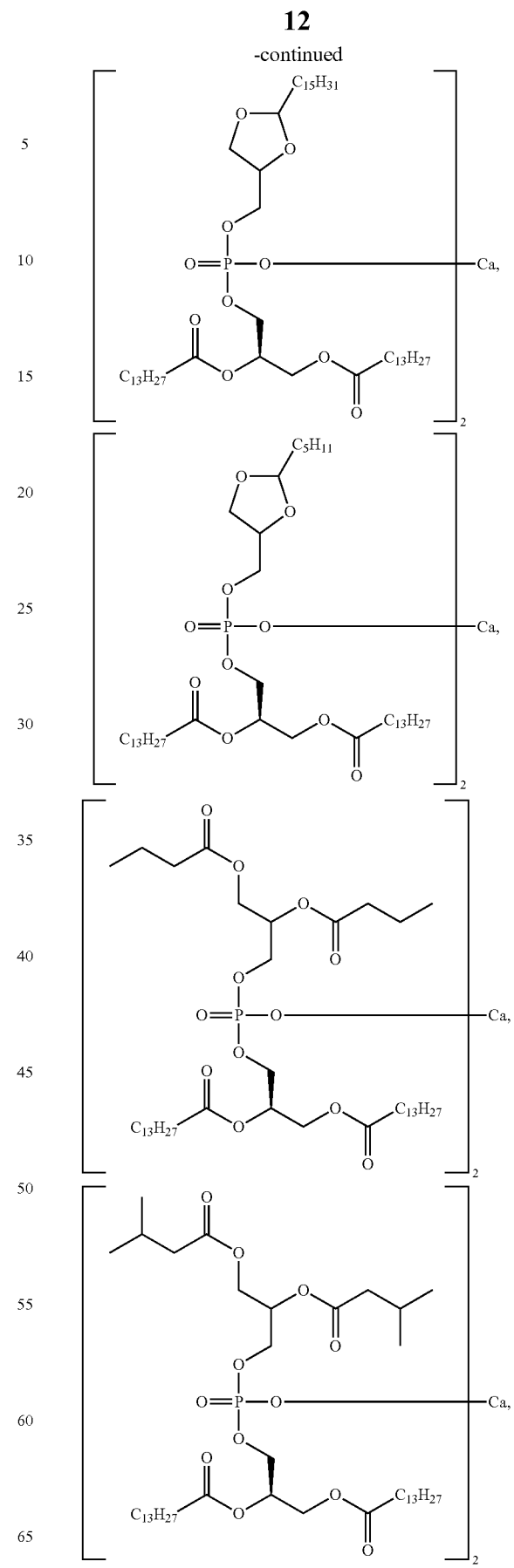

-continued

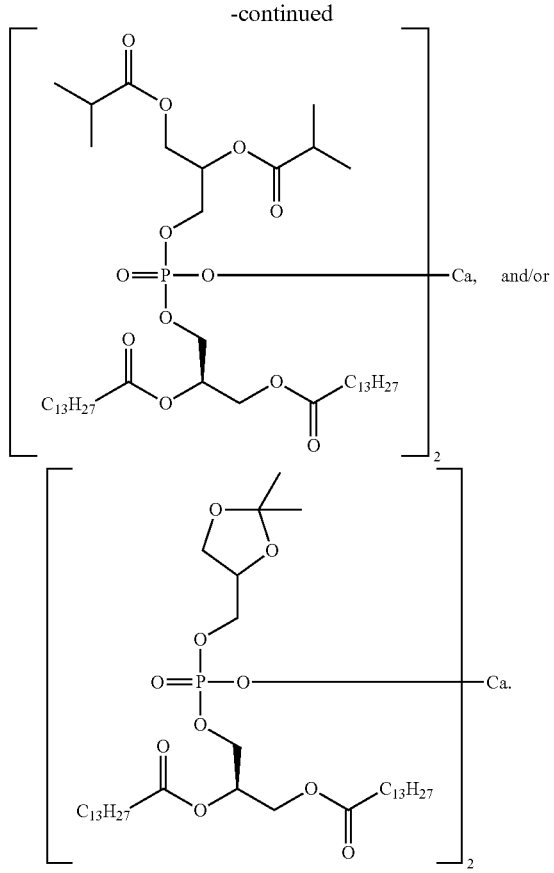

In another aspect, the compounds exist as a single entity, a solvate, a hydrate, a crystal, an amorphous solid, a liquid, or an oil. In another aspect, the composition is in a pharmaceutical composition, which may further comprise one or more agents that induce a cardiopathy as a side effect. In another aspect, the agent that induces a cardiopathy as a side effect is selected from at least one of: Albuterol, Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Cocaine, Curcumin, Crizotinib, Dabrafenib, Dasatinib, Desipramine, Dexmedetomidine, Dexmethylphenidate, Dextroamphetamine, Amphetamine, Dihydroartemisinin and Piperaquine, Diphenhydramine, Disopyramide, Dobutamine, Dofetilide, Dolasetron, Domperidone, Dopamine, Doxepin, Dronedarone, Droperidol, Ephedrine, Epinephrine, Adrenaline, Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide, Frusemide, Galantamine, Gatifloxacin, Gemifloxacin, Granisetron, Halofantrine, Haloperidol, Hydrochlorothiazide, Ibutilide, Iloperidone, Imipramine, Melipramine, Indapamide, Isoproterenol, Isradipine, Itraconazole, Ivabradine, Ketoconazole, Lapatinib, Levalbuterol, Levofloxacin, Levomethadyl, Lisdexamfetamine, Lithium, Mesoridazine, Metaproterenol, Methadone, Methamphetamine, Methylphenidate, Midodrine, Mifepristone, Mirabegron, Mirtazapine, Moexipril/HCTZ, Moxifloxacin, Nelfinavir, Nicardipine, Nilotinib, Norepinephrine, Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salbutamol, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone. In another aspect, the pharmaceutical composition further comprises one or more excipients, binders, anti-adherents, coatings, disintegrants, fillers, flavors, dyes, colors, glidants, lubricants, preservatives, sorbents, sweeteners, derivatives thereof, or combinations thereof. In another aspect, the binder is selected from the group consisting of hydroxypropylmethylcellulose, ethyl cellulose, povidone, acrylic and methacrylic acid co-polymers, pharmaceutical glaze, gums, and milk derivatives. In another aspect, the pharmaceutical composition comprises a compound of Formula I in an amount per unit dose of between about 1 mg and about 1 gram per unit dose. In another aspect, the pharmaceutical composition is a formulation for oral, sublingual, transdermal, suppository, intrathecal, enteral, parenteral, intravenous, intraperitoneal, cutaneous, subcutaneous, topical, pulmonary, rectal, vaginal, or intramuscular administration. In another aspect, the formulation for oral administration is a tablet, capsule, caplet, pill, powder, troche, lozenge, slurry, liquid solution, suspension, emulsion, elixir or oral thin film (OTF). In another aspect, the formulation is a solid form, a solution, a suspension, or a soft gel form. The pharmaceutical dosage forms may be selected from oral, sublingual, transdermal, suppository, intrathecal, enteral, parenteral, intravenous, intraperitoneal, cutaneous, subcutaneous, topical, pulmonary, rectal, vaginal, or intramuscular administration.

Another embodiment of this invention provides a method of reducing or eliminating one or more of a cardiac channelopathy, cardiac muscle damage, or a condition resulting from the irregularity or alteration in the cardiac pattern, in a human or animal subject, comprising the step of administering to a human or animal subject a compound of Formula I, or any one of compounds 1-30, wherein the compound reduces or eliminates the one or more of a cardiac channelopathy or a condition resulting from the irregularity or alteration in the cardiac pattern caused by the active agent used to treat a disease. The composition can be formulated with a compounds that causes a channelopathy, cardiac muscle damage, or a condition resulting from the irregularity or alteration in the cardiac pattern, in a human or animal subject, as set forth herein.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
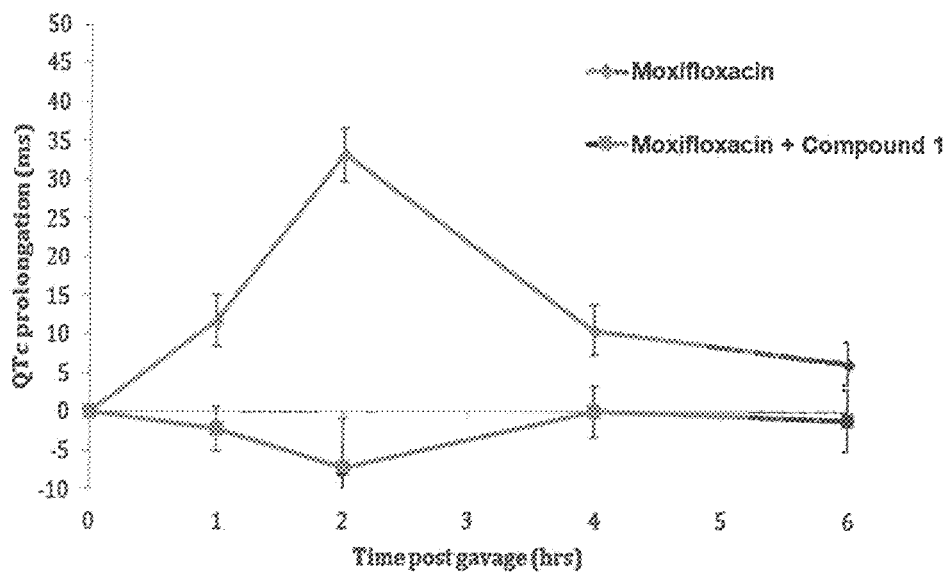
FIG. 1 is a graph that shows the effect of an oral single dose of Moxifloxacin (20 mg/kg) on QTc interval of guinea pigs compared to the same oral single dose of Moxifloxacin administrated concomitantly with an oral single dose of Compound 1.

1. General Description of the Compounds in at Least Some Embodiments of the Invention At least one embodiment of the present invention provides a structure of Formula I:

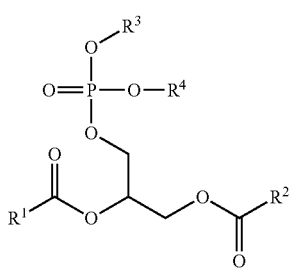

I wherein, $R^1$ is a $C_1$-$C_{20}$ branched or unbranched hydrocarbon possessing 0-10 double bonds, 0-10 triple bonds or a combination of 0-10 double and triple bonds;

$R^2$ is a $C_1$-$C_{20}$ branched or unbranched hydrocarbon possessing 0-10 double bonds, 0-10 triple bonds or a combination of 0-10 double and triple bonds;

$R^3$ is

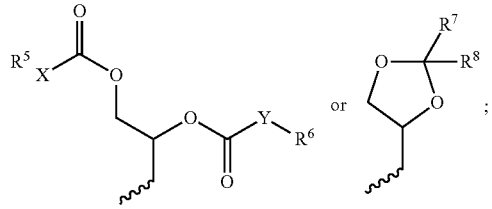

$R^4$ is H or a pharmaceutically acceptable cation, wherein incorporation of said pharmaceutically acceptable cation results in a salt, e.g., a monomeric salt, a dimeric salt, a trimeric salt, or a multimeric salt;

$R^5$ is a $C_1$-$C_{10}$ branched or unbranched hydrocarbon optionally substituted with one or more groups selected from OH, OAc, OMe, $NH_2$, NHAc, NHMe, $N(Me)_2$, SH, CN, COOH, $CONH_2$, Cl, Br and I;

$R^6$ is a $C_1$-$C_{10}$ branched or unbranched hydrocarbon optionally substituted with one or more groups selected from OH, OAc, OMe, $NH_2$, NHAc, NHMe, $N(Me)_2$, SH, CN, COOH, $CONH_2$, Cl, Br and I;

$R^7$ is a $C_0$-$C_{20}$ branched or unbranched hydrocarbon possessing 0-10 double bonds, 0-10 triple bonds or a combination of 0-10 double and triple bonds;

$R^8$ is H or a $C_0$-$C_{20}$ branched or unbranched hydrocarbon possessing 0-10 double bonds, 0-10 triple bonds or a combination of 0-10 double and triple bonds;

X is a direct linkage, $CH_2$, O or NH;

Y is a direct linkage, $CH_2$, O or NH; and,

Each stereogenic center is independently R, S or racemic.

2. Compounds and Definitions

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

Compounds of the present invention include those described generally above, and are further illustrated by the classes, subclasses, and species disclosed herein. As used herein, the following definitions shall apply unless otherwise indicated. In at least some embodiments, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

To facilitate the understanding of this invention, a number of terms are defined below. Terms defined herein have meanings as commonly understood by a person of ordinary skill in the areas relevant to the present invention.

Terms such as "a" "an" and "the" are not intended to refer to only a singular entity, but include the general class of which a specific example may be used for illustration. The terminology herein is used to describe specific embodiments of the invention, but their usage does not limit the invention, except as outlined in the claims. Specifically, the use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only. As used herein, each of the compounds may be used in a formulation or method that comprises one or more components or steps, but may also be in a composition or method that consists essentially of the listed components, or even in a composition or method that consists of the listed components.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least 1, 2, 3, 4, 5, 6, 7, 10, 12 or 15%.

An "alkyl" group refers, in one embodiment, to a saturated aliphatic hydrocarbon, including straight-chain, branched-chain and cyclic alkyl groups. In one embodiment, the alkyl group has 1-20 carbons. In another embodiment, the alkyl group has 1-15 carbons. In another embodiment, the alkyl group has 1-10 carbons. In another embodiment, the alkyl group has 11-20 carbons. In another embodiment, the alkyl group has 5-15 carbons. In yet still another embodiment, the alkyl group has 1-5 carbons. The alkyl group may be unsubstituted or substituted by one or more groups selected from halogen, hydroxy, alkoxy, carboxylic acid, aldehyde, carbonyl, amido, cyano, alkylamido, dialkylamido, nitro, amino, alkylamino, dialkylamino, carboxyl, thio and thioalkyl.

An "alkenyl" group refers, in one embodiment, to an unsaturated hydrocarbon, including straight chain, branched chain and cyclic groups having one or more double bonds. The alkenyl group may have one double bond, two double bonds, three double bonds, etc. In another embodiment, the alkenyl group has 2-20 carbons. In another embodiment, the alkenyl group has 11-20 carbons. In another embodiment, the alkenyl group has 5-15 carbons. In another embodiment, the alkenyl group has 2-5 carbons. In another embodiment, the alkenyl group has 2-10 carbons. In another embodiment the alkenyl group is ethenyl (—CH═CH2) Examples of alkenyl groups that may be included are ethenyl, propenyl, butenyl, cyclohexenyl, etc. The alkenyl group may be unsubstituted or substituted by a halogen, hydroxy, alkoxy carbonyl, amido, alkylamido, dialkylamido, nitro, cyano, amino, alkylamino, dialkylamino, carboxyl, thio and/or thioalkyl.

An "alkynyl" group refers, in one embodiment, to an unsaturated hydrocarbon, including straight chain, branched chain and cyclic groups having one or more triple bonds. The alkynyl group may have one triple bond, two triple bonds, three triple bonds, etc. In another embodiment, the alkynyl group has 2-20 carbons. In another embodiment, the alkynyl group has 11-20 carbons. In another embodiment, the alkynyl group has 5-15 carbons. In another embodiment, the alkynyl group has 2-15 carbons. In another embodiment, the alkynyl group has 2-10 carbons. In another embodiment the alkynyl group is ethynyl. Examples of alkenyl groups are ethynyl, propynyl, butynyl, cyclohexynyl, etc. The alkynyl group may be unsubstituted or substituted by a halogen, hydroxy, alkoxy carbonyl, cyano, amido, alkylamido, dialkylamido, nitro, amino, alkylamino, dialkylamino, carboxyl, thio and/or thioalkyl.

In one embodiment, the term "halogen" refers, in one embodiment to F, in another embodiment to Cl, in another embodiment to Br, and in another embodiment to I.

A "pharmaceutically acceptable cation" refers in one embodiment to those organic cations or inorganic cations that are pharmaceutically acceptable for use in a mammal and are well known in the art. For example, inorganic cations or organic cations include but are not limited to lithium, sodium, potassium, magnesium, calcium, barium, zinc, aluminum, cesium, and amine cations. Amine cations include but are not limited to cations derived from ammonia, triethylamine, tromethamine (TRIS), triethanolamine, ethylenediamine, glucamine, N-methylglucamine, glycine, lysine, ornithine, arginine, ethanolamine, choline and the like. In one embodiment, the amine cations are cations wherein X+ is of the formula YH+ wherein Y is ammonia, triethylamine, trimethylamine (TRIS), triethanolamine, ethylenediamine, glucamine, N-methylglucamine, glycine, lysine, ornithine, arginine, ethanolamine, choline and the like. In one embodiment suitable cationic organic or inorganic salts that can be used include cationic moieties that can form an ionic association with the O moieties on the compound and not significantly adversely affecting the desired properties of the compound for purposes of the present invention, e.g., increased solubility, stability and the like. It will be appreciated by those skilled in the art that a compound of Formula I wherein $R^4$ is an organic cation or inorganic cation can be converted to a compound of formula I comprising one or more different organic or inorganic cation.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a 13C- or 14C-enriched carbon are within the scope of this invention. Such compounds are useful, for example, as analytical tools, as probes in biological assays, or as therapeutic agents in accordance with the present invention.

As used herein, the term "in vivo" refers to being inside the body. The term "in vitro" used as used in the present application is to be understood as indicating an operation carried out in a non-living system.

As used herein, the term "treatment" refers to the treatment of the conditions mentioned herein, particularly in a patient who demonstrates symptoms of the disease or disorder.

As used herein, the term "treatment" or "treating" refers to any administration of a compound of the present invention and includes (i) inhibiting the disease in an animal that is experiencing or displaying the pathology or symptomatology of the diseased (i.e., arresting further development of the pathology and/or symptomatology); or (ii) ameliorating the disease in an animal that is experiencing or displaying the pathology or symptomatology of the diseased (i.e., reversing the pathology and/or symptomatology). The term "controlling" includes preventing treating, eradicating, ameliorating or otherwise reducing the severity of the condition being controlled.

As used herein, the terms "effective amount" or "therapeutically effective amount" described herein means the amount of the subject compound that will elicit the biological or medical response of a tissue, system, animal or human that is being sought by the researcher, veterinarian, medical doctor or other clinician.

As used herein, the terms "administration of" or "administering a" compound as used herein should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

As used herein the term "intravenous administration" includes injection and other modes of intravenous administration.

As used herein, the term "pharmaceutically acceptable" as used herein to describe a carrier, diluent or excipient must be compatible with the other ingredients of the formulation and not deleterious to the recipient thereof.

3. Description of Exemplary Embodiments

In one embodiment, the present invention relates to a compound of Formula I:

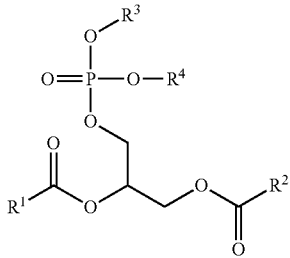

wherein, $R^1$ is a $C_1$-$C_{20}$ branched or unbranched hydrocarbon possessing 0-10 double bonds, 0-10 triple bonds or a combination of 0-10 double and triple bonds;

$R^2$ is a $C_1$-$C_{20}$ branched or unbranched hydrocarbon possessing 0-10 double bonds, 0-10 triple bonds or a combination of 0-10 double and triple bonds;

$R^3$ is

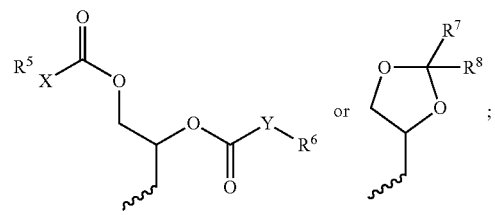

$R^4$ is H or a pharmaceutically acceptable cation, wherein incorporation of said pharmaceutically acceptable cation results in a salt, e.g., a monomeric salt, a dimeric salt, a trimeric salt, or a multimeric salt;

$R^5$ is a $C_1$-$C_{10}$ branched or unbranched hydrocarbon optionally substituted with one or more groups selected from OH, OAc, OMe, $NH_2$, NHAc, NHMe, $N(Me)_2$, SH, CN, COOH, $CONH_2$, Cl, Br and I;

$R^6$ is a $C_1$-$C_{10}$ branched or unbranched hydrocarbon optionally substituted with one or more groups selected from OH, OAc, OMe, $NH_2$, NHAc, NHMe, $N(Me)_2$, SH, CN, COOH, $CONH_2$, Cl, Br and I;

$R^7$ is a $C_0$-$C_{20}$ branched or unbranched hydrocarbon possessing 0-10 double bonds, 0-10 triple bonds or a combination of 0-10 double and triple bonds;

$R^8$ is H or a $C_0$-$C_{20}$ branched or unbranched hydrocarbon possessing 0-10 double bonds, 0-10 triple bonds or a combination of 0-10 double and triple bonds;

X is a direct linkage, $CH_2$, O or NH;

Y is a direct linkage, $CH_2$, O or NH; and,

Each stereogenic center is independently R, S or racemic.

In one embodiment, the present invention relates to a compound of Formula I:

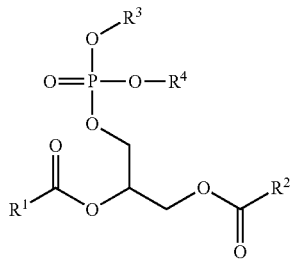

wherein, $R^1$ is a $C_1$-$C_{20}$ branched or unbranched hydrocarbon possessing 0-10 double bonds, 0-10 triple bonds or a combination of 0-10 double and triple bonds;

$R^2$ is a $C_1$-$C_{20}$ branched or unbranched hydrocarbon possessing 0-10 double bonds, 0-10 triple bonds or a combination of 0-10 double and triple bonds;

$R^3$ is

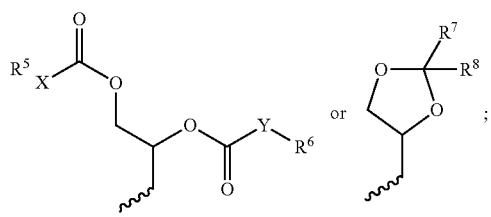

$R^4$ is H, Li, Na, K, Mg, Ca, Zn, Cs, ammonium or tetraalkylammonium, wherein Li, Na and K form monomeric salts and wherein Mg, Ca, Zn and Cs form a salt, e.g., a monomeric salt, a dimeric salt, a trimeric salt, or a multimeric salt;

$R^5$ is a $C_1$-$C_{10}$ branched or unbranched hydrocarbon optionally substituted with one or more groups selected from OH, OAc, OMe, $NH_2$, NHAc, NHMe, $N(Me)_2$, SH, CN, COOH, $CONH_2$, Cl, Br and I;

$R^6$ is a $C_1$-$C_{10}$ branched or unbranched hydrocarbon optionally substituted with one or more groups selected from OH, OAc, OMe, $NH_2$, NHAc, NHMe, $N(Me)_2$, SH, CN, COOH, $CONH_2$, Cl, Br and I;

$R^7$ is a $C_0$-$C_{20}$ branched or unbranched hydrocarbon possessing 0-10 double bonds, 0-10 triple bonds or a combination of 0-10 double and triple bonds;

$R^8$ is H or a $C_0$-$C_{20}$ branched or unbranched hydrocarbon possessing 0-10 double bonds, 0-10 triple bonds or a combination of 0-10 double and triple bonds;

X is a direct linkage, $CH_2$, O or NH;

Y is a direct linkage, $CH_2$, O or NH; and,

Each stereogenic center is independently R, S or racemic.

In one embodiment, the present invention relates to a method of preparing a compound of Formula I

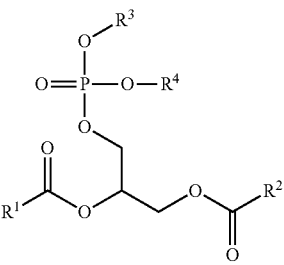

wherein, $R^1$ is a $C_1$-$C_{20}$ branched or unbranched hydrocarbon possessing 0-10 double bonds, 0-10 triple bonds or a combination of 0-10 double and triple bonds;

$R^2$ is a $C_1$-$C_{20}$ branched or unbranched hydrocarbon possessing 0-10 double bonds, 0-10 triple bonds or a combination of 0-10 double and triple bonds;

$R^3$ is

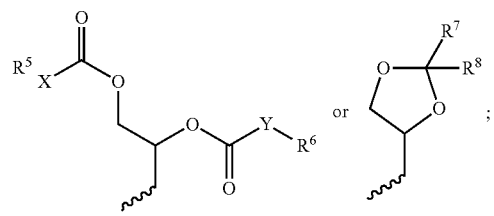

$R^4$ is H or a pharmaceutically acceptable cation, wherein incorporation of said pharmaceutically acceptable cation results in a salt, e.g., a monomeric salt, a dimeric salt, a trimeric salt, or a multimeric salt;

$R^5$ is a $C_1$-$C_{10}$ branched or unbranched hydrocarbon optionally substituted with one or more groups selected from OH, OAc, OMe, $NH_2$, NHAc, NHMe, $N(Me)_2$, SH, CN, COOH, $CONH_2$, Cl, Br and I;

$R^6$ is a $C_1$-$C_{10}$ branched or unbranched hydrocarbon optionally substituted with one or more groups selected from OH, OAc, OMe, $NH_2$, NHAc, NHMe, $N(Me)_2$, SH, CN, COOH, $CONH_2$, Cl, Br and I;

$R^7$ is a $C_0$-$C_{20}$ branched or unbranched hydrocarbon possessing 0-10 double bonds, 0-10 triple bonds or a combination of 0-10 double and triple bonds;

$R^8$ is H or a $C_0$-$C_{20}$ branched or unbranched hydrocarbon possessing 0-10 double bonds, 0-10 triple bonds or a combination of 0-10 double and triple bonds;

X is a direct linkage, $CH_2$, O or NH;

Y is a direct linkage, $CH_2$, O or NH; and,

Each stereogenic center is independently R, S or racemic;

Comprising the steps of:

(1) Converting the hydroxyl groups of a compound of Formula II to esters, carbonates, carbamates, or collectively to an acetal or a ketal

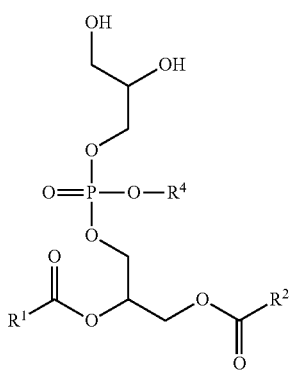

wherein, all substitutions are defined as above; and
(2) Converting a phosphorus-bound OH group to O—R$^4$, wherein R$^4$ is not H; or Comprising the steps of:
(1) Linking a compound of Formula III with a compound of Formula IV or with a compound of Formula V through creation of a phosphate diester bridge

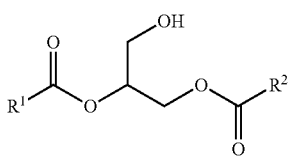

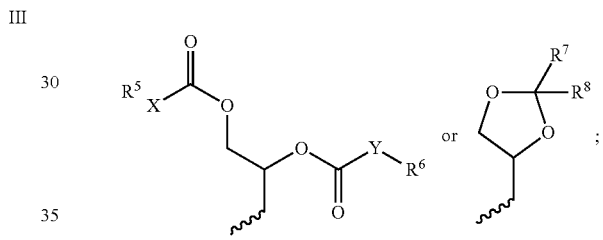

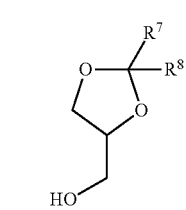

wherein, all substitutions are defined as above; and
(2) Converting a phosphorus-bound OH group to O—R$^4$, wherein R$^4$ is not H.

In a preferred embodiment, the present invention relates to a method of preparing a compound of Formula I

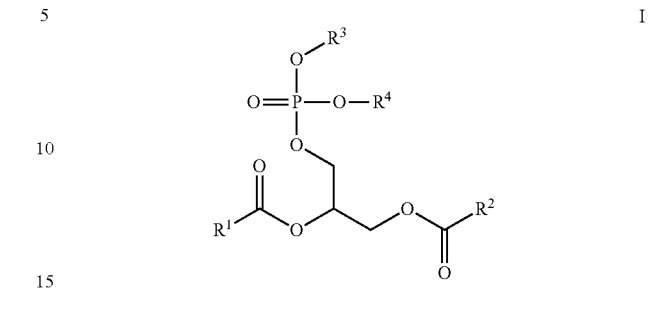

wherein,

R$^1$ is a C$_1$-C$_{20}$ branched or unbranched hydrocarbon possessing 0-10 double bonds, 0-10 triple bonds or a combination of 0-10 double and triple bonds;

R$^2$ is a C$_1$-C$_{20}$ branched or unbranched hydrocarbon possessing 0-10 double bonds, 0-10 triple bonds or a combination of 0-10 double and triple bonds;

R$^3$ is

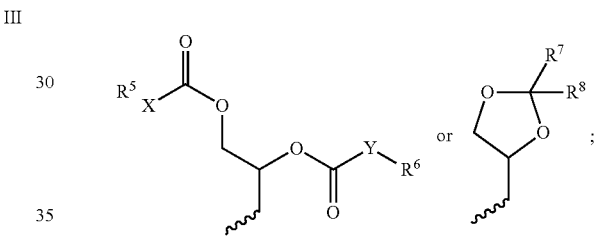

R$^4$ is H, Li, Na, K, Mg, Ca, Zn, Cs, ammonium or tetraalkylammonium, wherein Li, Na and K form monomeric salts and wherein Mg, Ca, Zn and Cs form a salt, e.g., a monomeric salt, a dimeric salt, a trimeric salt, or a multimeric salt;

R$^5$ is a C$_1$-C$_{10}$ branched or unbranched hydrocarbon optionally substituted with one or more groups selected from OH, OAc, OMe, NH$_2$, NHAc, NHMe, N(Me)$_2$, SH, CN, COOH, CONH$_2$, Cl, Br and I;

R$^6$ is a C$_1$-C$_{10}$ branched or unbranched hydrocarbon optionally substituted with one or more groups selected from OH, OAc, OMe, NH$_2$, NHAc, NHMe, N(Me)$_2$, SH, CN, COOH, CONH$_2$, Cl, Br and I;

R$^7$ is a C$_0$-C$_{20}$ branched or unbranched hydrocarbon possessing 0-10 double bonds, 0-10 triple bonds or a combination of 0-10 double and triple bonds;

R$^8$ is H or a C$_0$-C$_{20}$ branched or unbranched hydrocarbon possessing 0-10 double bonds, 0-10 triple bonds or a combination of 0-10 double and triple bonds;

X is a direct linkage, CH$_2$, O or NH;

Y is a direct linkage, CH$_2$, O or NH; and,

Each stereogenic center is independently R, S or racemic;

Comprising the steps of:
(1) Converting the hydroxyl groups of a compound of Formula II to esters, carbonates, carbamates, or collectively to an acetal or a ketal

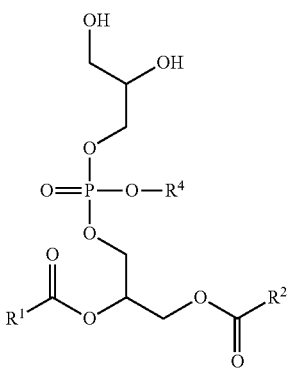

II wherein, all substitutions are defined as above; and
(3) Converting a phosphorus-bound OH group to O—$R^4$, wherein $R^4$ is not H; or Comprising the steps of:
(1) Linking a compound of Formula III with a compound of Formula IV or with a compound of Formula V through creation of a phosphate diester bridge

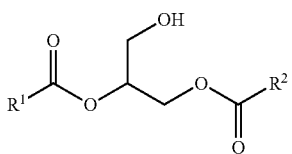

III

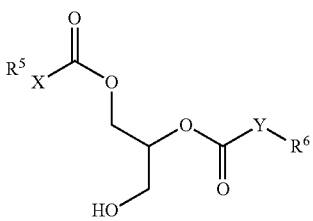

IV

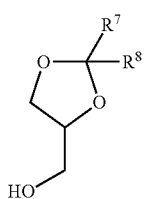

V wherein, all substitutions are defined as above; and
(2) Converting a phosphorus-bound OH group to O—$R^4$, wherein $R^4$ is not H.

As defined generally above, $R^1$ is a $C_1$-$C_{20}$ branched or unbranched hydrocarbon possessing 0-10 double bonds, 0-10 triple bonds or a combination of 0-10 double and triple bonds. In some embodiments, $R^1$ is a $C_1$-$C_{15}$ branched or unbranched hydrocarbon possessing 0-7 double bonds, 0-7 triple bonds or a combination of 0-7 double and triple bonds. In some embodiments, $R^1$ is a $C_1$-$C_{10}$ branched or unbranched hydrocarbon possessing 0-5 double bonds, 0-5 triple bonds or a combination of 0-5 double and triple bonds. In some embodiments, $R^1$ is a $C_{11}$-$C_{20}$ branched or unbranched hydrocarbon possessing 0-5 double bonds, 0-5 triple bonds or a combination of 0-5 double and triple bonds. In some embodiments, $R^1$ is a $C_5$-$C_{15}$ branched or unbranched hydrocarbon possessing 0-5 double bonds, 0-5 triple bonds or a combination of 0-5 double and triple bonds. In some embodiments, $R^1$ is a $C_1$-$C_5$ branched or unbranched hydrocarbon possessing 0-2 double bonds, 0-2 triple bonds or a combination of 0-2 double and triple bonds. In some embodiments, $R^1$ is a $C_{10}$-$C_{15}$ branched or unbranched hydrocarbon.

As defined generally above, $R^2$ is a $C_1$-$C_{20}$ branched or unbranched hydrocarbon possessing 0-10 double bonds, 0-10 triple bonds or a combination of 0-10 double and triple bonds. In some embodiments, $R^2$ is a $C_1$-$C_{15}$ branched or unbranched hydrocarbon possessing 0-7 double bonds, 0-7 triple bonds or a combination of 0-7 double and triple bonds. In some embodiments, $R^2$ is a $C_1$-$C_{10}$ branched or unbranched hydrocarbon possessing 0-5 double bonds, 0-5 triple bonds or a combination of 0-5 double and triple bonds. In some embodiments, $R^2$ is a $C_{11}$-$C_{20}$ branched or unbranched hydrocarbon possessing 0-5 double bonds, 0-5 triple bonds or a combination of 0-5 double and triple bonds. In some embodiments, $R^2$ is a $C_5$-$C_{15}$ branched or unbranched hydrocarbon possessing 0-5 double bonds, 0-5 triple bonds or a combination of 0-5 double and triple bonds. In some embodiments, $R^2$ is a $C_1$-$C_5$ branched or unbranched hydrocarbon possessing 0-2 double bonds, 0-2 triple bonds or a combination of 0-2 double and triple bonds. In some embodiments, $R^2$ is a $C_{10}$-$C_{15}$ branched or unbranched hydrocarbon.

As defined generally above, both $R^1$ and $R^2$ have the same definition. In some embodiments, $R^1$ and $R^2$ are the same. In some embodiments, $R^1$ and $R^2$ are different.

As defined generally above, $R^3$ is

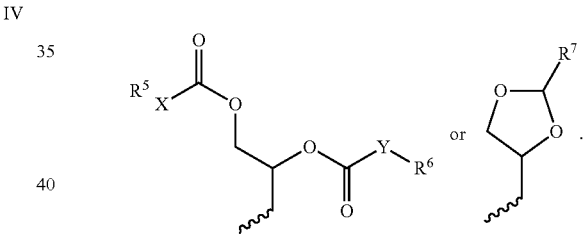

In some embodiments, $R^3$ is

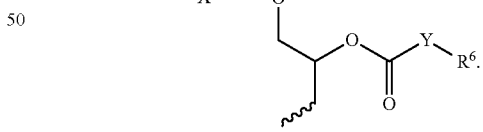

In some embodiments, $R^3$ is

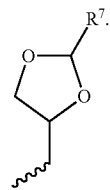

As defined generally above, $R^4$ is H or a pharmaceutically acceptable cation, wherein incorporation of said pharmaceutically acceptable cation results in a salt, e.g., monomeric salt, a dimeric salt, a trimeric salt, or even a multimeric salt. In preferred embodiments, $R^4$ is H, Li, Na, K, Mg, Ca, Zn, Cs, ammonium and tetraalkylammonium. In some embodiments, $R^4$ is H. In some embodiments, $R^4$ is Li. In some embodiments, $R^4$ is Na. In some embodiments, $R^4$ is K. In some embodiments, $R^4$ is Mg. In some embodiments, $R^4$ is Ca. In some embodiments, $R^4$ is Zn. In some embodiments, $R^4$ is Cs. In some embodiments, $R^4$ is ammonium. In some embodiments, $R^4$ is tetraalkylammonium.

As defined generally above, $R^5$ is a $C_1$-$C_{10}$ branched or unbranched hydrocarbon optionally substituted with one or more groups selected from OH, OAc, OMe, $NH_2$, NHAc, NHMe, $N(Me)_2$, SH, CN, COOH, $CONH_2$, Cl, Br and I.

As defined generally above, $R^6$ is a $C_1$-$C_{10}$ branched or unbranched hydrocarbon optionally substituted with one or more groups selected from OH, OAc, OMe, $NH_2$, NHAc, NHMe, $N(Me)_2$, SH, CN, COOH, $CONH_2$, Cl, Br and I;

As defined generally above, both $R^5$ and $R^6$ have the same definition. In some embodiments, $R^5$ and $R^6$ are the same. In some embodiments, $R^5$ and $R^6$ are different.

As defined generally above, $R^7$ is a $C_1$-$C_{20}$ branched or unbranched hydrocarbon possessing 0-10 double bonds, 0-10 triple bonds or a combination of 0-10 double and triple bonds. In some embodiments, $R^7$ is a $C_1$-$C_{15}$ branched or unbranched hydrocarbon possessing 0-7 double bonds, 0-7 triple bonds or a combination of 0-7 double and triple bonds. In some embodiments, $R^7$ is a $C_1$-$C_{10}$ branched or unbranched hydrocarbon possessing 0-5 double bonds, 0-5 triple bonds or a combination of 0-5 double and triple bonds. In some embodiments, $R^7$ is a $C_{11}$-$C_{20}$ branched or unbranched hydrocarbon possessing 0-5 double bonds, 0-5 triple bonds or a combination of 0-5 double and triple bonds. In some embodiments, $R^7$ is a $C_5$-$C_{15}$ branched or unbranched hydrocarbon possessing 0-5 double bonds, 0-5 triple bonds or a combination of 0-5 double and triple bonds. In some embodiments, $R^7$ is a $C_1$-$C_5$ branched or unbranched hydrocarbon possessing 0-2 double bonds, 0-2 triple bonds or a combination of 0-2 double and triple bonds. In some embodiments, $R^7$ is a $C_{10}$-$C_{15}$ branched or unbranched hydrocarbon.

As defined generally above, $R^8$ is H or a $C_0$-$C_{20}$ branched or unbranched hydrocarbon possessing 0-10 double bonds, 0-10 triple bonds or a combination of 0-10 double and triple bonds. In some embodiments, $R^8$ is H. In some embodiments, $R^8$ is a $C_0$-$C_{20}$ branched or unbranched hydrocarbon possessing 0-10 double bonds, 0-10 triple bonds or a combination of 0-10 double and triple bonds.

As defined generally above, $R^7$ and $R^8$ are similar. In some embodiments, $R^7$ and $R^8$ are the same. In some embodiments, $R^7$ and $R^8$ are different.

As defined generally above, X is a direct linkage, $CH_2$, O or NH. In some embodiments, X is a direct linkage. In some embodiments, X is $CH_2$. In some embodiments, X is O. In some embodiments, X is NH.

As defined generally above, Y is a direct linkage, $CH_2$, O or NH. In some embodiments, Y is a direct linkage. In some embodiments, Y is $CH_2$. In some embodiments, Y is O. In some embodiments, Y is NH.

As defined generally above, both X and Y have the same definition. In some embodiments, X and Y are the same. In some embodiments, X and Y are different.

As defined generally above, each stereogenic center is independently R, S or racemic.

In different embodiments, the present invention has a structure of Compounds 1-30.

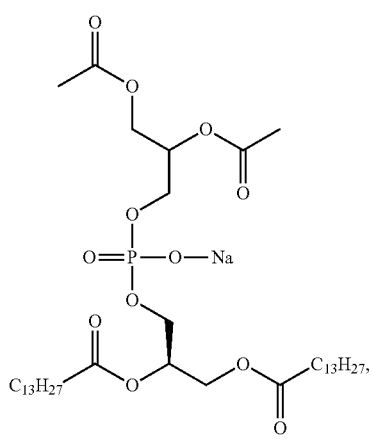

1

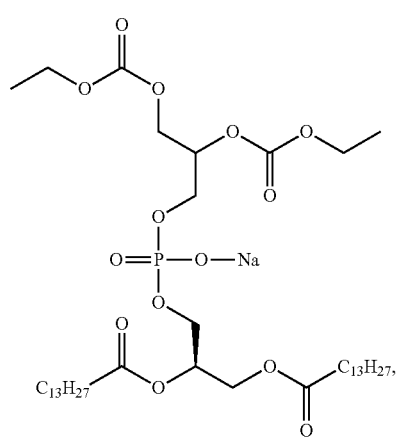

2

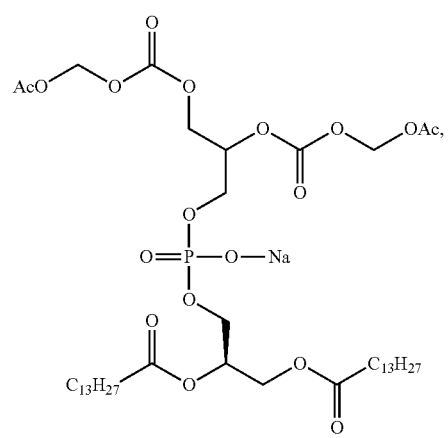

3

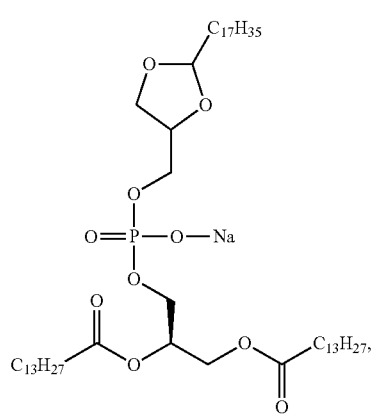
4
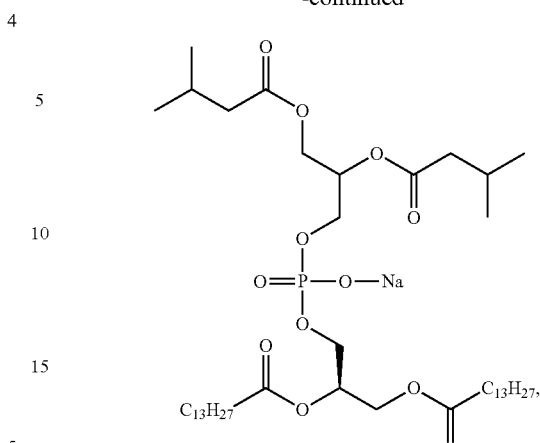
8
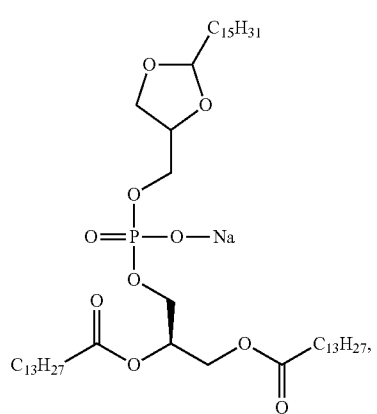
5
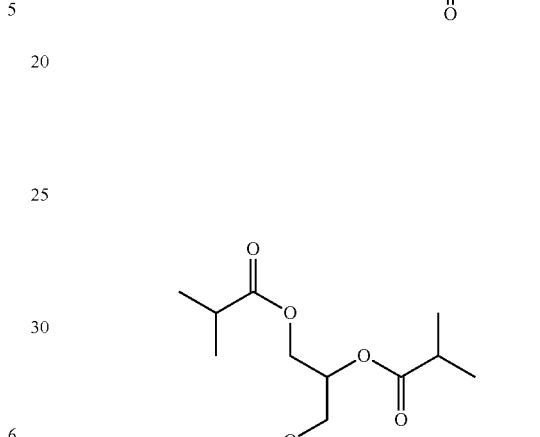
9
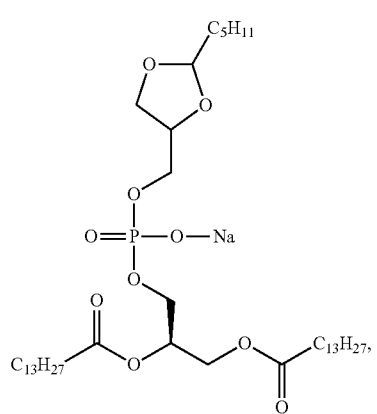
6
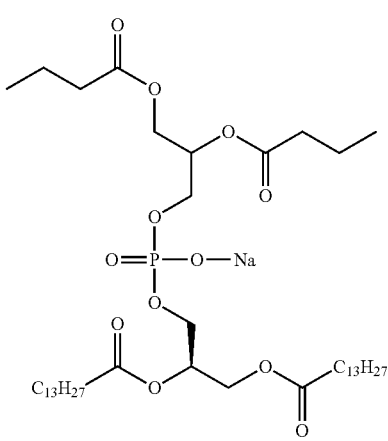
7
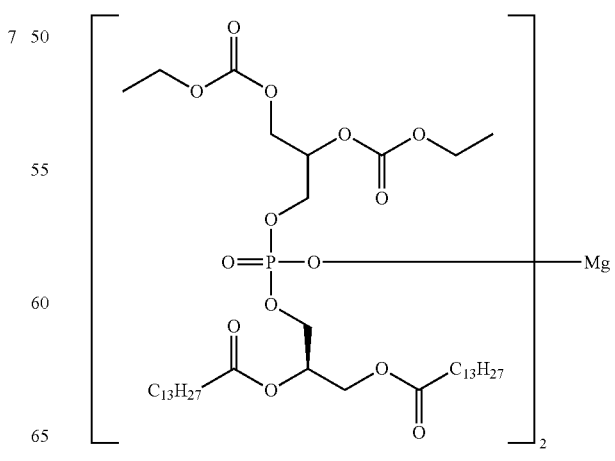
10

31
-continued
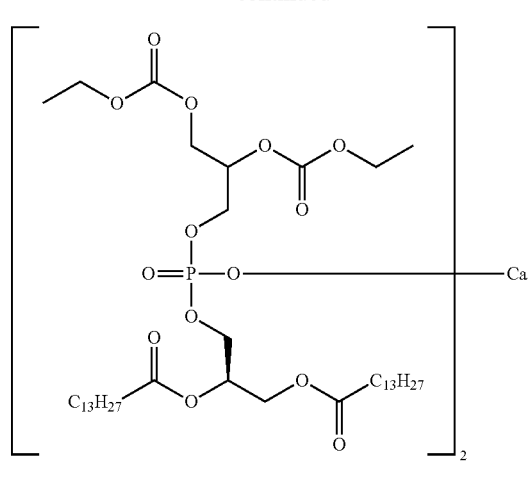
11
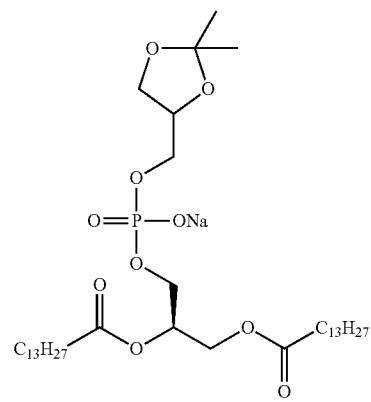
12
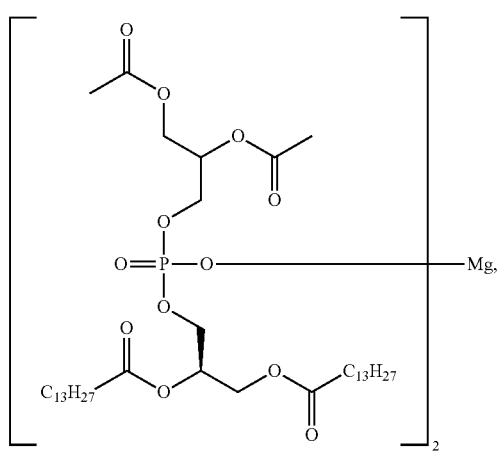
13
32
-continued
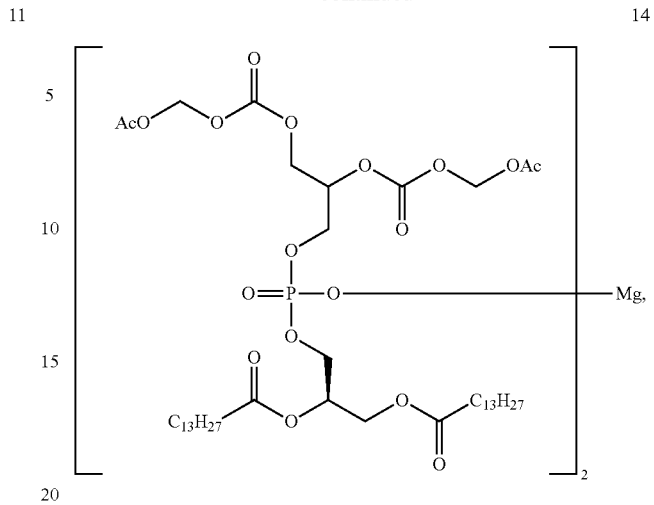
14
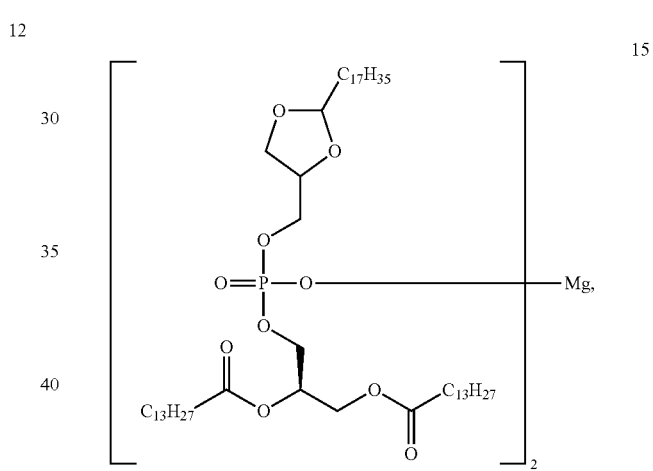
15
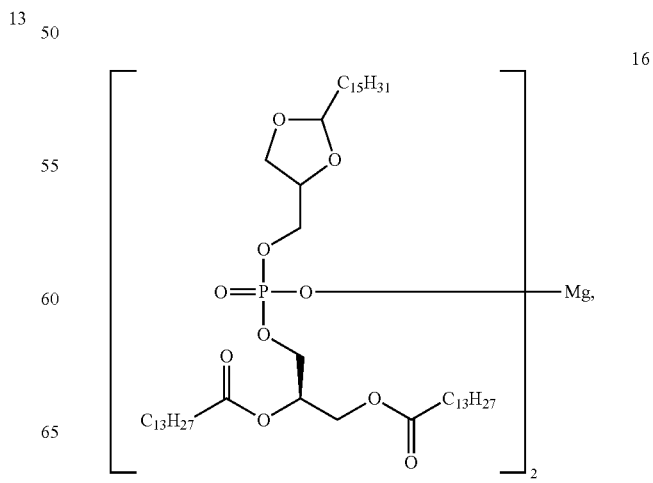
16

33
-continued
34
-continued
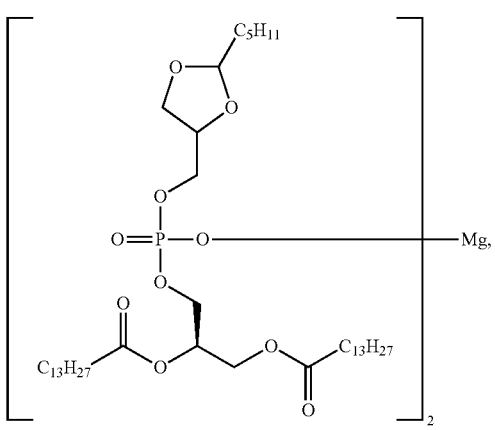
17
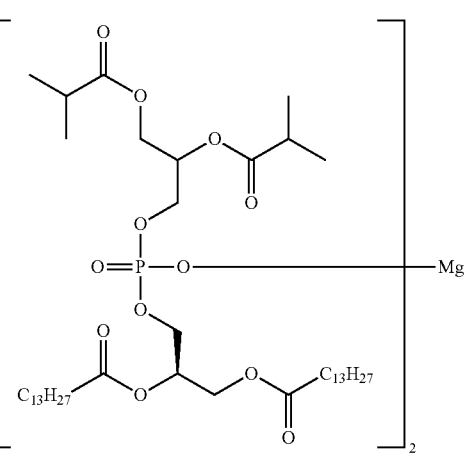
20
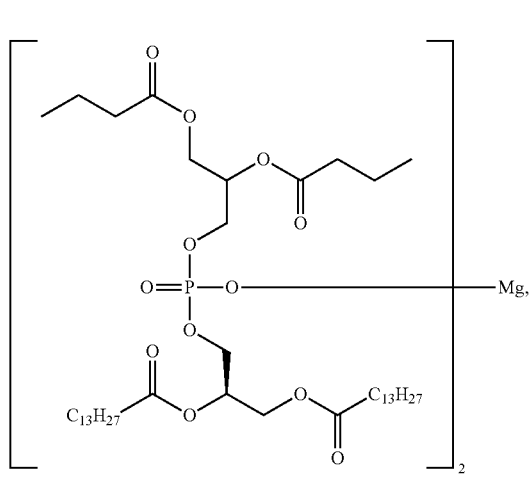
18
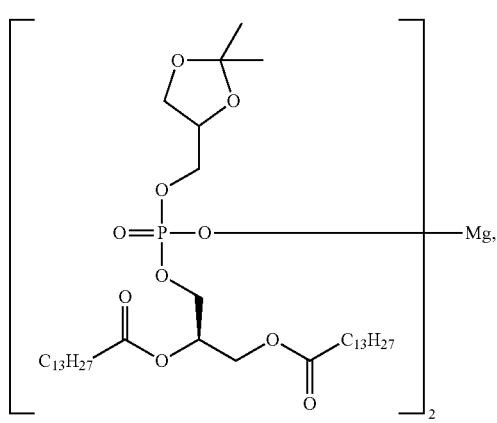
21
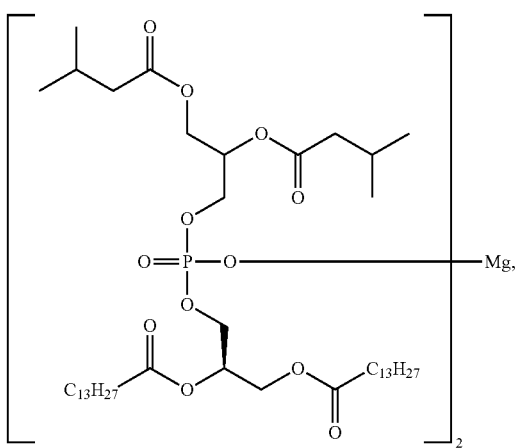
19
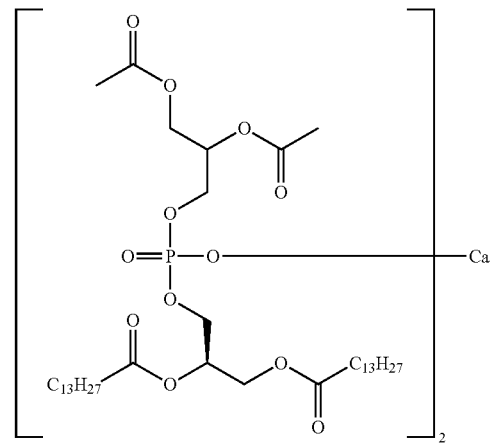
22

35
-continued
23
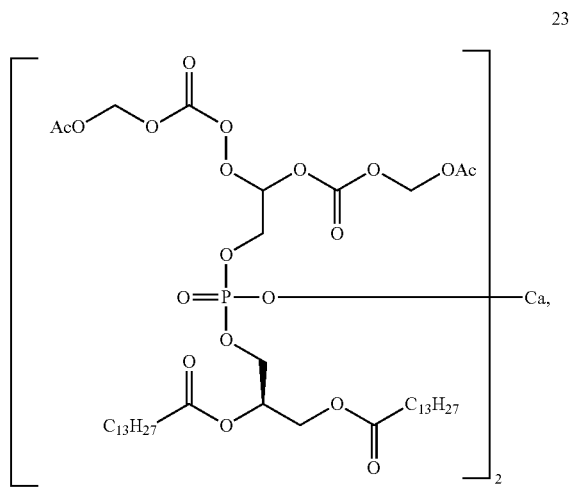
24
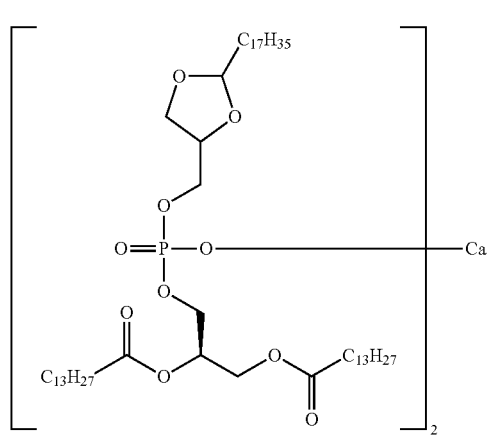
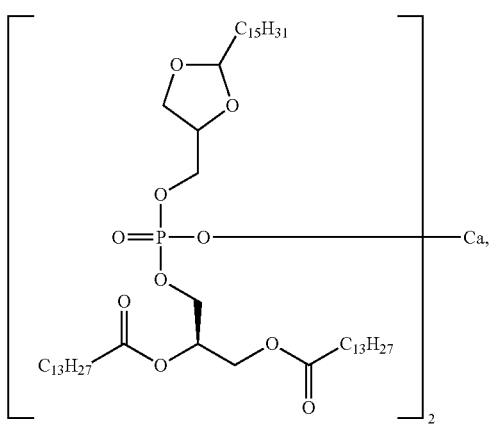
36
-continued
26
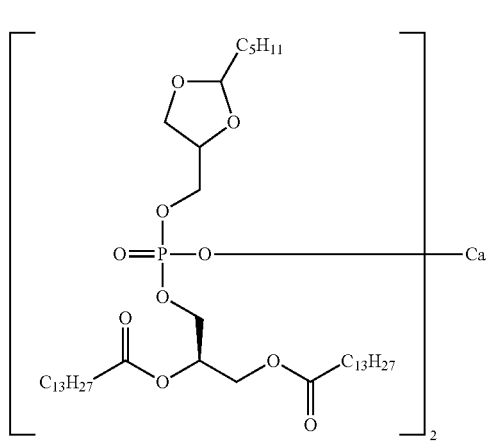
27
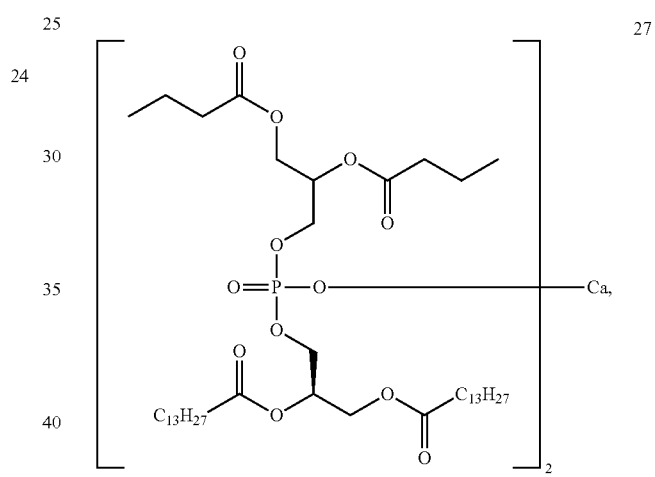
28
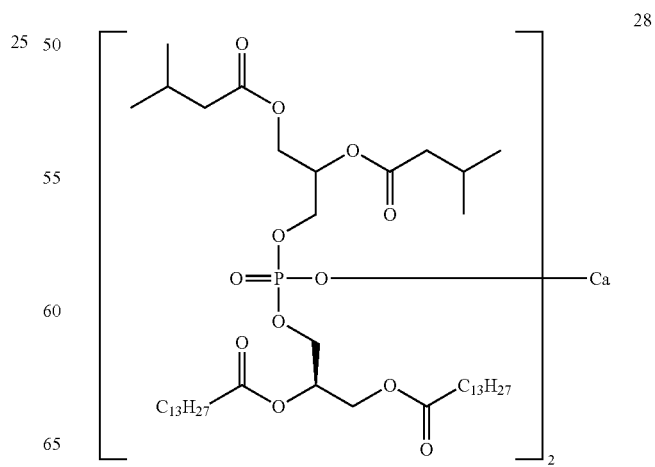

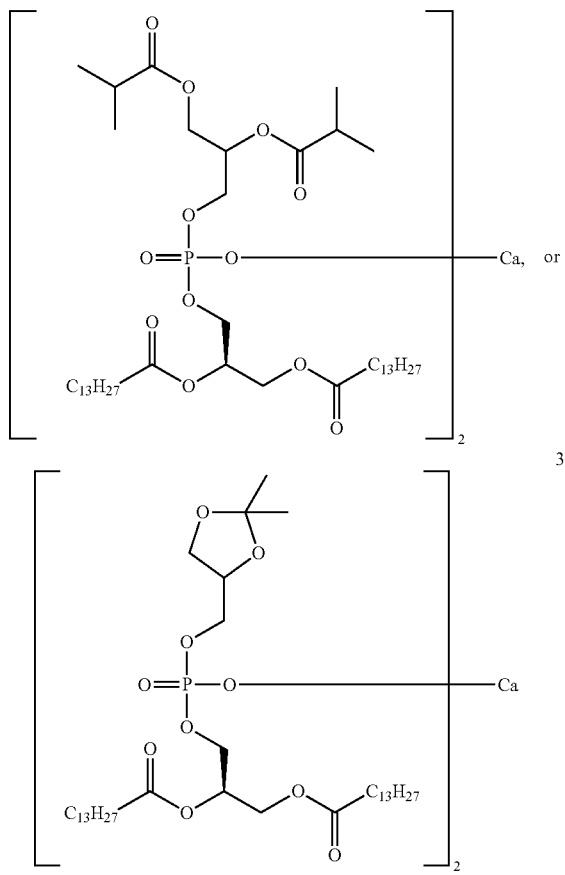

One embodiment of this invention relates to pharmaceutical compositions comprising a compound of Formula I and a pharmaceutically acceptable diluent or carrier. In one embodiment, said pharmaceutical compositions comprise a compound of Formula I in an amount per unit dose of between about 1 mg and about 1 gram. In some embodiments, the amount per unit dose is between about 1 mg and about 500 mg. In some embodiments, the amount per unit dose is between about 500 mg and about 1 gram. In some embodiments, the amount per unit dose is between about 250 mg and about 750 mg. In some embodiments, the amount per unit dose is between about 50 mg and about 450 mg. In some embodiments, the amount per unit dose is between about 100 mg and about 300 mg.

In some embodiments, said pharmaceutical compositions additionally comprise one or more agents that induce a cardiopathy as a side effect, and wherein the compound of Formula I reduces or eliminates the cardiopathy. In some embodiments, the one or more agents that induce a cardiopathy as a side effect are selected from at least one of: Albuterol, Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Cocaine, Curcumin, Crizotinib, Dabrafenib, Dasatinib, Desipramine, Dexmedetomidine, Dexmethylphenidate, Dextroamphetamine, Amphetamine, Dihydroartemisinin and Piperaquine, Diphenhydramine, Disopyramide, Dobutamine, Dofetilide, Dolasetron, Domperidone, Dopamine, Doxepin, Dronedarone, Droperidol, Ephedrine, Epinephrine, Adrenaline, Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide, Frusemide, Galantamine, Gatifloxacin, Gemifloxacin, Granisetron, Halofantrine, Haloperidol, Hydrochlorothiazide, Ibutilide, Iloperidone, Imipramine, Melipramine, Indapamide, Isoproterenol, Isradipine, Itraconazole, Ivabradine, Ketoconazole, Lapatinib, Levalbuterol, Levofloxacin, Levomethadyl, Lisdexamfetamine, Lithium, Mesoridazine, Metaproterenol, Methadone, Methamphetamine, Methylphenidate, Midodrine, Mifepristone, Mirabegron, Mirtazapine, Moexipril/HCTZ, Moxifloxacin, Nelfinavir, Nicardipine, Nilotinib, Norepinephrine, Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salbutamol, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone. One of ordinary skill in the art will recognize that additional agents that induce a cardiopathy exist and may benefit from inclusion in formulations of the present invention.

In some embodiments, the present invention includes a composition comprising an active agent that causes a cardiopathy and a compound of Formula I represented by one or more compounds of Formula I, for example, Compounds 1 to 30, as set forth above.

One embodiment of this invention provides a pharmaceutical composition comprising a structure of Formula I, for example, Compounds 1 to 30, formulated for oral, sublingual, transdermal, suppository, intrathecal, enteral, parenteral, intravenous, intraperitoneal, cutaneous, subcutaneous, topical, pulmonary, rectal, vaginal, or intramuscular administration, as set forth above. In some embodiments, the composition formulated for oral administration is a tablet, capsule, caplet, pill, powder, troche, lozenge, slurry, liquid solution, suspension, emulsion, elixir or oral thin film (OTF). In some embodiments, the composition is a solid form, a solution, a suspension, or a soft gel form.

One embodiment of this invention provides pharmaceutical compositions comprising an active agent that causes a cardiopathy as a side effect and a compound of Formula I, for example Compounds 1 to 30, as set forth above.

One embodiment of this invention provides a method of reducing or eliminating one or more of a cardiac channelopathy, cardiac muscle damage, or a condition resulting from the irregularity or alteration in the cardiac pattern, in a human or animal subject caused by an active agent used to treat a disease, comprising the steps of: administering to the human or animal subject a pharmaceutical composition comprising a compound of Formula I, for example, Compounds 1 to 30, as set forth above.

In some embodiments, said pharmaceutical compositions additionally comprise one or more excipients, binders, anti-adherents, coatings, disintegrants, fillers, flavors, dyes, colors, glidants, lubricants, preservatives, sorbents, sweeteners, derivatives thereof, or combinations thereof. In some embodiments, the binder is selected from the group consisting of hydroxypropylmethylcellulose, ethyl cellulose, povidone, acrylic and methacrylic acid co-polymers, pharmaceutical glaze, gums, and milk derivatives.

In one embodiment, said pharmaceutical compositions comprise a compound of Formula I in an amount per unit dose of between about 1 mg and about 1 gram. In some embodiments, the amount per unit dose is between about 1 mg and about 500 mg. In some embodiments, the amount per unit dose is between about 500 mg and about 1 gram. In some embodiments, the amount per unit dose is between about 250 mg and about 750 mg. In some embodiments, the amount per unit dose is between about 50 mg and about 450 mg. In some embodiments, the amount per unit dose is between about 100 mg and about 300 mg.

In some embodiments, said pharmaceutical compositions additionally comprise one or more excipients, binders, anti-adherents, coatings, disintegrants, fillers, flavors, dyes, colors, glidants, lubricants, preservatives, sorbents, sweeteners, derivatives thereof, or combinations thereof. In some embodiments, the binder is selected from the group consisting of hydroxypropylmethylcellulose, ethyl cellulose, povidone, acrylic and methacrylic acid co-polymers, pharmaceutical glaze, gums, and milk derivatives.

In one embodiment, the present invention includes a composition, a pharmaceutical composition, and a method in which the active agent that causes a cardiopathy as a side effect is selected from at least one of: Albuterol, Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Cocaine, Curcumin, Crizotinib, Dabrafenib, Dasatinib, Desipramine, Dexmedetomidine, Dexmethylphenidate, Dextroamphetamine, Amphetamine, Dihydroartemisinin and Piperaquine, Diphenhydramine, Disopyramide, Dobutamine, Dofetilide, Dolasetron, Domperidone, Dopamine, Doxepin, Dronedarone, Droperidol, Ephedrine, Epinephrine, Adrenaline, Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide, Frusemide, Galantamine, Gatifloxacin, Gemifloxacin, Granisetron, Halofantrine, Haloperidol, Hydrochlorothiazide, Ibutilide, Iloperidone, Imipramine, Melipramine, Indapamide, Isoproterenol, Isradipine, Itraconazole, Ivabradine, Ketoconazole, Lapatinib, Levalbuterol, Levofloxacin, Levomethadyl, Lisdexamfetamine, Lithium, Mesoridazine, Metaproterenol, Methadone, Methamphetamine, Methylphenidate, Midodrine, Mifepristone, Mirabegron, Mirtazapine, Moexipril/HCTZ, Moxifloxacin, Nelfinavir, Nicardipine, Nilotinib, Norepinephrine, Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salbutamol, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone. One of ordinary skill in the art will recognize that additional agents that induce a cardiopathy exist and may benefit from inclusion in formulations of the present invention.

In some embodiments, said pharmaceutical compositions are formulated for oral, sublingual, transdermal, suppository, intrathecal, enteral, parenteral, intravenous, intraperitoneal, cutaneous, subcutaneous, topical, pulmonary, rectal, vaginal, or intramuscular administration. In some embodiments, said pharmaceutical composition formulated for oral administration is a tablet, capsule, caplet, pill, powder, troche, lozenge, slurry, liquid solution, suspension, emulsion, elixir or oral thin film (OTF). In some embodiments, the composition is a solid form, a solution, a suspension, or a soft gel form. In some embodiments, the solid form further comprises one or more excipients, binders, anti-adherents, coatings, disintegrants, fillers, flavors, dyes, colors, glidants, lubricants, preservatives, sorbents, sweeteners, derivatives thereof, or combinations thereof. In some embodiments, the binder is selected from the group consisting of hydroxypropylmethylcellulose, ethyl cellulose, povidone, acrylic and methacrylic acid co-polymers, pharmaceutical glaze, gums, and milk derivatives.

In one embodiment, said method provides pharmaceutical compositions that comprise a compound of Formula I in an amount per unit dose of between about 1 mg and about 1 gram. In some embodiments, the amount per unit dose is between about 1 mg and about 500 mg. In some embodiments, the amount per unit dose is between about 500 mg and about 1 gram. In some embodiments, the amount per unit dose is between about 250 mg and about 750 mg. In some embodiments, the amount per unit dose is between about 50 mg and about 450 mg. In some embodiments, the amount per unit dose is between about 100 mg and about 300 mg.

In one embodiment, said method provides a pharmaceutical composition formulated for oral, sublingual, transdermal, suppository, intrathecal, enteral, parenteral, intravenous, intraperitoneal, cutaneous, subcutaneous, topical, pulmonary, rectal, vaginal, or intramuscular administration. In some embodiments, said pharmaceutical composition formulated for oral administration is a tablet, capsule, caplet, pill, powder, troche, lozenge, slurry, liquid solution, suspension, emulsion, elixir or oral thin film (OTF). In some embodiments, the composition is a solid form, a solution, a suspension, or a soft gel form. In some embodiments, the solid form further comprises one or more excipients, binders, anti-adherents, coatings, disintegrants, fillers, flavors, dyes, colors, glidants, lubricants, preservatives, sorbents, sweeteners, derivatives thereof, or combinations thereof. In some embodiments, the binder is selected from the group consisting of hydroxypropylmethylcellulose, ethyl cellulose, povidone, acrylic and methacrylic acid co-polymers, pharmaceutical glaze, gums, and milk derivatives.

In one embodiment, said method provides pharmaceutical compositions. One embodiment of this invention provides administration of a compound of Formula I, wherein said compound is a lipid that reduces or eliminates cardiopathies, such as QT prolongation, cardiac muscle damage, or AV block, that are drug-induced or caused by a disease or condition.

The single most common cause of the withdrawal or restriction of the use of marketed drugs has been QT-interval prolongation associated with polymorphic ventricular tachycardia, or torsade de pointes, a condition that can be fatal.

5-HT3 antagonists block serotonin binding. Aloxi (or palonasitron HCL) is an antiemetic for chemotherapy induced nausea and vomiting, a 5-HT 3 antagonist, blocks serotonin binding to 5-HT3. In a study there was no significant difference in the QTc intervals during the perioperative period, whether 0.075 mg of palonosetron is administered before or after sevoflurane anesthesia. Palonosetron may be safe in terms of QTc intervals during sevoflurane anesthesia.

5-HT4 receptor agonist. Cisapride is a gastroprokinetic agent, a drug that increases motility in the upper gastrointestinal tract. It acts directly as a serotonin 5-HT4 receptor agonist and indirectly as a parasympathomimetic. Cisapride dose-dependently prolongs the QT interval. Neither torsade de pointe nor ventricular tachycardia were noted when monitoring 33 patients during a higher dose stage.

Histamine Antagonist. Antihistamines used in the treatment of allergy act by competing with histamine for H1-receptor sites on effector cells. They thereby prevent, but do not reverse, responses mediated by histamine alone.

Pain and Premenstrual Symptom Relief H1 antagonists are most useful in acute exudative types of allergy that present with symptoms of rhinitis, urticaria, and conjunctivitis. Their effect, however, is purely palliative and confined to the suppression of symptoms attributable to the histamine-antibody reaction Pyrilamine is a diuretic first-generation histamine H1 antagonist. There is a case of an adolescent with prolonged QT interval after an overdose of pyrilamine. Reports of deaths resulting from ventricular tachyarrhythmias have been made.

Terfenidine is an antihistamine, used to treat allergies, hives (urticaria), and other allergic inflammatory conditions. The brand name Seldane is discontinued in the U.S. Rare reports of severe cardiovascular adverse effects have been received which include ventricular tachyarrhythmias (torsades de pointes, ventricular tachycardia, ventricular fibrillation, and cardiac arrest), hypotension, palpitations, or syncope.

Loratidine is a first-line antihistamine is a second-generation peripheral histamine H1-receptor blocker. In structure, it is closely related to tricyclic antidepressants, such as imipramine, and is distantly related to the atypical antipsychotic quetiapine. Some antihistamines, such as mizolastine and ebastine, can prolong the QT interval and provoke severe cardiac arrhythmias. As of mid 2009 very few clinical data had been published on the risk of QT prolongation with loratadine. Very rare reported cases of torsades de pointes linked to loratadine mainly appear to involve drug interactions, especially with amiodarone and enzyme inhibitors. There are no reports of QT prolongation attributed to desloratadine, the main metabolite of loratadine. Patients who have risk factors for torsades de pointes or who are taking certain enzyme inhibitors should avoid using loratadine.

Astemizole is a long-acting and highly selective H1 antagonist, acting on histamine H-1 receptor and H-3 receptors. It has antipruritic, and anticholinergic effects. It is also afunctional inhibitor of acid sphingomyelinase. An overdose of astemizole predisposes the myocardium to ventricular dysrhythmias, including torsades de pointes. However, dysrhythmias developed only in patients with corrected QT intervals greater than 500 ms.

Calcium channel blocker. Prenylamine is a calcium channel blocker of the amphetamine chemical class that is used as a vasodilator in the treatment of angina pectoris. Resting ECGs were recorded in 29 patients with angina pectoris before, during and after treatment with prenylamine 180 mg daily. The QT interval became significantly prolonged after one week of treatment. The prolongation persisted as long as therapy was continued, which was up to 6 months. After withdrawal of treatment the QT interval returned to normal within 2 weeks.

Lidoflazine is a piperazine calcium channel blocker is a coronary vasodilator with some antiarrhythmic action. As a tricyclic antihistamine, It acts as a selective inverse agonist of peripheral histamine H1-receptors. It carries a significant risk of QT interval prolongation and ventricular arrhythmia. Lidoflazine inhibits potently HERG current (I(HERG)) recorded from HEK 293 cells stably expressing wild-type HERG (IC(50) of approximately 16 nM). It is approximately 13-fold more potent against HERG than verapamil under similar conditions in preferentially inhibiting activated/open HERG channels. Lidoflazine produces high affinity blockade of the alpha subunit of the HERG channel by binding to aromatic amino acid residues within the channel pore and, second, that this is likely to represent the molecular mechanism of QT interval prolongation by this drug.

Bepridil is an antihypertensive drug which disrupts the movement of calcium (Ca2+) through calcium channels. While it prolongs the QT interval. Bepridil prolongs the QT and refractoriness and a linear correlation could be demonstrated between the percent change in QTc and refractory period prolongation. Bepridil in one patient reduced by one the number of stimuli required to induce VT, but no spontaneous arrhythmias were noted, It possesses antiarrhythmic properties with a minimal proarrhythmic effect.

Antimalarials. Chloroquine-Chlorpheniramine (chloroquine plus chlorpheniramine) is a histamine H1 receptor blocker that reverses chloroquine insensitivity in *Plasmodium falciparum* in vitro, Chloroquine/chlorpheniramine produces a higher cure rate than chloroquine alone. Short QT Syndrome (SQTS) is a sporadic or autosomal dominant disorder characterized by markedly accelerated cardiac repolarization, ventricular arrhythmias and sudden cardiac death. To date, mutations in 5 different ion channel genes (KCNH2, KCNQ1, KCNJ2, CACNA1C and CACNB2) have been identified to cause SQTS. The risk of ventricular arrhythmias and sudden death is remarkably high in SQTS with cardiac arrest reported as a presenting symptom in 31% of SQTS subjects. Chloroquine Blocks a Mutant Kir2.1 Channel Responsible for Short QT Syndrome and Normalizes Repolarization Properties in silico.

Halofantrine is an antimalarial agent with a substituted phenanthrene, and is related to the antimalarial drugs quinine and lumefantrine. It can be associated with cardiotoxicity. The most dangerous side effect is cardiac arrhythmias: halofantrine causes significant QT prolongation, and this effect is seen even at standard doses. The drug should therefore not be given to patients with cardiac conduction defects and should not be combined with mefloquine. The mechanism of action of halofantrine is unknown.

Quinidine is an antimalarial that acts as a class I antiarrhythmic agent (Ia) in the heart. It is a stereoisomer of quinine, This alkaloid dampens the excitability of cardiac and skeletal muscles by blocking sodium and potassium currents across cellular membranes. It prolongs cellular action potential, and decreases automaticity. Quinidine also blocks muscarinic and alpha-adrenergic neurotransmission. Quinidine causes greater QT prolongation in women than in men at equivalent serum concentrations. This difference may contribute to the greater incidence of drug-induced torsades de pointes observed in women taking quinidine and has implications for other cardiac and noncardiac drugs that prolong the QTc interval.

Antipsychotics. First-generation antipsychotics, known as typical antipsychotics, were discovered in the 1950s. Most second-generation drugs, known as atypical antipsychotics, have been developed more recently, although the first atypical antipsychotic, clozapine, was discovered in the 1960s and introduced clinically in the 1970s. Both generations of medication tend to block receptors in the brain's dopamine pathways, but atypicals tend to act on serotonin receptors as well. Both generations of medication tend to block receptors in the brain's dopamine pathways, but atypicals tend to act on serotonin receptors as well. QTc interval prolongation can occur as a result of treatment with both conventional and novel antipsychotic medications and is of clinical concern because of its association with the potentially fatal ventricular arrhythmia, torsade de pointes.

Pimozide is an antipsychotic drug of the diphenylbutylpiperidine class, Can induce prolongation of the QT interval. Pimozide is contraindicated in individuals with either acquired, congenital or a family history of QT interval prolongation. Its use is advised against in individuals with people with either a personal or a family history of arrhythmias or torsades de pointe acts as an antagonist of the D2, D3, and D4 receptors and the 5-HT7 receptor. It is also a hERG blocker.

Sertindole is an antipsychotic medication. Like other atypical antipsychotics, it has activity at dopamine and serotonin receptors in the brain. Abbott Labs first applied for U.S. Food and Drug Administration (FDA) approval for sertindole in 1996, but withdrew this application in 1998 following concerns over the increased risk of sudden death from QTc prolongation. In a trial of 2000 patients on taking sertindole, 27 patients died unexpectedly, including 13 sudden deaths. The drug has not been approved by the FDA for use in the USA. In Europe, Sertindole was approved and marketed in 19 countries from 1996, but its marketing authorization was suspended by the European Medicines Agency in 1998 and the drug was withdrawn from the market. In 2002, based on new data, the EMA's CHMP suggested that Sertindole could be reintroduced for restricted use in clinical trials, with strong safeguards including extensive contraindications and warnings for patients at risk of cardiac dysrhythmias, a recommended reduction in maximum dose from 24 mg to 20 mg in all but exceptional cases, and extensive ECG monitoring requirement before and during treatment Chlorpromazine, marketed as Thorazine and Largactil, is an antipsychotic medication in the typical antipsychotic class. Its mechanism of action is not entirely clear but believed to be related to its ability as a dopamine antagonist. It also has anti-serotonergic and anti-histaminergic properties. Chlorpromazine is a very effective antagonist of D2 dopamine receptors and similar receptors, such as D3 and D5. Unlike most other drugs of this genre, it also has a high affinity for D1 receptors. Electrocardiogram QT corrected interval prolonged is reported only by a few people who take Thorazine. In a study of 2,633 people who have side effects while taking Thorazine from FDA and social media, 5 have electrocardiogram QT corrected interval prolonged.

Thioridazine is a piperidine typical antipsychotic drug belonging to the phenothiazine drug branded product was withdrawn worldwide in 2005 because it caused severe cardiac arrhythmias, however, generic versions are available in the US. The drug was voluntarily discontinued by its manufacturer, Novartis, worldwide because it caused severe cardiac arrhythmias. Thioridazine prolongs the QTc interval in a dose-dependent manner. The ratio of 5-HT2A to D2 receptor binding is believed to dictate whether or not most antipsychotics are atypical or typical. In thioridazine's case its ratio of 5-HT2A to D2 receptor binding is below the level that's believed to be required for atypicality despite its relatively low extrapyramidal side effect liability in practice.

Haldol, Haloperidol. A typical antipsychotic medication QT interval prolongation is meperidine. It is on the WHO Model List of Essential Medicines, It is the most commonly used typical antipsychotic, Special cautions: patients at special risk for the development of QT prolongation (hypokalemia, concomitant use of other drugs causing QT Amiodarone: Q-Tc interval prolongation (potentially dangerous change in heart rhythm prolongation).

Mesoridazone is a piperidine neuroleptic drug belonging to the class of drugs called phenothiazines, used in the treatment of schizophrenia. It is a metabolite of thioridazine. Mesoridazone was withdrawn from the United States market in 2004 due to dangerous side effects, namely irregular heart beat and QT-prolongation of the electrocardiogram.

Selective serotonin reuptake inhibitors. Celexa (citalopram) is an antidepressant in a group of drugs called selective serotonin reuptake inhibitors (SSRIs). Its chemical structure a racemic bicyclic phthalane derivative designated ($\pm$)-1-(3-dimethylaminopropyl)-1-(4-fluorophenyl)-1,3-dihydroisobenzofuran-5-carbonitrile, is unrelated to that of other SSRIs, or other available antidepressant agents. Citalopram may cause a condition that affects the heart rhythm (QT prolongation).

Antibiotics. Moxifloxacin is a fourth-generation synthetic fluoroquinolone antibacterial agent. It functions by inhibiting DNA gyrase, a type II topoisomerase, and topoisomerase IV (enzymes necessary to separate bacterial DNA thereby inhibiting cell replication) may cause torsade de pointes. Coadministration of moxifloxacin with other drugs that also prolong the QT interval or induce bradycardia (e.g., beta-blockers, amiodarone) should be avoided. Careful consideration should be given in the use of moxifloxacin in patients with cardiovascular disease, including those with conduction abnormalities. Drugs that prolong the QT interval may have an additive effect on QT prolongation and lead to increased risk of ventricular arrhythmias.

Pentamadine is an antimicrobial medication given to prevent and treat *pneumocystis* pneumonia. The exact mechanism of its anti-protozoal action is unknown (though it may involve reactions with ubiquitin and mitochondrial function. Severe or fatal arrhythmias and heart failure are quite frequent. the aromatic diamidine pentamidine acts via inhibition of hERG channel trafficking. Pentamidine has no acute effects on currents produced by hERG, KvLQT1/mink, Kv4.3, or SCNA5. After overnight exposure, however, pentamidine reduces hERG currents and inhibited trafficking and maturation of hERG with IC50 values of 5 to 8 μM similar to therapeutic concentrations.

Clarithromycin is an antibiotic made from erythromycin is chemically known as 6-O-methylerythromycin. It is in the macrolide class and works by stopping the making of protein by some bacteria. It causes QT prolongation or ventricular cardiac arrhythmias, including torsade de pointes.

Erythromycin is an antibiotic with common side effects that include serious side effects arrhythmia with prolonged QT intervals including torsades de pointes.

Grepafloxacin is an oral broad-spectrum fluoroquinolone antibacterial agent used to treat bacterial infections. Grepafloxacin was withdrawn worldwide from markets in 1999, owing to its side effect of lengthening the QT interval on the electrocardiogram, leading to cardiac events and sudden death.

Sparfloxacin is a fluoroquinolone broad-spectrum antibiotic used in the treatment of bacterial infections. It has a controversial safety profile. The use of sparfloxacin is contraindicated in patients with known QTc prolongation and in patients treated concomitantly with class IA or III antiarrhythmic drugs. In a study, the maximum plasma concentration (Cmax) after the 1200- and 1600-mg doses was lower than would be expected for a linear dose relationship. This was also the case with the mean increase and mean maximum increase in QTc interval. Increases in the QTc interval correlated well with $C_{max}$ but not with AUCo-infinity.

Curcumin (diferuloylmethane) is a bright yellow chemical produced by some plants. It is the principal curcuminoid of turmeric (Curcuma longa) and exerts antioxidant, anti-inflammatory, antiviral, antibacterial, antifungal, and antitumor activities. In whole-cell patch-clamp experiments, curcumin inhibited hERG K+ currents in HEK293 cells stably expressing hERG channels in a dose-dependent manner, with IC50 value of 5.55 µM. The deactivation, inactivation and the recovery time from inactivation of hERG channels were significantly changed by acute treatment of 10 µM curcumin.

Antiarrhythmics. Antiarrhythmics are used to suppress abnormal rhythms of the heart (cardiac arrhythmias), such as atrial fibrillation, ventricular tachycardia, and ventricular fibrillation. Procainamide is an antiarrhythmic class used for the treatment of cardiac arrhythmias. It is classified by the Vaughan Williams classification system as class Ia, and is used for both supraventricular and ventricular arrhythmias. It was also detected that the antiarrhythmic drug procainamide interferes with pacemakers. Because a toxic level of procainamide leads to decrease in ventricular conduction velocity and increase of the ventricular refractory period. This results in a disturbance in the artificial membrane potential and leads to a supraventricular tachycardia, which induces failure of the pacemaker and death. It induces rapid block of the batrachotoxin (BTX)-activated sodium channels of the heart muscle and acts as antagonist to long gating closures Procainamide belongs to the aminobenzamides, which has similar cardiac effects as quinidine it has the same toxicity profile as quinidine.

Propafenone is a class 1C anti-arrhythmic medication, which treats illnesses associated with rapid heartbeats such as atrial and ventricular arrhythmias and works by slowing the influx of sodium ions into the cardiac muscle cells, causing a decrease in excitability of the cells. Propafenone is more selective for cells with a high rate, but also blocks normal cells more than class Ia or Ib. Propafenone differs from the prototypical class Ic antiarrhythmic in that it has additional activity as a beta-adrenergic blocker, which can cause bradycardia.

Methanesulphonanilide (E-4031) is an experimental class III antiarrhythmic drug that blocks potassium channels of class III antiarrhythmic drug. E-4031 acts on a specific class of voltage-gated potassium channels mainly found in the heart, the hERG channels. hERG channels (Kv11.1) mediate the IKr current, which repolarizes the myocardial cells. The hERG channel is encoded by ether-a-go-go related gene (hERG). E-4031 blocks hERG-type potassium channels by binding to the open channels. Its structural target within the hERG-channel is unclear, but some other methanesulfonanilide class III antiarrhythmic drugs are known to bind to the S6 domain or C-terminal of the hERG-channel. As E-4031 can prolong the QT-interval, it can cause lethal arrhythmias. So far, one clinical trial has been conducted to test the effect of E-4031 on prolongation of the QT-interval.

Amiodarone is a class III antiarrhythmic for ventricular fibrillation or tachycardia, prolongs phase 3 of the cardiac action potential. Amiodarone is an antiarrhythmic agent known to cause prolongation of action potential duration, which is reflected in the electrocardiogram as a prolongation of the QT. Amiodarone has multiple effects on myocardial depolarization and repolarization that make it an extremely effective antiarrhythmic drug. Its primary effect is to block the potassium channels, but it can also block sodium and calcium channels and the beta and alpha adrenergic receptors. Amiodarone significantly prolongs the QT interval and the QTc value.

Dronedarone is a benzofuran derivative related to amiodarone, is a drug used mainly for cardiac arrhythmias (approved by the FDA in 2009). It is a "multichannel blocker", however, it is unclear which channel(s) play a pivotal role in its success. Dronedarone's actions at the cellular level are controversial with most studies suggesting an inhibition in multiple outward potassium currents including rapid delayed rectifier, slow delayed rectifier and ACh-activated inward rectifier. It is also believed to reduce inward rapid Na current and L-type Ca channels. The reduction in K current in some studies was shown to be due to the inhibition of K-ACh channel or associated GTP-binding proteins. A reduction of K+ current by 69% led to increased AP duration and increased effective refractory periods, Displays amiodarone-like class III antiarrhythmic activity in vitro and in clinical trials. The drug also appears to exhibit activity in each of the 4 Vaughan-Williams antiarrhythmic classes. Contraindicated in Concomitant use of drugs or herbal products that prolong the QT interval and may induce Torsade de Pointes QTc Bazett interval ≥500 ms, or use with drugs or herbal supplements that prolong QT interval or increase risk of torsades de points (Class I or III antiarrhythmic agents, phenothiazines, tricyclic antidepressants, certain oral macrolides, ephedra).

Disopyramide is an antiarrhythmic medication used in the treatment of ventricular tachycardia. It is a sodium channel blocker and therefore classified as a Class 1a anti-arrhythmic agent. Disopyramide's Class 1a activity is similar to that of quinidine in that it targets sodium channels to inhibit conduction. Disopyramide depresses the increase in sodium permeability of the cardiac Myocyte during Phase 0 of the cardiac action potential, in turn decreasing the inward sodium current. This results in an increased threshold for excitation and a decreased upstroke velocity Disopyramide prolongs the PR interval by lengthening both the QRS and P wave duration. Concern about diisopyramide has been the hypothetical potential for inducing sudden death from its type 1 anti-arrhythmic effects.

Dofetilide is a class III antiarrhythmic agent. Due to the pro-arrhythmic potential of dofetilide, it is only available by prescription from physicians who have undergone specific training in the risks of treatment with dofetilide. In addition, it is only available by mail order or through specially trained local pharmacies Dofetilide works by selectively blocking the rapid component of the delayed rectifier outward potassium current. There is a dose-dependent increase in the QT interval and the corrected QT interval (QTc). Because of this, many practitioners will initiate dofetilide therapy only on individuals under telemetry monitoring or if serial EKG measurements of QT and QTc can be performed.

Sotalol is a non-selective competitive beta-adrenergic receptor blocker that also exhibits Class III antiarrhythmic properties. The U.S. Food and Drug Administration advises that sotalol only be used for serious arrhythmias, because its prolongation of the QT interval carries a small risk of life-threatening torsade de pointes. Sotalol also acts on potassium channels and causes a delay in relaxation of the ventricles. By blocking these potassium channels, sotalol inhibits efflux of K+ ions, which results in an increase in the time before another electrical signal can be generated in ventricular myocytes. This increase in the period before a new signal for contraction is generated.

Ibutilide is a Class III antiarrhythmic agent that is indicated for acute cardioconversion of atrial fibrillation and atrial flutter and prolongs action potential and refractory period of myocardial cells. Because of its Class III antiarrhythmic activity, there should not be concomitant administration of Class Ia and Class III agents. Unlike most other Class III antiarrhythmic drugs, ibutilide does not produce its prolongation of action potential via blockade of cardiac delayed rectifier of potassium current, nor does it have a sodium-blocking, antiadrenergic, and calcium blocking activity that other Class III agents possess. Thus, it is often referred as a "pure" Class III antiarrhythmic drug. Ibutilide, like other class III antiarrhythmic drugs, blocks delayed rectified potassium current. It does have action on the slow sodium channel and promotes the influx of sodium through these slow channels. Like other antiarrhythmics, ibutilide can lead to abnormal heart rhythms due to its ability to prolong the QT interval, which can lead to the potentially fatal abnormal heart rhythm known as torsades de pointes. The drug is contraindicated in patients that are likely to develop abnormal heart rhythms; persons that have had polymorphic ventricular tachycardia in the past, have a long QT interval, sick sinus syndrome, or a recent myocardial infarction, among others.

Dopamine receptor antagonists. A dopamine antagonist (antidopaminergic) is a type of drug that blocks dopamine receptors by receptor antagonism. Most antipsychotics are dopamine antagonists, and as such they have found use in treating schizophrenia, bipolar disorder, and stimulant psychosis. Several other dopamine antagonists are antiemetics used in the treatment of nausea and vomiting.

Droperidol is an antidopaminergic butyrophenone, used as an antiemetic and antipsychotic, and is a potent D2 (dopamine receptor) antagonist with some histamine and serotonin antagonist activity. There are concerns about QT prolongation and torsades de pointes. The evidence for this is disputed, with 9 reported cases of torsades in 30 years and all of those having received doses in excess of 5 mg. QT prolongation is a dose-related effect, and it appears that droperidol is not a significant risk in low doses, however, prolongation of QT interval leads to torsades de pointes.

Domperidone is a peripherally selective dopamine D2 receptor antagonist that is a drug useful in Parkinson's disease, caution is needed due to the cardiotoxic side effects of domperidone especially when given intravenously, in elderly people and in high doses (>30 mg per day). A clinical sign of domperidone's potential toxicity to the heart is the prolongation (lengthening) of the QT interval (a segment of the heart's electrical pattern). Domperidone use is associated with an increased risk of sudden cardiac death (by 70%) most likely through its prolonging effect of the cardiac QT interval and ventricular arrhythmias. The cause is thought to be blockade of hERG voltage-gated potassium channels. The risks are dose-dependent, and appear to be greatest with high/very high doses via intravenous administration and in the elderly, as well as with drugs that interact with domperidone and increase its circulating concentrations (namely CYP3A4 inhibitors). Conflicting reports exist, however. In neonates and infants, QT prolongation is controversial and uncertain.

Anticancer agents. Doxorubicin and anthracycline prolongation of QTc, increased QT dispersion and development of late potentials are indicative of doxorubicin-induced abnormal ventricular depolarization and repolarization. QT dispersion and late potentials are both known to be associated with increased risk of serious ventricular dysrhythmias and sudden death in various cardiac diseases.

Arsenic trioxide is an anti-leukemic can prolong the QTc interval. Cardiac Conduction Abnormalities: Before initiating therapy, perform a 12-lead ECG, assess serum electrolytes and creatinine, correct preexisting electrolyte abnormalities, and consider discontinuing drugs known to prolong QT interval. Arsenic trioxide can cause QT interval prolongation and complete atrioventricular block. QT prolongation can lead to a torsade de pointes-type ventricular arrhythmia, which can be fatal. The risk of torsade de pointes is related to the extent of QT prolongation, concomitant administration of QT prolonging drugs, a history of torsade de pointes, preexisting QT interval prolongation, congestive heart failure, administration of potassium-wasting diuretics, or other conditions that result in hypokalemia or hypomagnesemia. One patient (also receiving amphotericin B) had torsade de pointes during induction therapy for relapsed APL with arsenic trioxide. Arsenic trioxide ($As_2O_3$) used in the treatment of acute promyelocytic leukemia reduced hERG/IKr currents not by direct block, but by inhibiting the processing of hERG protein in the endoplasmic reticulum (ER) thereby decreasing surface expression of hERG.

Opioids. Levomethadyl is a levo isomer of α-methadyl acetatea synthetic opioid similar in structure to methadone. It has a long duration of action due to its active metabolites. In 2001, levacetylmethadol was removed from the European market due to reports of life-threatening ventricular rhythm disorders.

Methadone is an opioid used to treat pain and drug addiction. Serious risks include opioid abuse and heart arrhythmia may also occur including prolonged QT. The number of deaths in the United States involving methadone poisoning was 4,418 in 2011, which was 26% of total deaths from opioid poisoning.

Hypolipidemic agents. Lovostatin is a drug used for lowering cholesterol an inhibitor of 3-hydroxy-3-methylglutaryl-coenzyme A reductase (HMG-CoA reductase), an enzyme that catalyzes the conversion of HMG-CoA to mevalonate. Mevalonate is a required building block for cholesterol biosynthesis and lovastatin interferes with its production by acting as a reversible competitive inhibitor for HMG-CoA, which binds to the HMG-CoA reductase. QTc prolongation associated with antipsychotic medication occurs in a dose-dependent manner. The addition of lovastatin causes an increase in plasma quetiapine levels through competitive inhibition of the cytochrome P(450) (CYP) isoenzyme 3A4. This highlights the potential for a drug interaction between quetiapine and lovastatin leading to QTc prolongation during the management of dysipidemia in patients with schizophrenia.

Probucol is an anti-hyperlipidemic drug initially developed in the treatment of coronary artery disease. Probucol is associated with QT interval prolongation. Probucol aggravates long QT syndrome associated with a novel missense mutation M124T in the N-terminus of HERG.

Channelopathies. The human ether-a-go-go gene related cardiac tetrameric potassium channel, when mutated, can render patients sensitive to over 163 drugs, which inhibit ion conduction and deregulate action potentials. Prolongation of the action potential follows effects in the potassium channel. Ion channel active drugs may directly increase the QTc interval, and increase the risk of torsade de point and sudden cardiac death. Exacerbation of cardiomyocyte potassium channel sensitivity to drugs may also be associated with metabolic diseased states including diabetes or may be of idiopathic origin.

As used herein, the term "liposome" refers to a capsule wherein the wall or membrane thereof is formed of one or more of the novel lipids of the present invention. The lipids of the present invention can be used alone or in conjunction with other, known lipids. In one specific non-limiting example the novel lipids form, or are used in, liposomes that are empty liposomes and can be formulated from a single type of phospholipid or combinations of phospholipids. The empty liposomes can further includes one or more surface modifications, such as proteins, carbohydrates, glycolipids or glycoproteins, and even nucleic acids such as aptamers, thio-modified nucleic acids, protein nucleic acid mimics, protein mimics, stealthing agents, etc. In one embodiment, the novel liposome or novel liposome precursor comprising a novel lipid-monoglyceride-fatty acid eutectic, such as a eutectic that includes: lysophosphatidyl compound, a monoglyceride, and free fatty acid, and in certain aspects the ratios of the composition are 1:4:2, 1:3:3, 2:4:2, or 1:2:4 mole percent novel lipid:monoglyceride:free fatty acid. The composition may comprise a eutectic mixture comprising a novel lipid, a myristoyl monoglyceride, and a myristic acid. In one specific, non-limiting example the composition also comprises an active agent in or about the novel lipid liposome, which can be an empty liposome, and the composition has a ratio of phospholipids to active agent of 3:1, 1:1, 0.3:1, and 0.1:1.

Prior work from the some of the present inventors has demonstrated that formulation with a liposome containing 1,2-Dimyristoyl-sn-glycero-3-phosphorylcholine (DMPC), 1,2-Dimyristoyl-sn-glycero-3-phosphorylglycerol (DMPG), DMPC/DMPG, 1-Myristoyl-2-Hydroxy-sn-Glycero-3-Phosphocholine, 12-Mysteroyl-2-Hydroxy-sn-Glycero-3-[Phospho-rac-(glycerol)], 1-myristoyl-2-hydroxy-sn-glycero-3-phospho-(1'-rac-glycerol) (LysoPG), 12-Mysteroyl-2-Hydroxy-sn-Glycero-3-[Phospho-rac-(glycerol)], 1-myristoyl-2-hydroxy-sn-glycero-3-phospho-(1'-rac-glycerol) (LysoPG), or 1-myristoyl-2-hydroxy-sn-glycero-3-phosphocholine (LysoPC), lysophosphatidylcholine, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine or erucoyl-lysophosphatidylcholine, prevented hERG channel inhibition by a variety of QT prolonging agents.

More than 20 QTc-prolonging drugs have had their QTc prolongation eliminated in various regulatory-validated preclinical models using the above lipids.

The present invention demonstrates an enhanced effect in reducing, or eliminating, QT prolongation in a guinea pig model system. The guinea pig model system used herein is the closes model system to the functioning of the human heart and is well-accepted for testing of QT prolonging agents. Briefly, guinea pigs were instrumented with ECG leads, and administered increasing oral doses of moxifloxacin. Guinea pigs are the preferred species in Europe and Canada for QT prolongation testing, because they possess a complement of cardiac ion channels most similar to that of humans, and are exquisitely sensitive to proarrhythmic drugs. On the drug side, Moxifloxacin is the preferred QTc-prolonging positive control drug in Thorough QT (TQT) clinical studies because it causes a dose-dependent QTc prolongation in all species, and exhibits very linear pharmacokinetics, making it easy to dose and relatively safe at sub-toxic exposure levels.

Those guinea pigs administered only moxifloxacin exhibited severe (+10 ms) and life-threatening (+30 ms) QTc prolongation. In contrast, those animals that had received a concomitant dose of, as an example, 14:0 lyso PG, exhibited no, or very little, changes in QTc. There resulted a statistically significant right-shift in the QTc-dose response of Moxifloxacin, actually preventing the QTc prolongation from becoming dose-limiting.

AV block represents an interesting conundrum in cardiology: drug-induced AV block patients are not treated by pacemaker implantation, unlike patients suffering from disease-induced AV block. Yet, there is evidence that drug-induced AV block is irreversible after drug discontinuation in 56% of cases (Zeltser D, Justo D, Halkin A, et al. Drug-induced atrioventricular block: prognosis after discontinuation of the culprit drug. J Am Coll Cardiol. 2004; 44(1):105-108). Current practice is to immediately discontinue AV blocking drugs upon discovering the effect. This withdraws useful, efficient drugs from the pharmacopeia available to oncologists, while directly impacting drug adoption in the clinic.

The ionic channels involved in AV block and QTc prolongation are completely distinct: sodium ($Na^+$) and calcium ($Ca^{2+}$) channel inhibition are responsible for the onset of AV block, while delays in repolarization due to potassium ($K^+$) inhibition lead to QTc prolongation. Yet, the hypothesized mechanism by which lipids rescues $K^+$ currents could also benefit $Na^+$ and $Ca^{2+}$ currents.

To test this hypothesis, guinea pigs were instrumented (subcutaneous ECG leads) and exposed to increasing intravenous doses of Fingolimod and/or verapamil, without and with an oral dose of 14:0 lyso PG. ECG signals were recorded continuously for 2 hours post-dose for the AV blockers Fingolimod and verapamil. PR intervals were measured following the infusion of Fingolimod. Measurements of PR were stopped when the P wave disconnected from the QRS complexes, indicating 3rd degree AV block.

Guinea pigs exposed to an intravenous infusion of Fingolimod alone transitioned to 1st degree AV block as of a dose of 15 µg/kg, which rapidly progressed to a Mobitz Type-1, 2nd-degree AV block at 20 µg/kg, and finally progressed to 3rd degree AV block as of a dose of 23 µg/kg. The progression of the AV block was rapid and irreversible: stopping infusion did not prevent the onset of P-QRS dissociation.

The cohort of guinea pigs exposed to verapamil received an i.v. injection of 0.5 mg/kg, followed 60 minutes later by an intravenous infusion of Fingolimod. A 1st-degree AV block appeared at a dose of 7 µg/kg, changed to a Mobitz-Type-1 2nd degree AV block at 10 µg/kg, and transitioned to 3rd-degree dissociation between P waves and QRS complexes as of 45 µg/kg.

The third cohort of animals received an initial oral gavage of 1.0 mg/kg 14:0 lyso PG, followed 60 minutes later by an intravenous dose of 0.5 mg/kg verapamil. Sixty (60) minutes post-verapamil, Fingolimod was infused into the animals as described above. The animals exhibited modest changes in PR intervals up to a dose of 200 µ/kg, at which point a Is-degree AV block appeared. A Mobitz-Type-2 AV block appeared in 2 out of 6 animals with P-QRS dissociation observed at a dose of 51 µg/kg in those two animals, and at 300 µg/kg in the rest of the animals in the cohort.

In human patients, Fingolimod is counter-indicated in patients presenting a history of Mobitz Type II second-degree or third-degree AV block or sick sinus syndrome. The drug has been shown to produce AV block from the first dose, and avoiding treatment with Fingolimod and AV blockers is recommended (Fingolimod (Fingolimod) Full Prescribing Information. Novartis: T2016-22, February 2016). Given the history of translatability of the guinea pig cardiovascular data to other species, including man, these results suggest that 14:0 lyso PG could alleviate the risk of AV block associated with Fingolimod use, thus enhancing the safety profile of the drug, and allowing the treatment of patients, which cannot otherwise receive Fingolimod due to AV block issues.

FIG. 1 is a graph that shows the effect of an oral single dose of Moxifloxacin (20 mg/kg) on QTc interval of guinea pigs compared to the same oral single dose of Moxifloxacin administrated concomitantly with an oral single dose of Compound 1.

Figure 2:
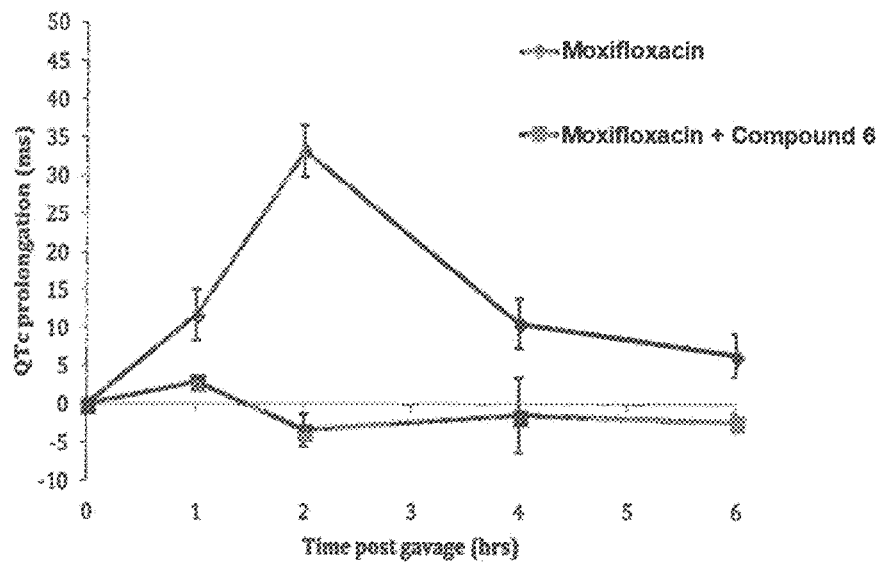
FIG. 2 is a graph that shows the effect of an oral single dose of Moxifloxacin (20 mg/kg) on QTc interval of guinea pigs compared to the same oral single dose of Moxifloxacin administrated concomitantly with an oral single dose of Compound 6.

FIG. 2 is a graph that shows the effect of an oral single dose of Moxifloxacin (20 mg/kg) on QTc interval of guinea pigs compared to the same oral single dose of Moxifloxacin administrated concomitantly with an oral single dose of Compound 6.

Figure 3:
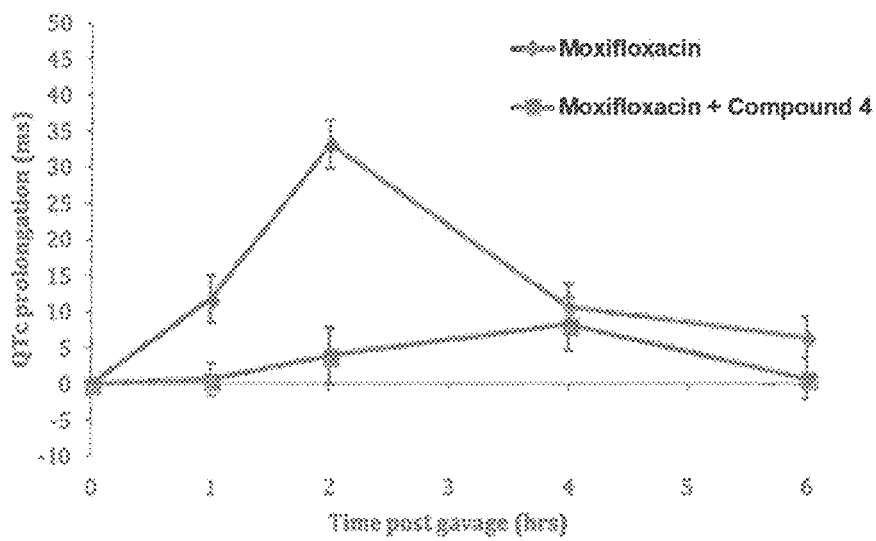
FIG. 3 is a graph that shows the effect of an oral single dose of Moxifloxacin (20 mg/kg) on QTc interval of guinea pigs compared to the same oral single dose of Moxifloxacin administrated concomitantly with an oral single dose of Compound 4.

FIG. 3 is a graph that shows the effect of an oral single dose of Moxifloxacin (20 mg/kg) on QTc interval of guinea pigs compared to the same oral single dose of Moxifloxacin administrated concomitantly with an oral single dose of Compound 4.

Figure 4:
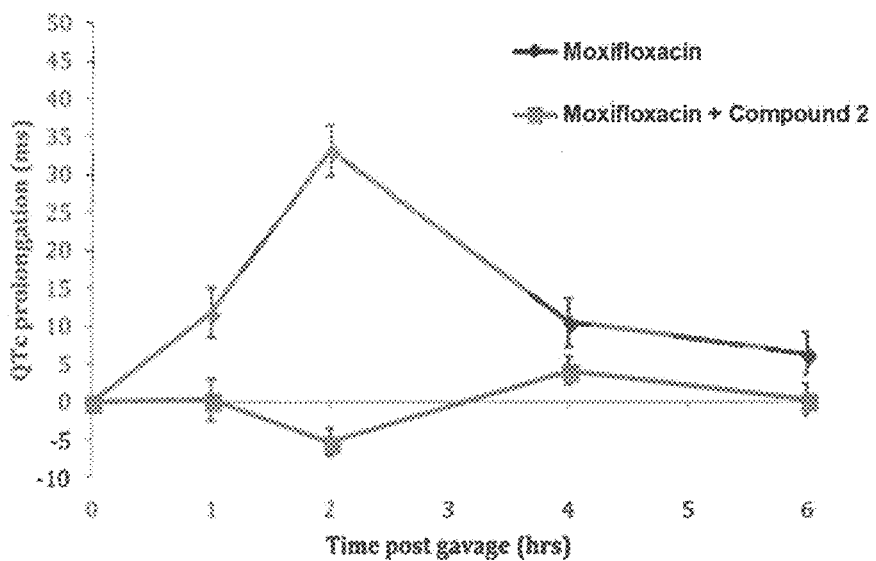
FIG. 4 is a graph that shows the effect of an oral single dose of Moxifloxacin (20 mg/kg) on QTc interval of guinea pigs compared to the same oral single dose of Moxifloxacin administrated concomitantly with an oral single dose of Compound 2

FIG. 4 is a graph that shows the effect of an oral single dose of Moxifloxacin (20 mg/kg) on QTc interval of guinea pigs compared to the same oral single dose of Moxifloxacin administrated concomitantly with an oral single dose of Compound 2.

Figure 5:
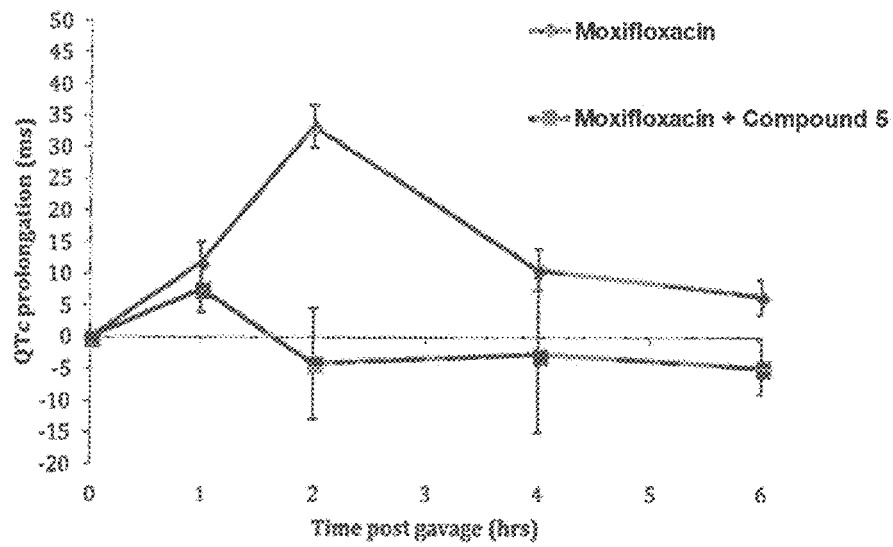
FIG. 5 is a graph that shows the effect of an oral single dose of Moxifloxacin (20 mg/kg) on QTc interval of guinea pigs compared to the same oral single dose of Moxifloxacin administrated concomitantly with an oral single dose of Compound 5.

FIG. 5 is a graph that shows the effect of an oral single dose of Moxifloxacin (20 mg/kg) on QTc interval of guinea pigs compared to the same oral single dose of Moxifloxacin administrated concomitantly with an oral single dose of Compound 5.

Figure 6:
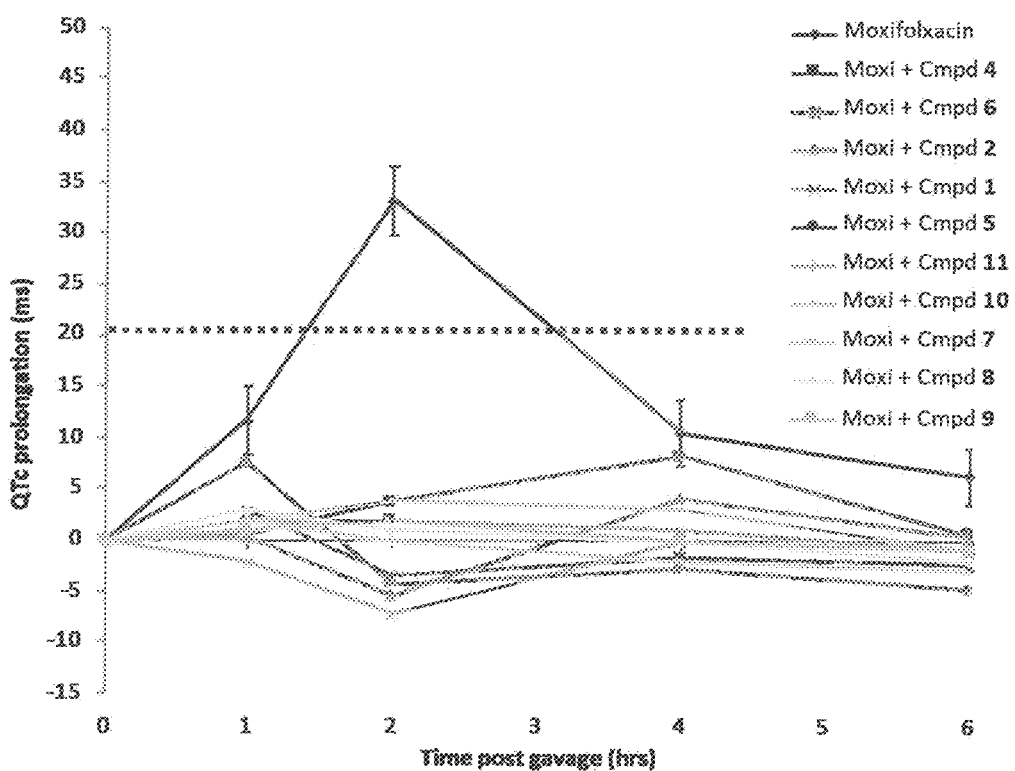
FIG. 6 is a composite graph that shows the effect of an oral single dose of Moxifloxacin (20 mg/kg) on QTc interval of guinea pigs compared to the same oral single dose of Moxifloxacin administrated concomitantly with an oral single dose of Compound 1, Compound 2, Compound 4, Compound 5, Compound 6, Compound 7, Compound 8, Compound 9, Compound 10 and Compound 11.

FIG. 6 is a composite graph that shows the effect of an oral single dose of Moxifloxacin (20 mg/kg) on QTc interval of guinea pigs compared to the same oral single dose of Moxifloxacin administrated concomitantly with an oral single dose of Compound 1, Compound 2, Compound 4, Compound 5, Compound 6, Compound 7, Compound 8, Compound 9, Compound 10 and Compound 11.

Figure 7:
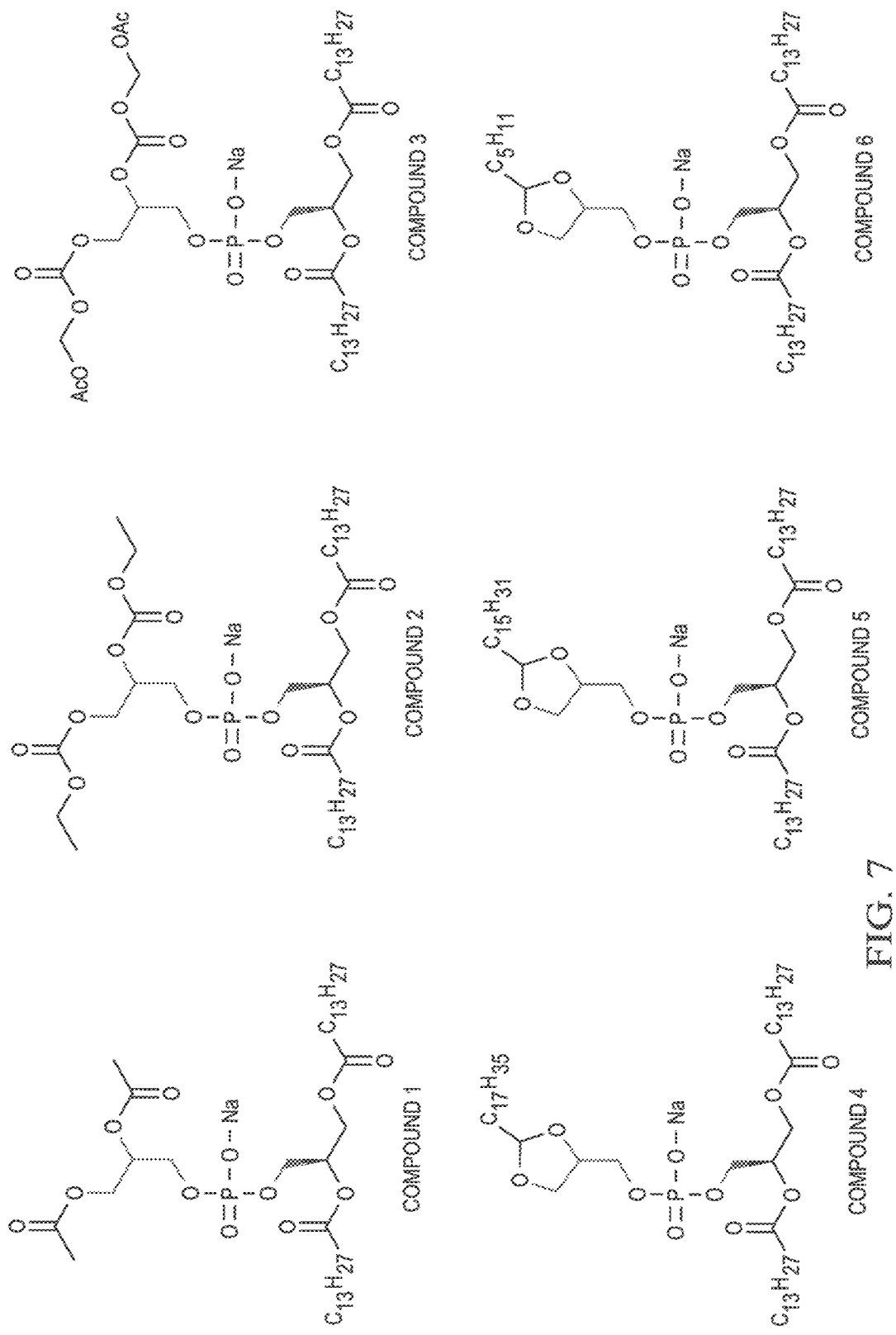
FIG. 7 is a depiction of example chemical structures that are embodiments of the present invention.
Figure 7:
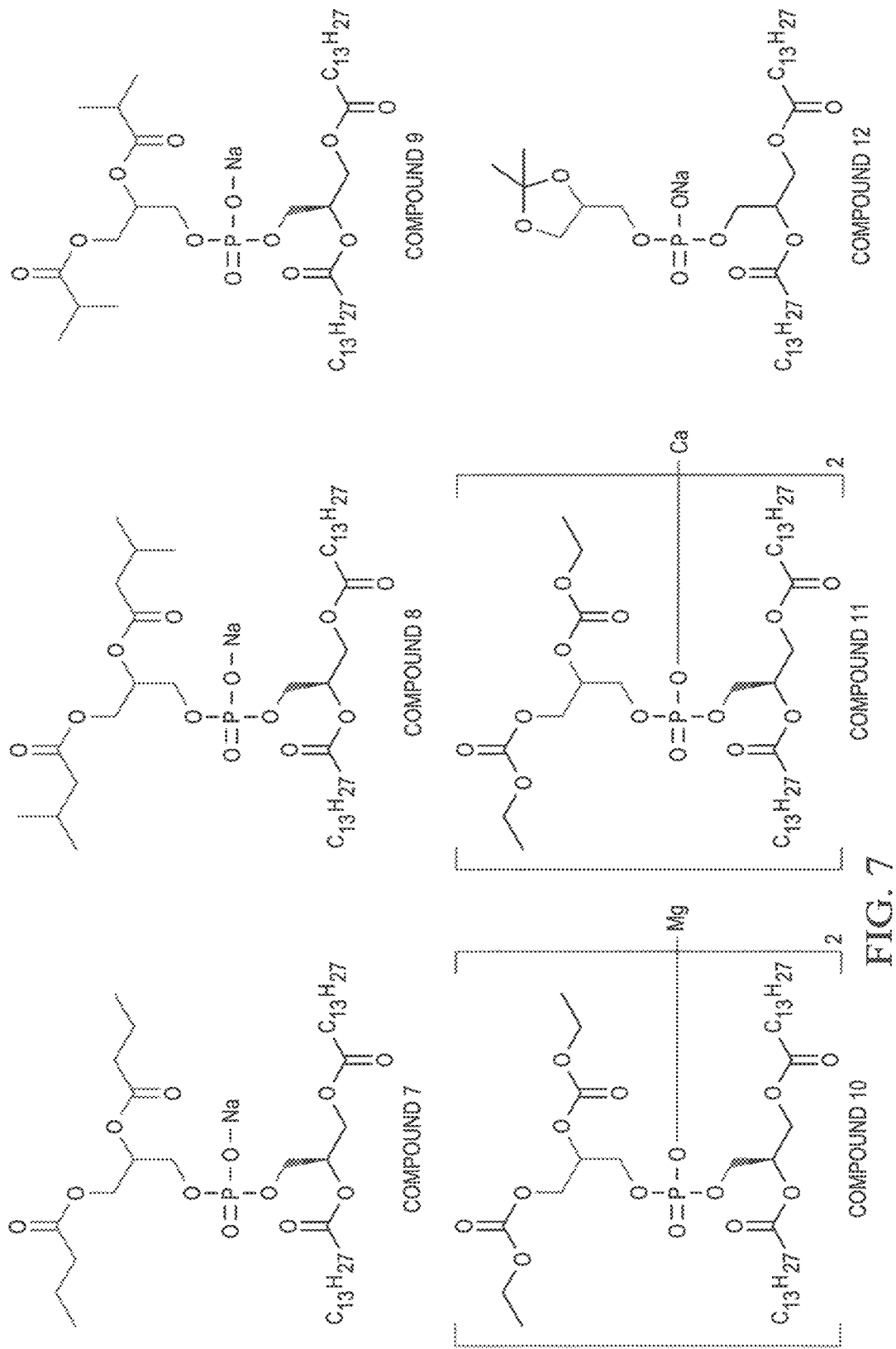
Figure 7:
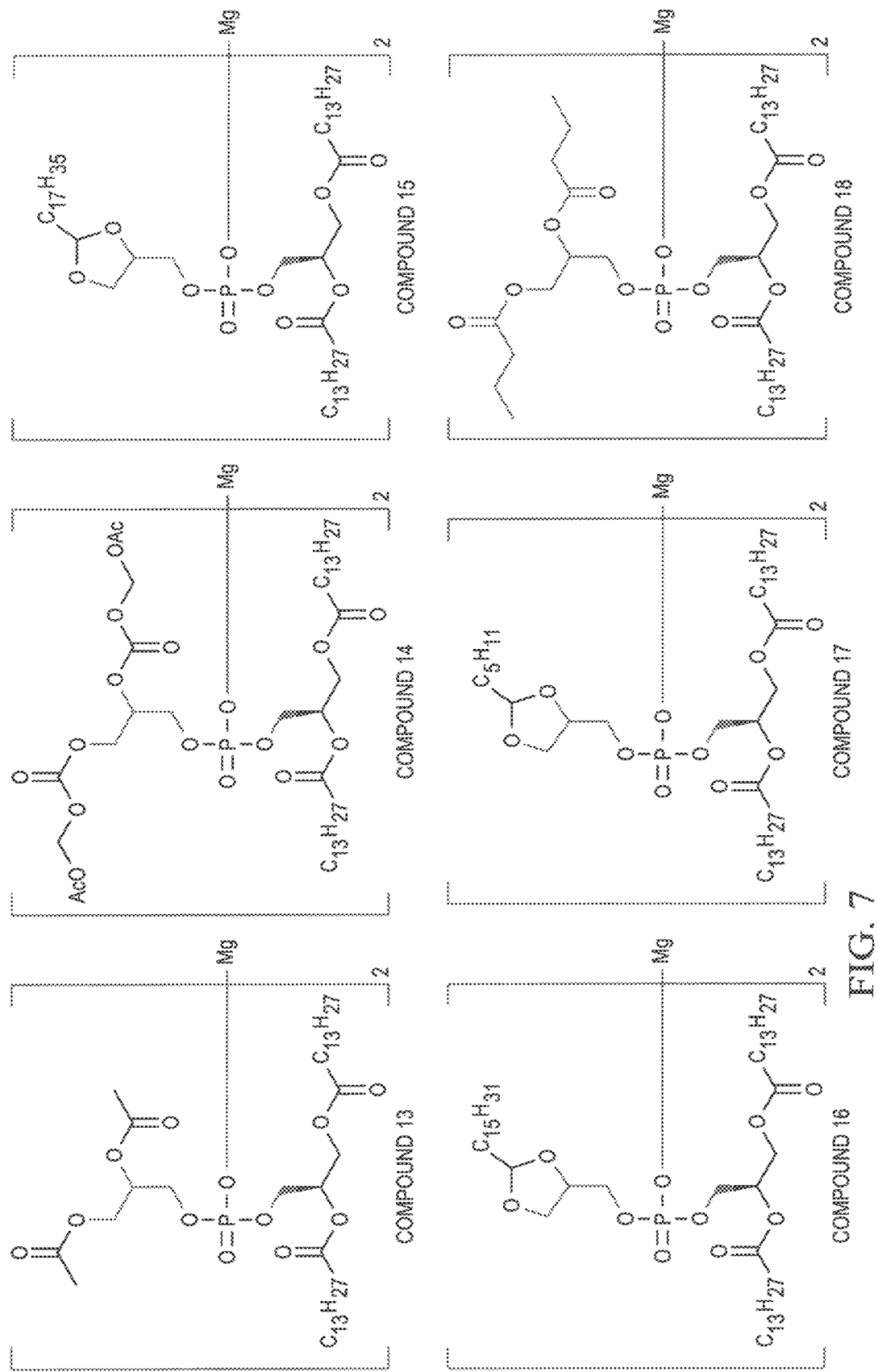
Figure 7:
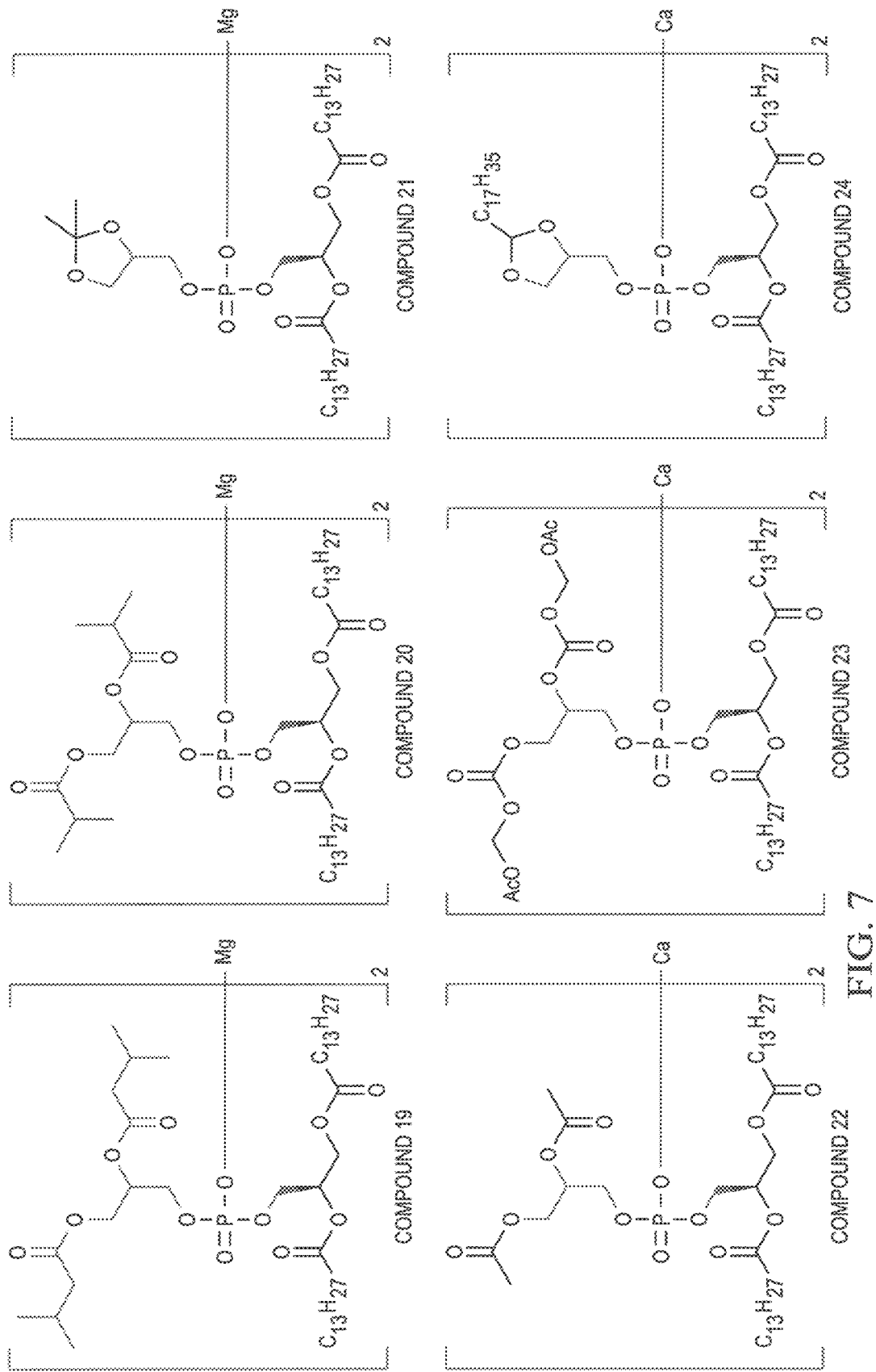
Figure 7:
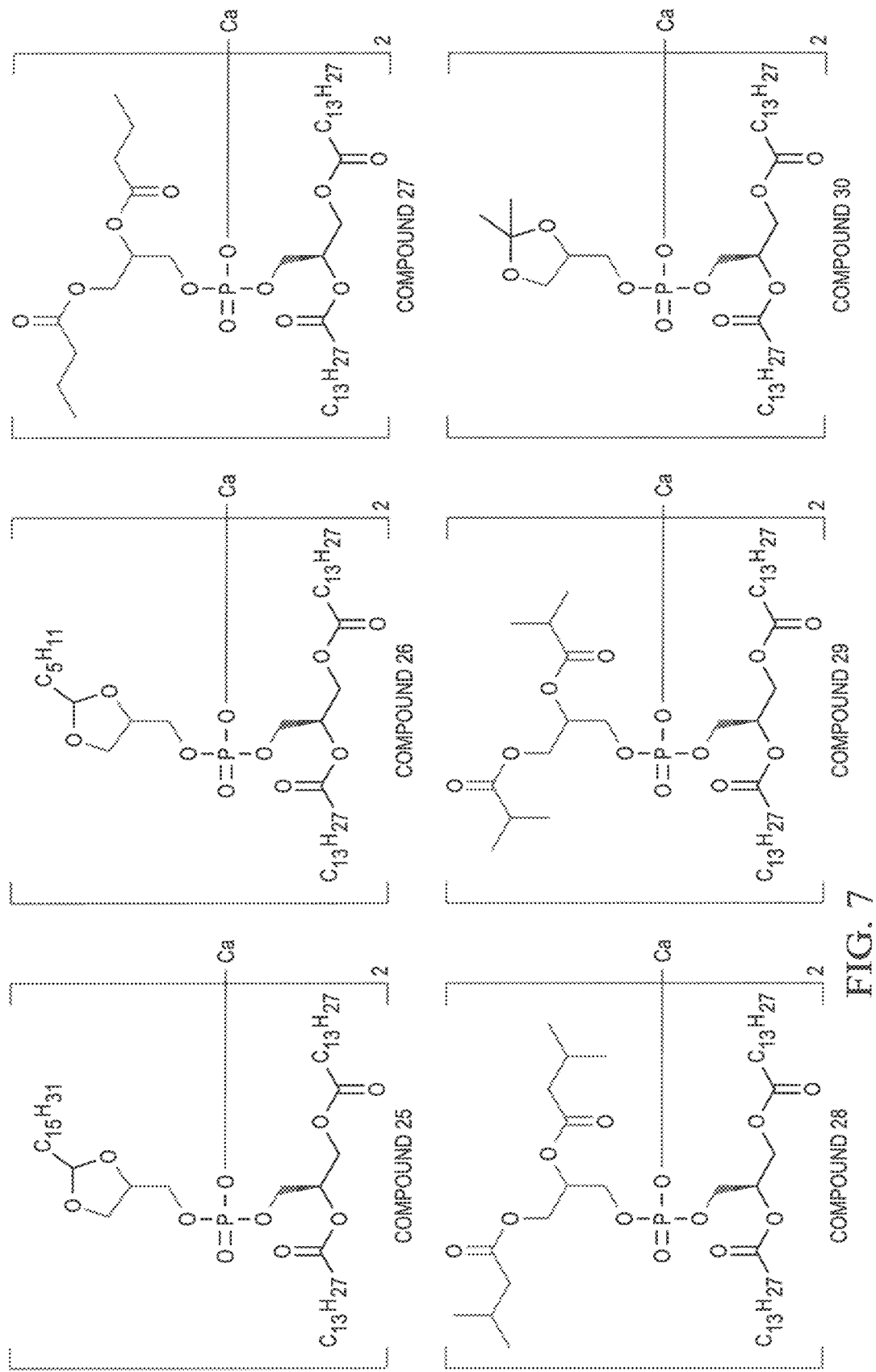

FIG. 7 is a depiction of example chemical structures which are embodiments of the present invention.

The novel lipids of the present invention may be manufactured in a native form, or in the form of a salt, hydrate, or solvate thereof salt. Salts further include, by way of example only, lithium, sodium, potassium, calcium, magnesium, ammonium, tetraalkylammonium, and the like.

In at least some embodiments of the present invention, compounds of Formula I are prepared according to the following schemes. For reference, all variable groups included in the following schemes relate to the corresponding variables defined generally above. One of ordinary skill in the art will recognize that alternative reagents and reactants can be used to generate the same target compounds and intermediates.

As illustrated in Scheme 1, compounds of Formula VI are reacted with anhydrides followed by subsequent salt formation giving compounds of Formula VII One of ordinary skill in the art will recognize that alternatives to anhydrides will produce similar results. Such alternatives include, but are not limited to, acid chlorides, acyl imidazoles, acyl succinimides and the like. Additionally, one of ordinary skill in the art will recognize that carboxylic acids in the presence of activating agents will produce similar results. Suitable activating agents include, but are not limited to, DCC, EDC, HBTU, BOP, PyBOP, carbonyl diimidazole, disuccinimidyl carbonate and the like. One of ordinary skill in the art will recognize that alternatives to DOWEX Na$^+$ resin for salt formation are useful. Such alternatives include, but are not limited to, sodium bicarbonate, sodium carbonate and the like. One of ordinary skill in the art will recognize that compounds of Formula VII include compounds 1, 7, 8 and 9.

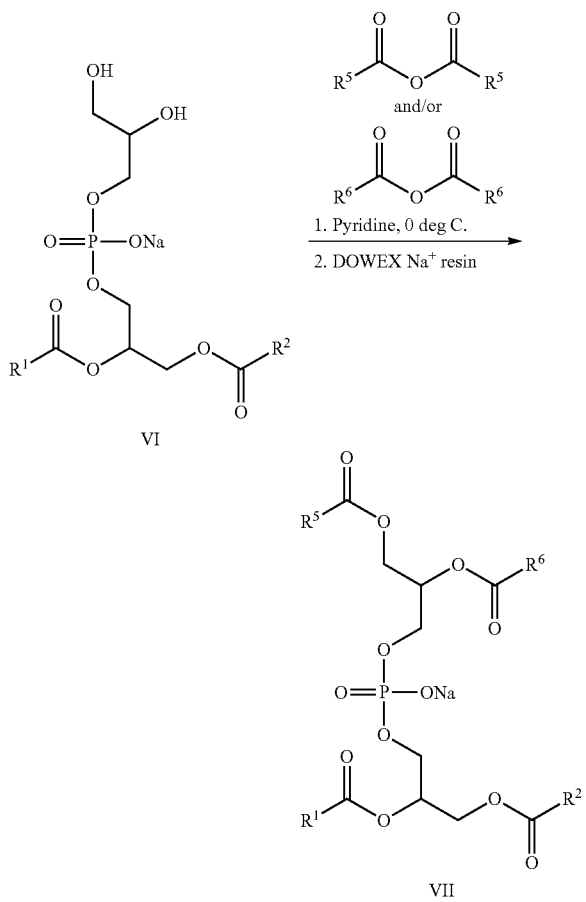

As illustrated in Scheme 2, compounds of Formula VI are reacted with chloroformates followed by subsequent salt formation giving compounds of Formula VIII. One of ordinary skill in the art will recognize that alternatives to chloroformates will produce similar results. Such alternatives include, but are not limited to, pyrocarbonates and the like. One of ordinary skill in the art will recognize that bases other than triethylamine are useful in carbonate formation reactions. Such bases include, but are not limited to, triisopropylamine, diisopropylethylamine, DBU, N-methylmorpholine, N-methylpyridine, N,N-dimethylpiperazine and the like. One of ordinary skill in the art will recognize that acyl transfer catalysts other than DMAP are useful in carbonate formation reactions. Such acyl transfer catalysts include, but are not limited to, pyridine, 2-methylpyridine and the like. Additionally, one of ordinary skill in the art will recognize that introduction of Lewis acid catalysts may facilitate carbonate formation. Such Lewis acid catalysts include, but are not limited to, zinc chloride, zinc acetate, zinc bromide, aluminum trichloride, titanium trichloride, titanium isopropoxide, boron trifluoride, tin chloride, alumina, silica gel and the like. One of ordinary skill in the art will recognize that alternatives to sodium bicarbonate for salt formation are useful. Such alternatives include, but are not limited to, DOWEX Na+ resin, sodium carbonate and the like. One of ordinary skill in the art will recognize that compounds of Formula VIII include compounds 2 and 3.

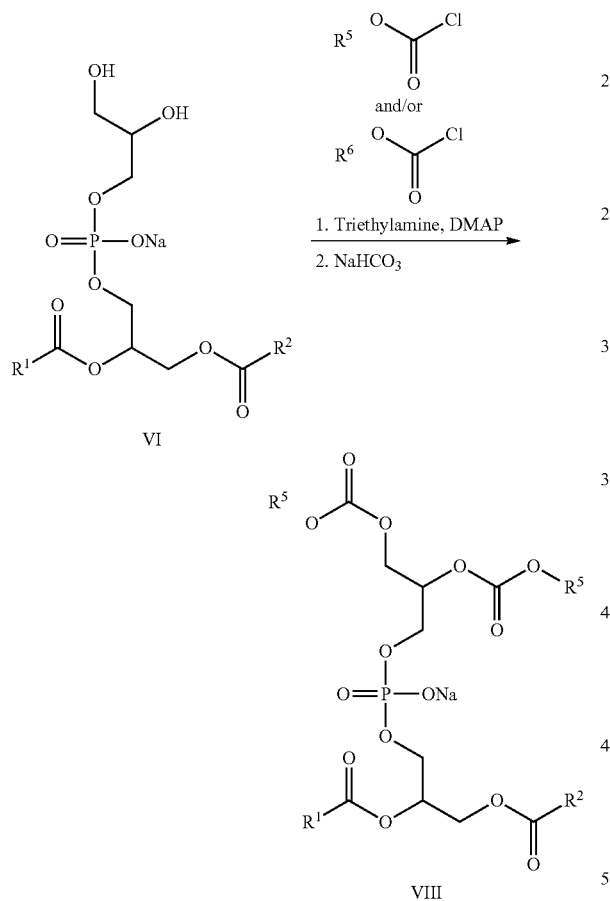

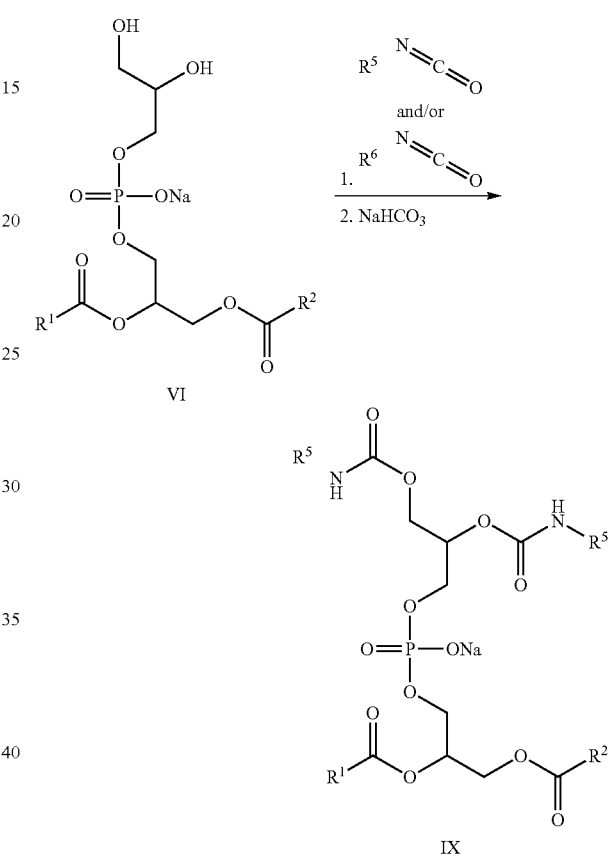

As illustrated in Scheme 3, compounds of Formula VI are reacted with isocyanates followed by subsequent salt formation giving compounds of Formula IX. One of ordinary skill in the art will recognize that alternatives to isocyanates will produce similar results. One of ordinary skill in the art will recognize that bases can facilitate carbamate formation. Such bases include, but are not limited to, triethylamine, triisopropylamine, diisopropylethylamine, DBU, N-methylmorpholine, N-methylpyridine, N,N-dimethylpiperazine and the like. One of ordinary skill in the art will recognize that acyl transfer catalysts can facilitate carbamate formation. Such acyl transfer catalysts include, but are not limited to, DMAP, pyridine, 2-methylpyridine and the like. Additionally, one of ordinary skill in the art will recognize that introduction of Lewis acid catalysts may facilitate carbamate formation. Such Lewis acid catalysts include, but are not limited to, zinc chloride, zinc acetate, zinc bromide, aluminum trichloride, titanium trichloride, titanium isopropoxide, boron trifluoride, tin chloride, alumina, silica gel and the like. One of ordinary skill in the art will recognize that alternatives to sodium bicarbonate for salt formation are useful. Such alternatives include, but are not limited to, DOWEX Na+ resin, sodium carbonate and the like.

As illustrated in Scheme 4, compounds of Formula X are reacted with anhydrides, chloroformates or isocyanates followed by subsequent cleavage of the benzyl ether protecting group giving compounds of Formula XI. Coupling of compounds of Formula XI with compounds of Formula XII using Phospholipase D generates compounds of Formula XIII. One of ordinary skill in the art will recognize that for compounds of Formula IX alternatives to anhydrides will produce similar results. Such alternatives include, but are not limited to, acid chlorides, acyl imidazoles, acyl succinimides and the like. Additionally, one of ordinary skill in the art will recognize that for compounds of Formula IX carboxylic acids in the presence of activating agents will produce similar results. Suitable activating agents include, but are not limited to, DCC, EDC, HBTU, BOP, PyBOP, carbonyl diimidazole, disuccinimidyl carbonate and the like. One of ordinary skill in the art will recognize that for compounds of Formula IX alternatives to chloroformates will produce similar results. Such alternatives include, but are not limited to, pyrocarbonates and the like. One of ordinary skill in the art will recognize that for compounds of Formula IX alternatives to isocyanates will produce similar results. One of ordinary skill in the art will recognize that bases can facilitate ester, carbonate and carbamate formation. Such bases include, but are not limited to, triethylamine, triisopropylamine, diisopropylethylamine, DBU, N-methylmorpholine, N-methylpyridine, N,N-dimethylpiperazine and the like. One of ordinary skill in the art will recognize that acyl transfer catalysts can facilitate ester, carbonate and carbamate formation. Such acyl transfer catalysts include, but are not limited to, DMAP, pyridine, 2-methylpyridine and the like. Additionally, one of ordinary skill in the art will recognize that introduction of Lewis acid catalysts may facilitate ester, carbonate and carbamate formation. Such Lewis acid catalysts include, but are not limited to, zinc chloride, zinc acetate, zinc bromide, aluminum trichloride, titanium trichloride, titanium isopropoxide, boron trifluoride, tin chloride, alumina, silica gel and the like. One of ordinary skill in the art will recognize that alternatives to the benzyl ether protecting group, and associated reaction conditions for their cleavage, are useful. Various appropriate alcohol protecting groups are broadly described in "Green's *Protective Groups in Organic Synthesis*". Such benzyl ether alternatives include, but are not limited to, trimethylsilyl ethers, tert-butyl dimethylsilyl ethers, triisopropylsilyl ethers, tert-butyl diphenylsilyl ethers, acetates, benzoates, 4-nitrobenzoates, tert-butyl ethers, 4-methoxybenzyl ethers and the like. One of ordinary skill in the art will recognize that alternative enzyme and alternate enzyme reaction conditions are useful in the enzymatic formation of phospho diesters. One of ordinary skill in the art will recognize that compounds of Formula XIII include compounds 1, 2, 3, 7, 8 and 9.

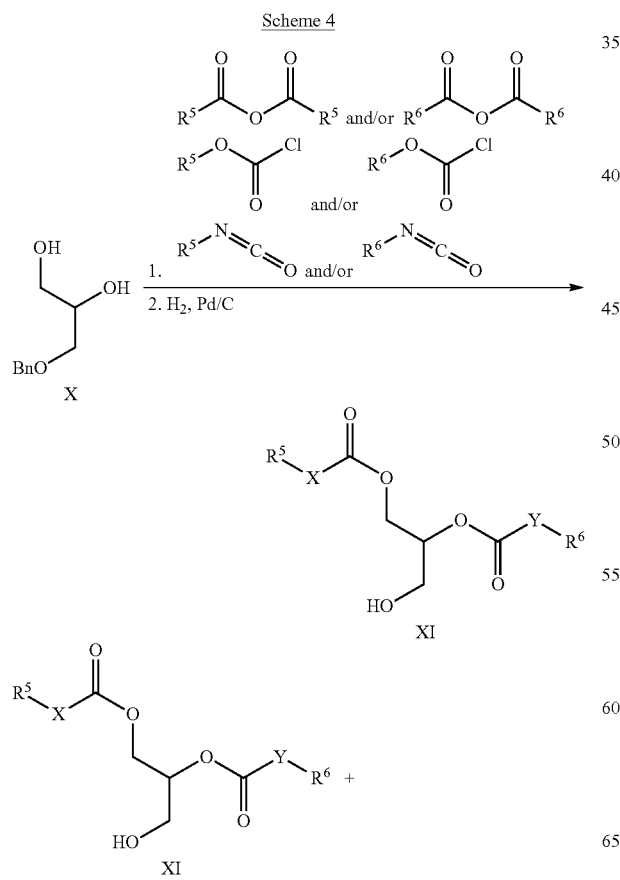

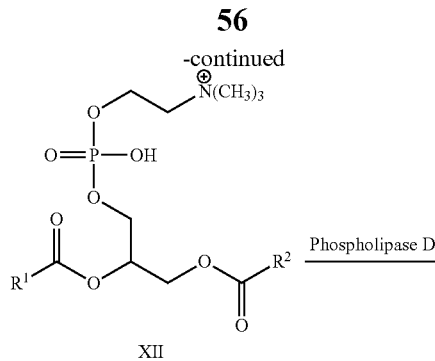

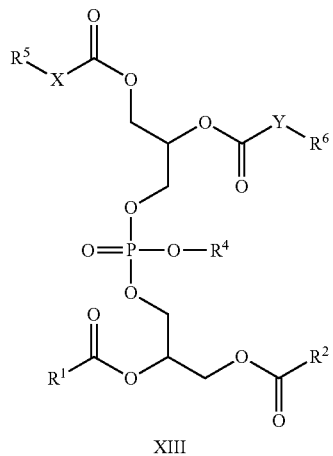

As illustrated in Scheme 5, compounds of Formula VI are reacted with acetals, ketals, aldehydes or ketones in the presence of an acid catalyst followed by subsequent salt formation giving compounds of Formula XIV. One of ordinary skill in the art will recognize that alternatives to acetals, ketals, aldehydes or ketones will produce similar results. Such alternatives include, but are not limited to, vinyl ethers and the like. Additionally, one of ordinary skill in the art will recognize that while p-toluenesulfonic acid is an appropriate acid catalyst for the formation of acetals and ketals, alternative acid catalysts are also useful. Such alternatives to p-toluenesulfonic acid include, but are not limited to, PPTS, sulfuric acid, methanesulfonic acid, Amberlyst resin, DOWEX acid resin, silica gel and the like. Furthermore, one of ordinary skill in the art will recognize that a compound of Formula XIV can be converted into an alternate compound of Formula XIV on reaction with an alternate acetal, ketal, aldehyde or ketone in the presence of an acid catalyst. One of ordinary skill in the art will recognize that alternatives to DOWEX Na$^+$ resin for salt formation are useful. Such alternatives include, but are not limited to, sodium bicarbonate, sodium carbonate and the like. One of ordinary skill in the art will recognize that compounds of Formula XIV include compounds 4, 5, 6 and 12.

Scheme 5

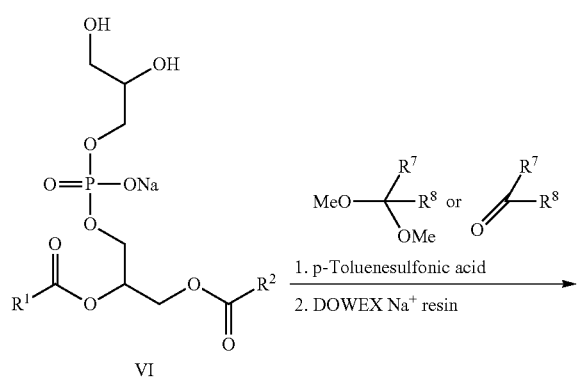

As illustrated in Scheme 6, compounds of Formula X are reacted with acetals, ketals, aldehydes or ketones in the presence of an acid catalyst followed by subsequent cleavage of the benzyl ether protecting group giving compounds of Formula XV. Coupling of compounds of Formula XV with compounds of Formula XII using Phospholipase D generates compounds of Formula XVI. One of ordinary skill in the art will recognize that for compounds of Formula XV alternatives to acetals, ketals, aldehydes or ketones will produce similar results. Such alternatives include, but are not limited to, vinyl ethers and the like. Additionally, one of ordinary skill in the art will recognize that while p-toluenesulfonic acid is an appropriate acid catalyst for the formation of acetals and ketals, alternative acid catalysts are also useful. Such alternatives to p-toluenesulfonic acid include, but are not limited to, PPTS, sulfuric acid, methanesulfonic acid, Amberlyst resin, DOWEX acid resin, silica gel and the like. Furthermore, one of ordinary skill in the art will recognize that a compound of Formula XV can be converted into an alternate compound of Formula XV on reaction with an alternate acetal, ketal, aldehyde or ketone in the presence of an acid catalyst. One of ordinary skill in the art will recognize that alternatives to the benzyl ether protecting group, and associated reaction conditions for their cleavage, are useful. Various appropriate alcohol protecting groups are broadly described in "Green's *Protective Groups in Organic Synthesis*". Such benzyl ether alternatives include, but are not limited to, trimethylsilyl ethers, tert-butyl dimethylsilyl ethers, triisopropylsilyl ethers, tert-butyl diphenylsilyl ethers, acetates, benzoates, 4-nitrobenzoates, tert-butyl ethers, 4-methoxybenzyl ethers and the like. One of ordinary skill in the art will recognize that alternative enzyme and alternate enzyme reaction conditions are useful in the enzymatic formation of phospho diesters. One of ordinary skill in the art will recognize that compounds of Formula XVI include compounds 4, 5, 6 and 12.

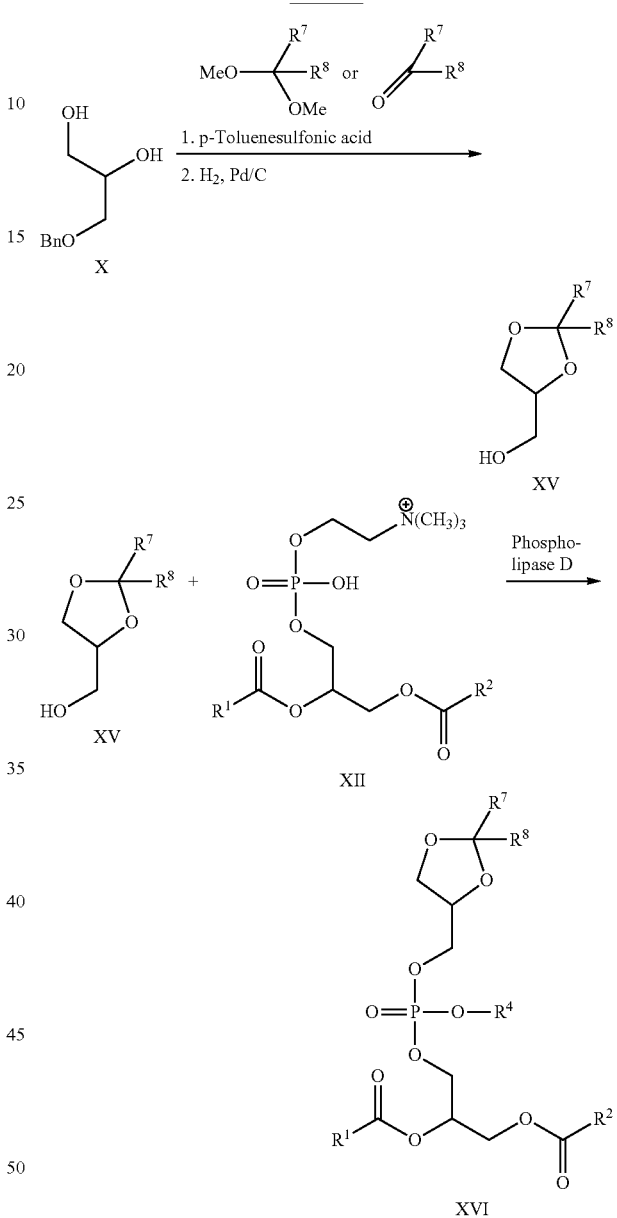

Scheme 7, Scheme 8, Scheme 9, Scheme 10 and Scheme 11 collectively illustrate preparation of compounds of Formula XXVII. As illustrated in Scheme 7, a compound of Formula XVII is converted to a benzyl ether giving a compound of Formula XVIII. The ketal of a compound of Formula XVIII is then cleaved giving a compound of Formula XIX. On reaction with one or more carboxylic acids and an appropriate activating reagent, a compound of Formula XIX is converted to a compound of Formula XX. Subsequent cleavage of the benzyl ether of a compound of Formula XX gives a compound of Formula XXI. One of ordinary skill in the art will recognize that alternate reagents and reaction conditions are useful for formation of a benzyl ether. One of ordinary skill in the art will also recognize that alternatives to the benzyl ether protecting group, and associated reaction conditions for their formation, are useful. Various appropriate alcohol protecting groups are broadly described in "Green's *Protective Groups in Organic Synthesis*". Such benzyl ether alternatives include, but are not limited to, trimethylsilyl ethers, tert-butyl dimethylsilyl ethers, triisopropylsilyl ethers, tert-butyl diphenylsilyl ethers, acetates, benzoates, 4-nitrobenzoates, tert-butyl ethers, 4-methoxybenzyl ethers and the like. Similarly, one of ordinary skill in the art will recognize that alternative reaction conditions are useful for the cleavage of acetals and ketals. Such conditions are generally described in Green's "*Protective Groups in Organic Synthesis*". One of ordinary skill in the art will recognize that carboxylic acids and associated activating agents are useful for the formation of esters. One of ordinary skill in the art will recognize that DCC is an appropriate activating agent for coupling of alcohols and carboxylic acids to form esters. One of ordinary skill in the art will recognize that alternate activating agents are also useful for the coupling of alcohols and carboxylic acids to form esters. Such alternate activating agents include, but are not limited to, EDC, HBTU, BOP, PyBOP, carbonyl diimidazole, disuccinimidyl carbonate and the like. One of ordinary skill in the art will further recognize that alternatives to carboxylic acids with activating agents are useful for the formation of esters from alcohols. Such alternatives include functional reagents that include, and are not limited to, anhydrides, acid chlorides, acyl imidazoles, acyl succinimides and the like. One of ordinary skill in the art will recognize that alternatives to the benzyl ether protecting group, and associated reaction conditions for their cleavage, are useful. Various appropriate alcohol protecting groups are broadly described in "Green's *Protective Groups in Organic Synthesis*". Such benzyl ether alternatives include, but are not limited to, trimethylsilyl ethers, tert-butyl dimethylsilyl ethers, triisopropylsilyl ethers, tert-butyl diphenylsilyl ethers, acetates, benzoates, 4-nitrobenzoates, tert-butyl ethers, 4-methoxybenzyl ethers and the like.

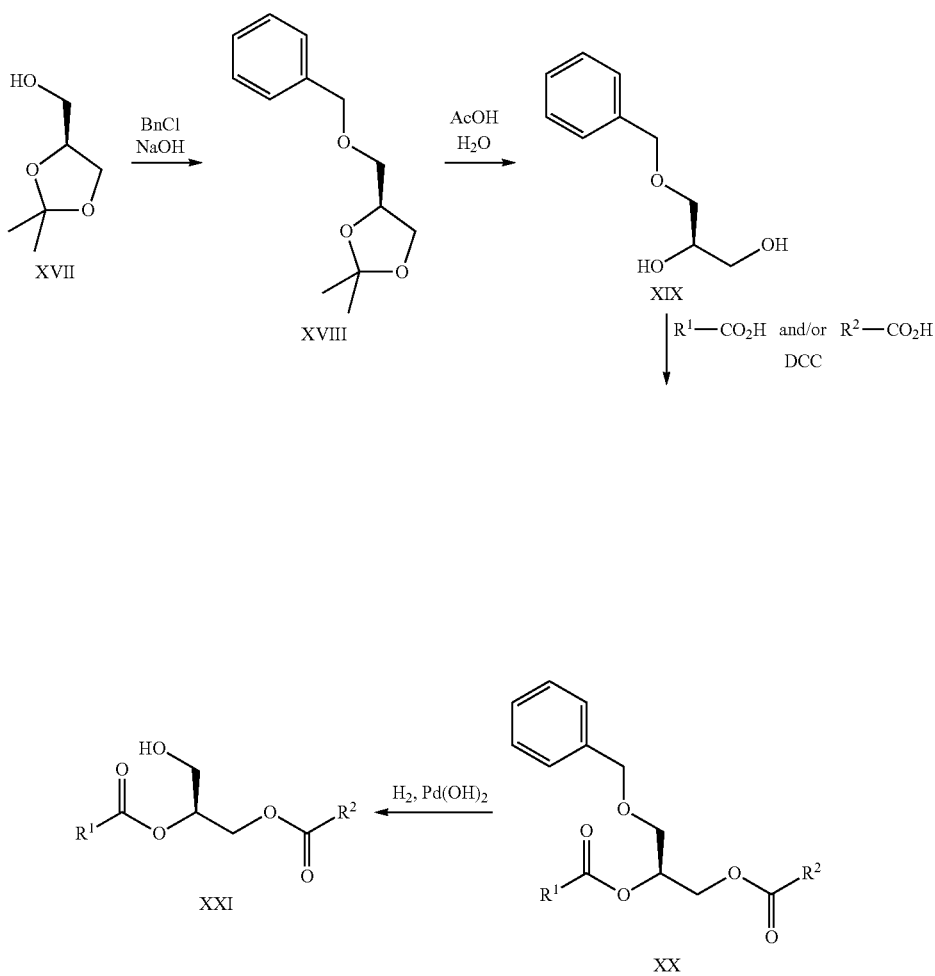

Scheme 7

As illustrated in Scheme 8, a compound of Formula XXII is converted to a benzyl ether giving a compound of Formula XXIII. The ketal of a compound of Formula XXIII is then cleaved giving a compound of Formula X. One of ordinary skill in the art will recognize that alternate reagents and reaction conditions are useful for formation of a benzyl ether. One of ordinary skill in the art will also recognize that alternatives to the benzyl ether protecting group, and associated reaction conditions for their formation, are useful. Various appropriate alcohol protecting groups are broadly described in "Green's Protective Groups in Organic Synthesis". Such benzyl ether alternatives include, but are not limited to, trimethylsilyl ethers, tert-butyl dimethylsilyl ethers, triisopropylsilyl ethers, tert-butyl diphenylsilyl ethers, acetates, benzoates, 4-nitrobenzoates, tert-butyl ethers, 4-methoxybenzyl ethers and the like. Similarly, one of ordinary skill in the art will recognize that alternative reaction conditions are useful for the cleavage of acetals and ketals. Such conditions are generally described in "Green's Protective Groups in Organic Synthesis".

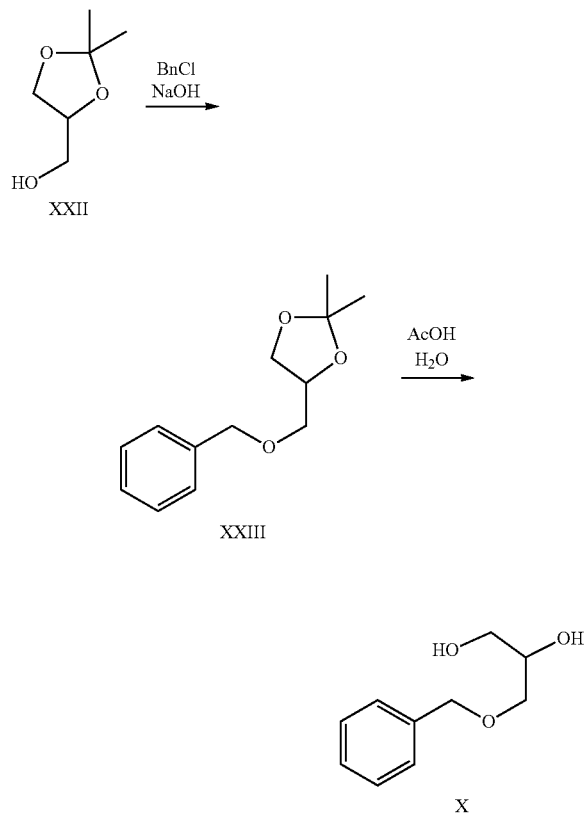

As illustrated in Scheme 9, a compound of Formula X is converted to a compound of Formula XXIV. A compound of Formula XXIV is a bis-carbonate, a bis-ester or a bis-carbamate. On hydrogenation, the benzyl ether of compound XXIV is cleaved giving a compound of Formula XXV.

One of ordinary skill in the art will recognize that a bis-carbonate version of a compound of Formula XXIV can be prepared by reacting a compound of Formula X with functional reagents that include, but are not limited to, chloroformates, pyrocarbonates and the like. One of ordinary skill in the art will recognize that carbonate formation can include use of bases such as, but not limited to, triethylamine, triisopropylamine, diisopropylethylamine, DBU, N-methylmorpholine, N-methylpyridine, N,N-dimethylpiperazine and the like. One of ordinary skill in the art will recognize that carbonate formation can include use of acyl transfer catalysts such as, but not limited to, DMAP, pyridine, 2-methylpyridine and the like. One of ordinary skill in the art will recognize that carbonate formation can include use of Lewis acid catalysts such as, but not limited to, zinc chloride, zinc acetate, zinc bromide, aluminum trichloride, titanium trichloride, titanium isopropoxide, boron trifluoride, tin chloride, alumina, silica gel and the like.

One of ordinary skill in the art will recognize that a bis-acetate version of a compound of Formula XXIV can be prepared by reacting a compound of Formula X with functional reagents that include, but are not limited to, anhydrides, acid chlorides, acyl imidazoles, acyl succinimides and the like. Additionally, one of ordinary skill in the art will recognize that carboxylic acids in the presence of activating agents will produce similar results. Suitable activating agents include, but are not limited to, DCC, EDC, HBTU, BOP, PyBOP, carbonyl diimidazole, disuccinimidyl carbonate and the like.

One of ordinary skill in the art will recognize that a bis-carbamate version of a compound of Formula XXIV can be prepared by reacting a compound of Formula X with functional reagents that include, but are not limited to, isocyanates and the like. One of ordinary skill in the art will recognize that bases can facilitate carbamate formation. Such bases include, but are not limited to, triethylamine, triisopropylamine, diisopropylethylamine, DBU, N-methylmorpholine, N-methylpyridine, N,N-dimethylpiperazine and the like. One of ordinary skill in the art will recognize that acyl transfer catalysts can facilitate carbamate formation. Such acyl transfer catalysts include, but are not limited to, DMAP, pyridine, 2-methylpyridine and the like. Additionally, one of ordinary skill in the art will recognize that introduction of Lewis acid catalysts may facilitate carbamate formation. Such Lewis acid catalysts include, but are not limited to, zinc chloride, zinc acetate, zinc bromide, aluminum trichloride, titanium trichloride, titanium isopropoxide, boron trifluoride, tin chloride, alumina, silica gel and the like.

One of ordinary skill in the art will also recognize that alternatives to the benzyl ether protecting group, and associated reaction conditions for their cleavage, are useful. Various appropriate alcohol protecting groups are broadly described in "Green's Protective Groups in Organic Synthesis". Such benzyl ether alternatives include, but are not limited to, trimethylsilyl ethers, tert-butyl dimethylsilyl ethers, triisopropylsilyl ethers, tert-butyl diphenylsilyl ethers, acetates, benzoates, 4-nitrobenzoates, tert-butyl ethers, 4-methoxybenzyl ethers and the like.

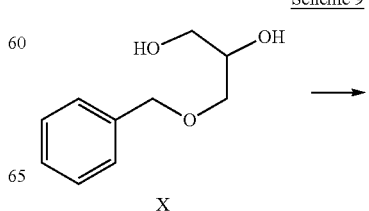

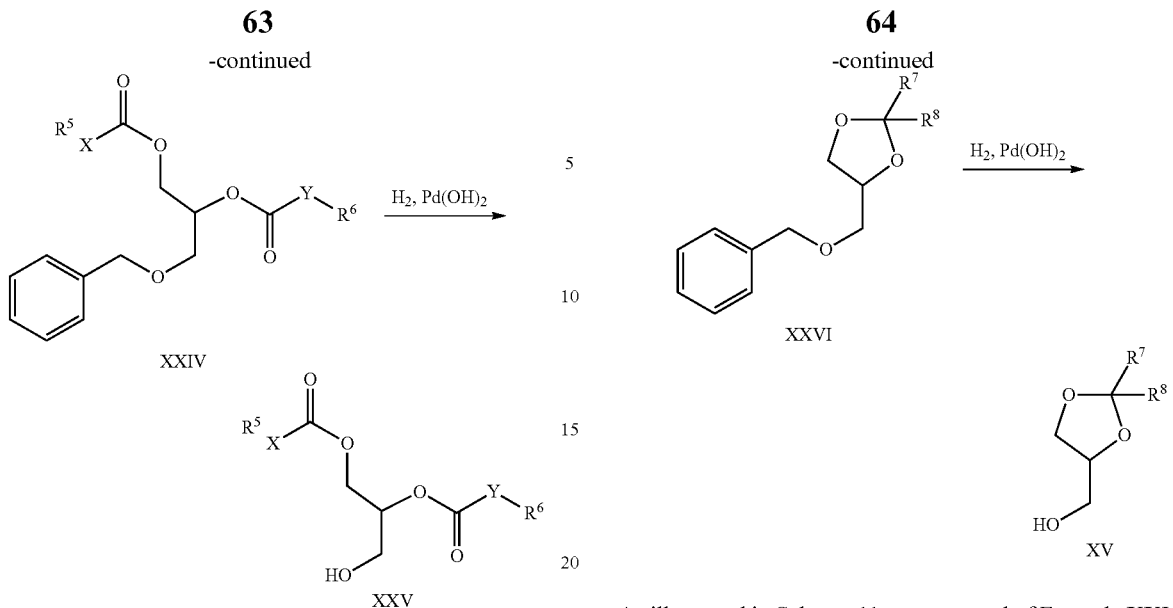

As illustrated in Scheme 10, compounds of Formula X are reacted with acetals, ketals, aldehydes or ketones in the presence of an acid catalyst producing compounds of Formula XXVI. Subsequent cleavage of the benzyl ether protecting group gives compounds of Formula XV. One of ordinary skill in the art will recognize that for preparation of compounds of Formula XXVI alternatives to acetals, ketals, aldehydes or ketones will produce similar results. Such alternatives include, but are not limited to, vinyl ethers and the like. Additionally, one of ordinary skill in the art will recognize that while p-toluenesulfonic acid is an appropriate acid catalyst for the formation of acetals and ketals, alternative acid catalysts are also useful. Such alternatives to p-toluenesulfonic acid include, but are not limited to, PPTS, sulfuric acid, methanesulfonic acid, Amberlyst resin, DOWEX acid resin, silica gel and the like. Furthermore, one of ordinary skill in the art will recognize that a compound of Formula XXVI can be converted into an alternate compound of Formula XXVI on reaction with an alternate acetal, ketal, aldehyde or ketone in the presence of an acid catalyst. One of ordinary skill in the art will recognize that alternatives to the benzyl ether protecting group, and associated reaction conditions for their cleavage, are useful. Various appropriate alcohol protecting groups are broadly described in "Green's Protective Groups in Organic Synthesis". Such benzyl ether alternatives include, but are not limited to, trimethylsilyl ethers, tert-butyl dimethylsilyl ethers, triisopropylsilyl ethers, tert-butyl diphenylsilyl ethers, acetates, benzoates, 4-nitrobenzoates, tert-butyl ethers, 4-methoxybenzyl ethers and the like. One of ordinary skill in the art will recognize that a compound of Formula XV includes a compound of Formula XXII.

Scheme 10

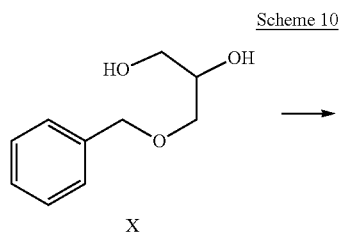

As illustrated in Scheme 11, a compound of Formula XXI couples to a compound of Formula XV or a compound of Formula XXV through a phosphodiester linkage. Subsequent salt formation of the phosphodiester gives a compound of Formula XXVII. One of ordinary skill in the art will recognize that a compound of Formula XXI, a compound of Formula XV and a compound of Formula XXV all contain primary hydroxyl groups. One of ordinary skill in the art will also recognize that formation of phosphodiesters between two different alcohols is achievable through use of a variety of phosphorus reagents and reaction conditions. Phosphorus reagents useful for the generation of phosphodiesters include, but are not limited to, POCl3,

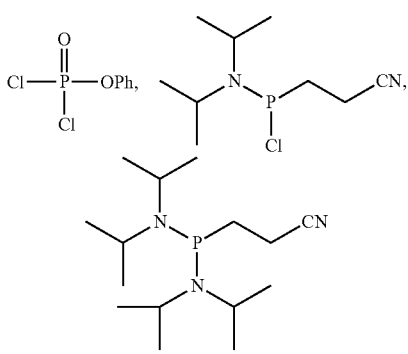

and the like. In some instances, the two alcohols are combined simultaneously with the phosphorus reagent. In some instances, the two hydroxyl groups are reacted with the phosphorus reagent in sequence. In some instances, the phosphodiester formation requires additional steps including, but not limited to, oxidation, deprotection or a combination thereof either executed as single additional steps or as multiple additional steps. One of ordinary skill in the art will recognize that bases can facilitate reaction with phosphorus reagents useful for phosphodiester formation. Such bases include, but are not limited to, triethylamine, triisopropylamine, diisopropylethylamine, DBU, N-methylmorpholine, N-methylpyridine, N,N-dimethylpiperazine and the like. One of ordinary skill in the art will recognize that acyl transfer catalysts can facilitate reaction with phosphorus reagents useful for phosphodiester formation. Such acyl transfer catalysts include, but are not limited to, DMAP, pyridine, 2-methylpyridine and the like. One of ordinary skill in the art will recognize that useful reagents for phosphodiester salt formation include, but are not limited to, DOWEX Na+ resin, sodium bicarbonate, sodium carbonate and the like. One of ordinary skill in the art will recognize that compounds of Formula XXVII include compounds 1, 2, 3, 4, 5, 6, 7, 8, 9 and 12.

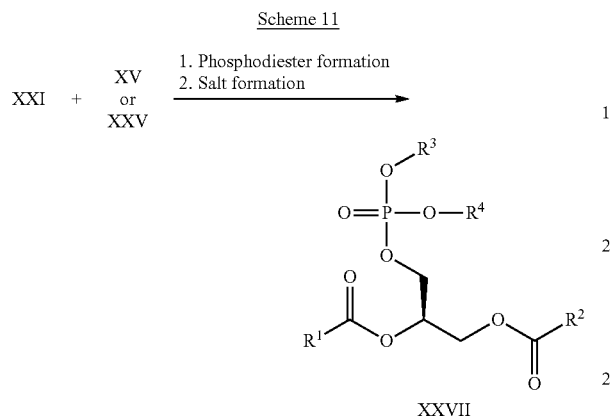

Scheme 11

With reference to Schemes 1-11, one of ordinary skill in the art will recognize that, collectively, said schemes enable the preparation of various stereoisomers of a compound of Formula 1. Furthermore, one of ordinary skill in the art will recognize that the various forms of the compounds of this invention include salt forms other than Na. With reference to different salt forms, compounds of Formula I, wherein $R^4$ is as generally defined, can be converted from the OH form or from a given salt form into an alternate salt form. Reagents useful for such form interconversions include, but are not limited to, magnesium chloride, calcium chloride and the like. One of ordinary skill in the art will recognize that, including $R^4$ conversion, compounds of Formula XXVII include compounds 10, 11, 13, 14, 15, 16, 17, 18, 19, 20, 21, 22, 23, 24, 25, 26, 27, 28, 29 and 30.

It is contemplated that any embodiment discussed in this specification can be implemented with respect to any method, kit, reagent, or composition of the invention, and vice versa. Furthermore, compositions of the invention can be used to achieve methods of the invention.

EXAMPLES

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

In executing the following exemplary synthetic protocols, the following relates to particulars relevant to equipment and analytical protocols. HPLC analyses were carried utilizing an XBridge C8 column (50×4.6 mm, 3.5μ) with the following method. Solvent A=25% ammonia in water, B=Acetonitrile; Flow Rate: 1 ml/min.

Example 1—Preparation of Sodium (R)-2,3-bis (tetradecanoyloxy)propyl (2,3-diacetoxypropyl) Phosphate (Compound 1)

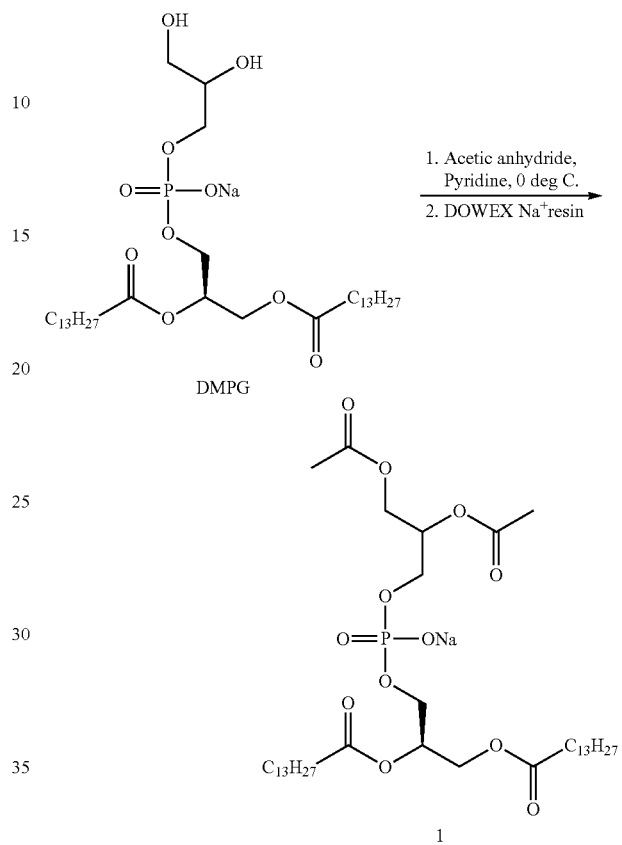

Acetic anhydride (3.5 ml, 36.3 mmol, 10 equiv) was added to a solution of DMPG sodium salt (2.5 g, 3.63 mmol) in dry pyridine (50 ml, 20 vol) at room temperature (25° C.) under nitrogen atmosphere. DMAP (88 mg, 0.725 mmol, 0.2 equiv) was added to the mixture and heated to 100° C. for 48 h. Upon completion of the reaction (as confirmed by TLC analysis, 20% MeOH in DCM, $R_f$~0.6, identified by Phosphomolybdic acid stain), the solvent was evaporated, and the crude product was passed through column chromatography packed with neutral silica gel (230-400 mech). (Note: Silica gel was neutralized by washing with 10% ammonia in methanol). The product was eluted with dichloromethane containing 10% methanol to afford (R)-2,3-bis(tetradecanoyloxy)propyl (2,3-diacetoxypropyl) phosphate as its ammonium salt. The resultant ammonium salt was exchanged to Na salt by passing through a pad of Dowex® 50WX8 Na+ resin in dichloromethane containing 10% methanol. The product fractions were collected and concentrated. The product was dissolved in a mixture of acetonitrile and water (5 ml:15 ml) and lyophilized to give the sodium salt of (R)-2,3-bis(tetradecanoyloxy)propyl (2,3-diacetoxypropyl) phosphate as light brown solid. Yield: 1.2 g (44%). $^1$H-NMR (400 MHz, DMSO-d$_6$): $\delta_H$ 4.99-5.05 (m, 2H), 4.20-4.29 (m, 2H), 4.07 (m, 2H), 3.67 (m, 4H), 2.26 (t, J=4.49 Hz, 4H), 2.01 (s, 6H), 1.49 (m, 4H), 1.23 (m, 40H), and 0.85 (t, J=4.04 Hz, 6H) ppm. $^{13}$C-NMR (100 MHz, DMSO-d$_6$): $\delta_H$ 172.63, 172.45, 170.37, 170.08, 71.07, 70.99, 70.89, 63.85, 62.98, 62.81, 33.99, 33.83, 31.85, 29.68, 29.62, 29.56, 29.39, 29.35, 29.30, 29.07, 29.00, and 24.94 ppm. LCMS (ELSD): 749.1 (M-23).

Example 2—Preparation of Sodium (R)-2, 3-bis (tetradecanoyloxy)propyl ((2,2-dimethyl-1,3-dioxolan-4-yl)methyl) Phosphate (Compound 12)

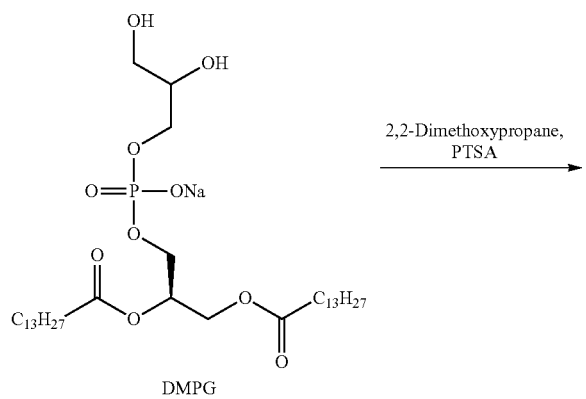

2,2-Dimethoxypropane (7.54 g, 72.5 mmol, 10 equiv) and p-Toluenesulfonic acid (72 mg, 0.378 mmol, 0.052 equiv) was added to a solution of DMPG sodium salt (5 g, 7.25 mmol) in toluene (200 ml, 40 vol). The mixture was heated to 140° C. for 16 h. The solvent was evaporated and the crude product (5.6 g) was taken for the next step without further purification.

Example 3—Preparation of Sodium (R)-2, 3-bis (tetradecanoyloxy)propyl ((2-heptadecyl-1,3-dioxolan-4-yl)methyl) Phosphate (Compound 4)

Octadecanaldehyde (4.55 g, 16.97 mmol, 3 equiv) was added to a solution of crude Compound 12 (4 g, 5.65 mmol) in 1,2-dichloroethane (80 ml, 20 vol) at room temperature (25° C.) followed by Amberlyst-15 (800 mg, 20 wt %). The mixture was stirred at 80° C. for 48 h. Upon completion of the reaction (as confirmed by TLC analysis, 15% MeOH in DCM, $R_f$~0.4, identified by Phosphomolybdic acid stain), the reaction mixture was filtered and washed with aqueous $NaHCO_3$ solution (1×80 ml). The aqueous layer was extracted with DCM (3×50 ml) and the combined organic layers were dried over sodium sulphate. The organic layer was concentrated, and the crude product was passed through column chromatography packed with neutral silica gel (230-400 mech). (Note: Silica gel was neutralized by washing with 10% ammonia in methanol). The product was eluted with dichloromethane containing 10-12% methanol to afford (R)-2, 3-bis (tetradecanoyloxy)propyl ((2-heptadecyl-1,3-dioxolan-4-yl)methyl) phosphate as its ammonium salt (1.8 g). The (R)-2, 3-bis (tetradecanoyloxy)propyl ((2-heptadecyl-1,3-dioxolan-4-yl)methyl) phosphate was further purified by triturating with a mixture of DCM:MeOH (9 ml:90 ml). The resultant solid was filtered and washed with methanol (1×10 ml). The ammonium salt was exchanged to Na salt by passing through a pad of Dowex® 50WX8 Na+ resin using 10% methanol in dichloromethane. The product fractions were collected and concentrated to give the sodium (R)-2, 3-bis (tetradecanoyloxy)propyl ((2-heptadecyl-1,3- dioxolan-4-yl)methyl) phosphate as off-white solid. Yield: 1.168 g (24.6%, 2 steps). $^1$H-NMR (400 MHz, DMSO-d$_6$): $\delta_H$ 5.27 (m, 1H), 4.97-4.84 (m, 1H), 4.40-4.35 (m, 3H), 4.26-4.12 (m, 2H), 4.07 (m, 1H), 4.00-3.96 (m, 1H), 3.87 (m, 1H), 3.68 (m, 1H), 2.31 (t, J=7.40 Hz, 4H), 1.61 (m, 6H), 1.26 (m, 70H), and 0.89 (t, J=6.04 Hz, 9H) ppm. $^{13}$C-NMR (100 MHz, CDCl$_3$): $\delta_H$ 173.51, 173.40, 105.20, 104.61, 74.47, 70.55, 67.11, 66.52, 65.88, 63.94, 62.74, 34.27, 34.15, 34.08, 34.02, 31.94, 31.93, 29.83, 29.80, 29.77, 29.75, 29.73, 29.71, 29.68, 29.51, 29.46, 29.40, 29.37, 29.30, 29.29, 24.97, 24.88, 24.46, 24.10, 22.69, 14.16, and 14.15 ppm.

Example 4—Preparation of Sodium (R)-2,3-bis (tetradecanoyloxy)propyl ((2-pentadecyl-1,3-dioxolan-4-yl)methyl) Phosphate (Compound 5)

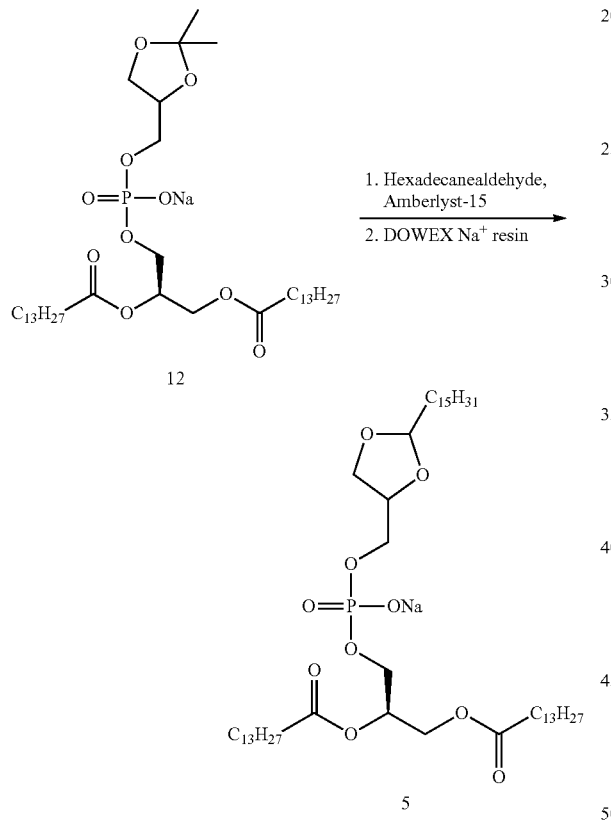

Hexadecanaldehyde (6.12 g, 25.4 mmol, 3 equiv) was added to a solution of crude Compound 12 (6 g, 8.42 mmol) in 1,2-dichloroethane (120 ml, 20 vol) at room temperature (25° C.). To this was added Amberlyst-15 (1.2 g, 20 wt %) and the mixture was stirred at 80° C. for 48 h. Upon completion of the reaction (as confirmed by TLC analysis, 15% MeOH in DCM, R$_f$~0.4, identified by Phosphomolybdic acid stain), the reaction mixture was filtered and washed with aqueous sodium bicarbonate solution (1×100 ml). The aqueous layer was extracted with DCM (3×60 ml) and the combined organic layer as dried over anhydrous sodium sulphate. The organic layer was concentrated, and the crude product was passed through a bed of neutral silica gel (230-400 mech). (Note: Silica gel was neutralized by washing with 10% ammonia in methanol). The product was eluted with dichloromethane containing 10% methanol to afford (R)-2,3-bis(tetradecanoyloxy)propyl ((2-pentadecyl-1,3-dioxolan-4-yl)methyl) phosphate as its ammonium salt. The ammonium salt was exchanged to sodium salt by passing through a pad of Dowex® 50WX8 Na+ resin using 10% methanol in dichloromethane. The product fractions were collected and concentrated to give the sodium salt of (R)-2,3-bis(tetradecanoyloxy)propyl ((2-pentadecyl-1,3-dioxolan-4-yl)methyl) phosphate as off-white solid (1.30 g, 17.3% yield over 2 steps). $^1$H-NMR (400 MHz, DMSO-d$_6$): $\delta_H$ 5.24 (m, 1H), 4.99-4.81 (2 t, J=4.4 Hz, 1H), 4.42 (m, 1H), 4.26-4.17 (m, 2H), 4.12-3.65 (m, 6H), 2.34-2.28 (m, 4H), 1.60 (m, 6H), 1.32 (m, 66H), and 0.90 (t, J=7.2 Hz, 9H) ppm. $^{13}$C-NMR (100 MHz, CDCl$_3$): $\delta_H$ 173.59, 105.19, 104.63, 74.6, 70.74, 67.22, 66.41, 65.71, 63.58, 62.83, 34.33, 34.16, 34.11, 34.05, 31.95, 29.81, 29.79, 29.72, 29.68, 29.51, 29.47, 29.41, 29.31, 24.98, 24.90, 24.49, 24.12, 22.70, and 14.09 ppm.

Example 5—Preparation of Sodium (R)-2,3-bis (tetradecanoyloxy)propyl ((2-pentyl-1,3-dioxolan-4-yl)methyl) Phosphate (Compound 6)

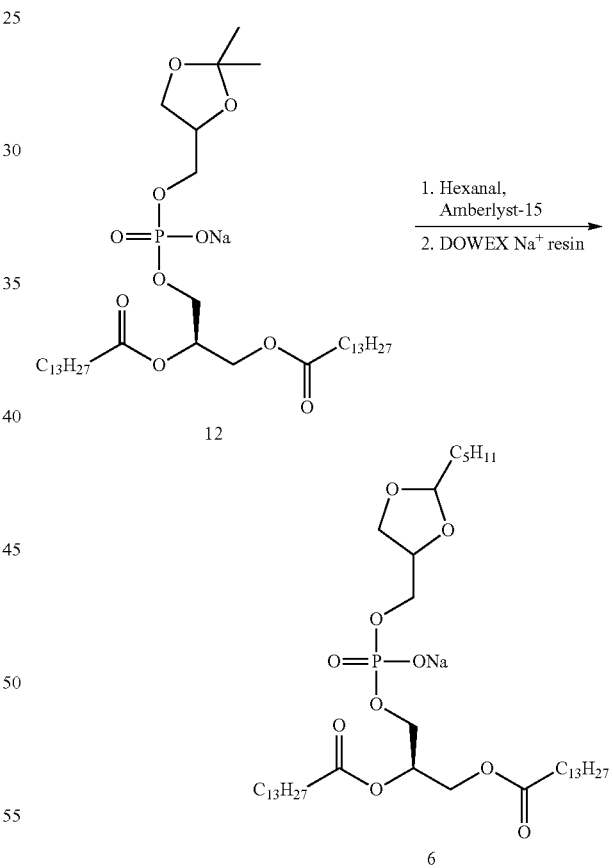

Hexanal (4.17 ml, 33.94 mmol, 6 equiv) was added to a solution of crude Compound 12 (4 g, 5.65 mmol) in DCM (80 ml, 20 vol) at room temperature (25° C.). To this was added Amberlyst-15 (800 mg, 20 wt %) and the mixture was stirred at room temperature for 16 h. Upon completion of the reaction (as confirmed by TLC analysis, 15% MeOH in DCM, Rf~0.4, identified by Phosphomolybdic acid stain), the reaction mixture was filtered and washed with aqueous sodium bicarbonate solution (80 ml). The aqueous layer was extracted with DCM (3×50 ml) and the combined organic layer was dried over anhydrous sodium sulphate. The organic layer was concentrated under reduced pressure and the crude product was passed through as plug of neutral silica (230-400 mesh) eluting with dichloromethane containing 10% methanol to afford (R)-2,3-bis(tetradecanoyloxy)propyl ((2-pentyl-1,3-dioxolan-4-yl)methyl) phosphate as its ammonium salt. The resultant ammonium salt was exchanged to sodium salt by passing through a pad of Dowex® 50WX8 Na+ resin using 10% methanol in dichloromethane. The product fractions were collected and concentrated to give the sodium salt of (R)-2,3-bis(tetradecanoyloxy)propyl ((2-pentyl-1,3-dioxolan-4-yl)methyl) phosphate as light brown sticky solid. Yield: 1.77 g (41.74%). $R_f$=0.4 in 10:1.5/DCM:MeOH. $^1$H-NMR (400 MHz, DMSO-$d_6$): $\delta_H$ 5.08 (m, 1H), 4.85-4.77 (m, 1H), 4.28 (m, 1H), 4.09-4.00 (m, 2H), 3.78-3.62 (m, 3H), 3.58-3.48 (m, 2H), 2.26 (t, J=5.24 Hz, 4H), 1.50 (m, 6H), 1.27 (m, 47H), and 0.85 (t, J=0.85 Hz, 9H) ppm. $^{13}$C-NMR (100 MHz, CDCl$_3$): $\delta_H$ 173.65, 173.57, 105.21, 104.61, 74.64, 74.57, 70.76, 70.69, 67.17, 67.07, 66.36, 65.61, 63.54, 62.84, 34.32, 34.11, 34.03, 33.91, 31.95, 31.87, 31.77, 29.78, 29.76, 29.71, 29.65, 29.49, 29.45, 29.40, 29.30, and 24.97 ppm.

Example 6—Preparation of Sodium 2,3-bis(butyryloxy)propyl ((R)-2,3-bis(tetradecanoyloxy)propyl) Phosphate (Compound 7)

Butyric anhydride (8.96 g, 56.61 mmol, 13 equiv) was added to a solution of DMPG sodium salt (3.0 g, 4.35 mmol) in dry pyridine (60 ml, 20 vol) at room temperature (25° C.) under nitrogen atmosphere. DMAP (1.59 g, 13.07 mmol, 3.0 equiv) was added to the mixture in portions and the mixture was stirred at room temperature for 20 h. Upon completion of the reaction (as confirmed by TLC and LCMS analysis, 20% MeOH in DCM, $R_f$~0.6, identified by Phosphomolybdic acid stain), the solvent was evaporated, and the crude product was passed through a plug of silica gel (230-400 mesh) eluting with dichloromethane containing 10% of methanol to afford the product as thick gum. This was diluted with ethyl acetate (20 vol) and washed with 1.5 N HCl (10 vol) followed by water. The organic layer was then stirred with aqueous NaHCO$_3$ solution (3 equiv in 5 vol of water) at room temperature for 30 min. The organic layer was separated, dried over Na$_2$SO$_4$ and concentrated under vacuum to get sodium 2,3-bis(butyryloxy)propyl ((R)-2,3-bis(tetradecanoyloxy)propyl) phosphate as a thick syrup (1.6 g, 44% yield). $^1$H-NMR (400 MHz, CDCl$_3$): $\delta_H$ 5.23-5.25 (m, 2H), 4.40-4.43 (m, 2H), 4.18-4.24 (m, 2H), 3.93 (m, 4H), 2.28-2.33 (m, 8H), 1.58-1.68 (m, 8H), 1.27-1.33 (m, 40H), and 0.95-0.97 (m, 6H) ppm. $^{13}$C-NMR (100 MHz, CDCl$_3$): $\delta_H$ 173.57, 173.45, 70.72, 63.51, 62.70, 36.08, 35.91, 34.29, 34.08, 31.94, 29.75, 29.69, 29.65, 29.62, 29.45, 29.42, 29.39, 29.26, 29.24, 24.94, 24.87, 22.69, 18.31, 18.28, 14.10, 13.62 and 13.57 ppm.

Example 7—Preparation of Sodium 2,3-bis((3-methylbutanoyl)oxy)propyl ((R)-2,3-bis(tetradecanoyloxy)propyl) Phosphate (Compound 8)

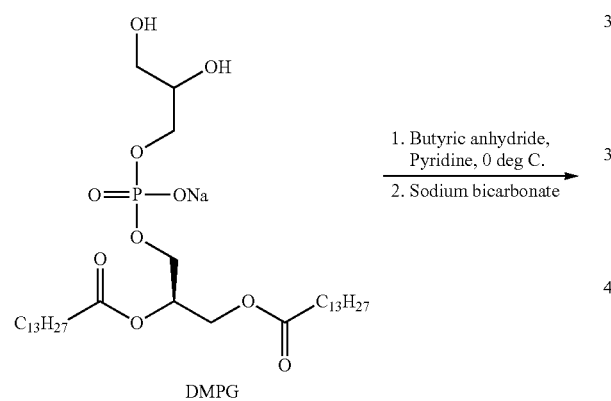

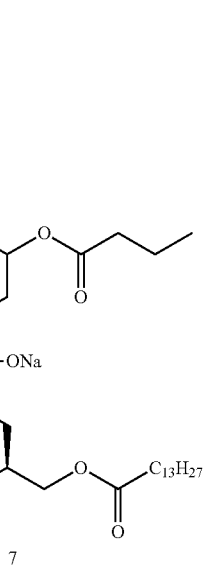

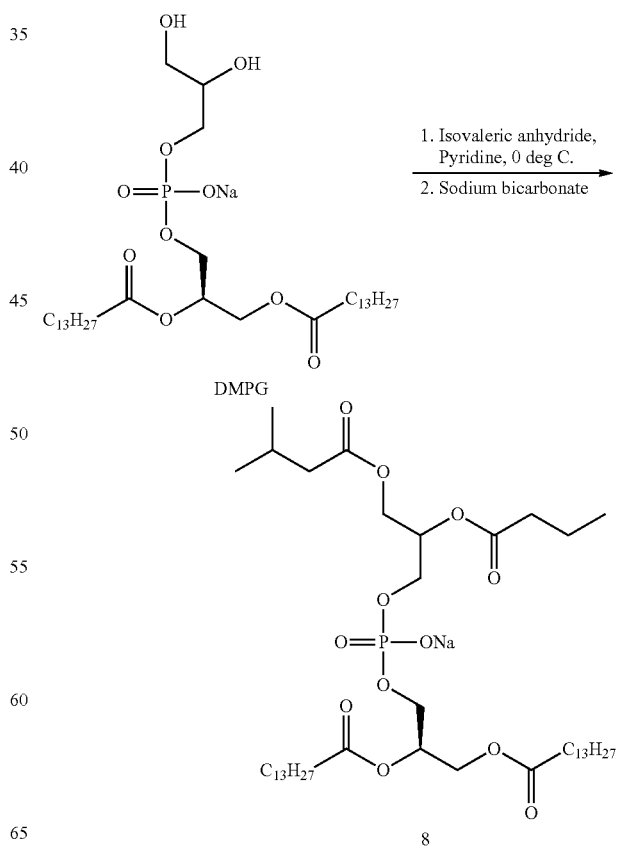

Isovaleric anhydride (10.55 g, 56.66 mmol, 13 equiv) was added to a solution of DMPG sodium salt (3.0 g, 4.35 mmol) in dry pyridine (60 ml, 20 vol) at room temperature (25° C.) under nitrogen atmosphere. To this was added DMAP (1.59 g, 13.07 mmol, 3.0 equiv) in portions and the mixture was stirred at room temperature for 20 h. Upon completion of the reaction (as confirmed by TLC and LCMS analysis, 20% MeOH in DCM, $R_f$-0.6, identified by Phosphomolybdic acid stain), the solvent was evaporated and the crude product was passed through a plug of silica gel (230-400 mesh) eluting with dichloromethane containing 10% of methanol to afford the product as thick gum. This was diluted with ethyl acetate (20 vol) and washed with 1.5 N HCl (10 vol) followed by water. The organic layer was then stirred with aqueous $NaHCO_3$ solution (3 equiv in 5 vol of water) at room temperature for 30 min. The organic layer was separated, dried over $Na_2SO_4$ and concentrated under vacuum to get sodium 2,3-bis((3-methylbutanoyl)oxy)propyl ((R)-2,3-bis(tetradecanoyloxy)propyl) phosphate as a thick syrup (2.4 g, 64% yield). $^1$H-NMR (400 MHz, $CDCl_3$): $\delta_H$ 5.24-5.29 (m, 2H), 4.40-4.44 (m, 2H), 4.18-4.22 (m, 2H), 3.95 (m, 4H), 2.19-2.34 (m, 8H), 2.06-2.12 (m, 2H), 1.58-1.61 (m, 4H), 1.27-1.33 (m, 40H), 0.96 (d, J=6.8 Hz, 12H) and 0.90 (t, J=7.2 Hz, 6H) ppm. $^{13}$C-NMR (100 MHz, $CDCl_3$): $\delta_H$ 173.51, 173.38, 172.80, 172.71, 70.69, 70.62, 63.59, 62.72, 43.27, 43.07, 34.27, 34.07, 31.92, 29.73, 29.67, 29.63, 29.60, 29.44, 29.41, 29.36, 29.25, 29.24, 25.50, 24.93, 24.86, 22.67, 22.34, 22.30, and 14.07 ppm. LCMS (ELSD): 833.5 (M-23). Method: Mobile Phase A: 1 ml of 25% ammonia solution in 1000 ml of MilliQ Water (pH: 9 with Acetic acid). Mobile Phase B: acetonitrile. Flow rate: 1.0 ml/min. COLUMN: XBridge C8 (50×4.6) mm, 3.5μ. Rt (min): 5.74; Area %—98.84.

Example 8—Preparation of Sodium 2,3-bis(isobutyryloxy)propyl ((R)-2,3-bis(tetradecanoyloxy)propyl) Phosphate (Compound 9)

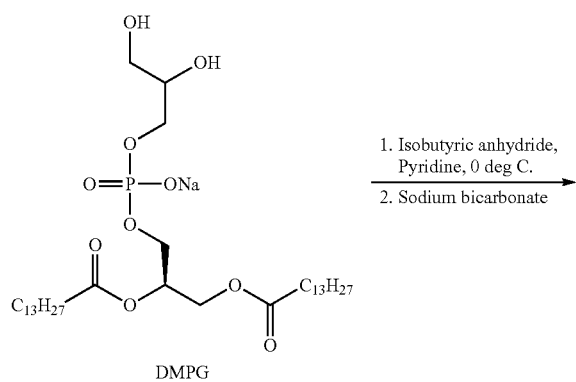

DMPG

-continued

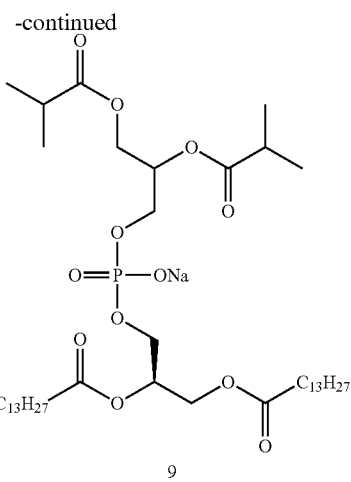

9

Isobutyric anhydride (10.55 g, 56.66 mmol, 13 equiv) was added to a solution of DMPG sodium salt (3.0 g, 4.35 mmol) in dry pyridine (60 ml, 20 vol) at room temperature (25° C.) under nitrogen atmosphere. DMAP (1.59 g, 13.07 mmol, 3.0 equiv) was added to this mixture in portions, and the mixture was stirred at room temperature for 20 h. Upon completion of the reaction (as confirmed by TLC and LCMS analysis, 20% MeOH in DCM, $R_f$-0.6, identified by Phosphomolybdic acid stain), the solvent was evaporated and the crude product was passed through a plug of silica gel (230-400 mesh) eluting with dichloromethane containing 10% of methanol to afford the product as thick gum. This was diluted with ethyl acetate (20 vol) and washed with 1.5 N HCl (10 vol) followed by water. The organic layer was then stirred with aqueous $NaHCO_3$ solution (3 equiv in 5 vol of water) at room temperature for 30 min. The organic layer was separated, dried over $Na_2SO_4$ and concentrated under vacuum to get sodium 2,3-bis(isobutyryloxy)propyl ((R)-2,3-bis(tetradecanoyloxy)propyl) phosphate as a thick syrup (1.6 g, 44% yield). $^1$H-NMR (400 MHz, $CDCl_3$): $\delta_H$ 5.24-5.27 (m, 2H), 4.39-4.44 (m, 2H), 4.17-4.23 (m, 2H), 3.94 (m, 4H), 2.52-2.60 (m, 2H), 2.28-2.33 (m, 4H), 1.58-1.61 (m, 4H), 1.31-1.33 (m, 40H), 1.32 (t, J=6.8 Hz, 12H) and 0.89 (t, J=7.2 Hz, 6H) ppm. $^{13}$C-NMR (100 MHz, $CDCl_3$): $\delta_H$ 176.74, 173.53, 173.41, 70.72, 63.50, 62.73, 34.28, 34.07, 33.93, 33.85, 31.92, 29.73, 29.68, 29.62, 29.60, 29.43, 29.39, 29.37, 29.24, 29.22, 24.92, 24.86, 22.68, 18.97, and 14.10 ppm.

Example 9—Preparation of Sodium 2,3-bis ((ethoxycarbonyl)oxy)propyl ((R)-2,3-bis (tetradecanoyloxy)propyl) Phosphate (Compound 2)

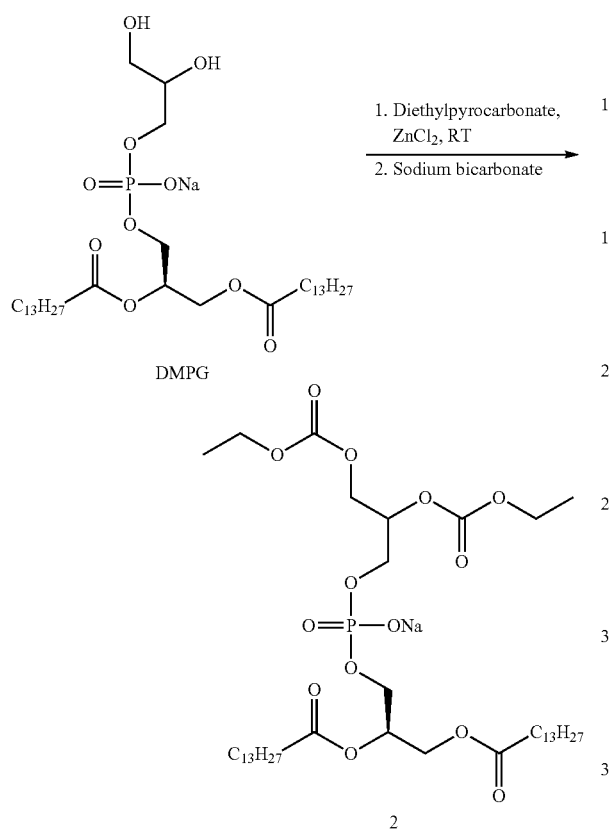

To a suspension of DMPG-Na (500.0 g, 0.7258 mol, 1.0 equiv) in toluene (15 vol) was added diethylpyrocarbonate (1176.5 g, 7.258 mol, 10 equiv) followed by anhydrous $ZnCl_2$ (128.61 g, 0.943 mol, 1.3 equiv) at room temperature under nitrogen. The mixture was stirred at 37-40° C. for 30 h. After completion of reaction, the reaction mixture was cooled to room temperature AND filtered through a thin bed of Celite®. The filtrate was concentrated under vacuum maintaining the bath temperature below 40° C. The sticky residue was dissolved in EtOAc (30 vol) and washed with water (5 vol×2). The organic layer was dried over $Na_2SO_4$ and concentrated under vacuum maintaining the bath temperature below 45° C. to get a sticky residue. The crude product (680 g) was purified by silica gel column chromatography (230-400 mesh) using 5-20% of MeOH in dichloromethane as gradient. The product fractions were concentrated to get 385 g of pure product. This was dissolved in a mixture of EtOAc and water (15:3 vol)) and cooled to ~5° C. To this was added HCl solution (0.5 N, 2 equiv) and the mixture was stirred for 15-20 minutes at ~5° C. The organic layer was separated and washed with 0.5 N HCl (3 vol×1) and water (5 vol×1). The organic layer was slowly basified with $NaHCO_3$ solution (4 equiv in 5 vol of water) at room temperature. The mixture was stirred for 2 h and the organic layer was separated, dried over $Na_2SO_4$ and concentrated to get sodium 2,3-bis((ethoxycarbonyl)oxy)propyl ((R)-2,3-bis (tetradecanoyloxy)propyl) phosphate as a thick syrup (300.0 g, 49% yield). $^1$H-NMR (400 MHz, $CDCl_3$): $\delta_H$ 5.23-5.25 (m, 1H), 5.10-5.11 (m, 1H), 4.49-4.36 (m, 2H), 4.35-4.16 (m, 6H), 4.03-3.91 (m, 4H), 2.34-2.28 (m, 4H), 1.61-1.57 (m, 4H), 1.35-1.27 (m, 46H), and 0.89 (t, J=68 Hz, 6H) ppm. $^{13}$C-NMR (100 MHz, $CDCl_3$): $\delta_H$ 173.56, 173.50 154.97, 154.77, 154.73, 74.51, 74.44, 70.71, 70.64, 65.88, 64.48, 64.41, 64.23, 63.55, 63.20, 62.74, 34.25, 34.04, 31.93, 29.76, 29.74, 29.70, 29.66, 29.62, 29.46, 29.42, 29.39, 29.26, 29.23, 24.93, 24.86, 22.69, and 14.10 ppm.

Example 10—Preparation of magnesium-2,3-bis ((ethoxycarbonyl)oxy)propyl((R)-2,3-bis(tetradecanoyloxy)propyl) Phosphate (Compound 10)

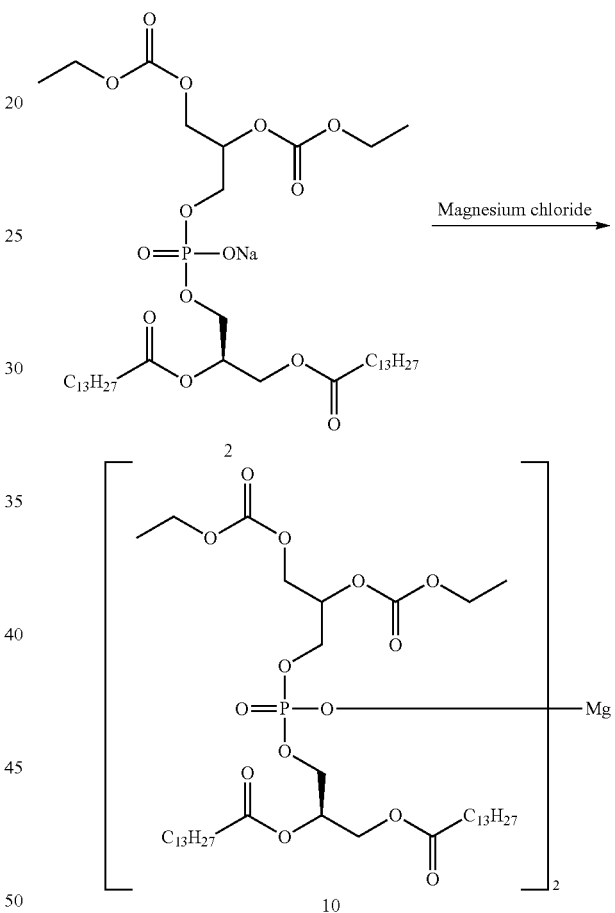

A solution of magnesium chloride (0.571 g, 6.00 mmol, 0.5 equiv) in water (10 vol) was added to sodium 2,3-bis ((ethoxycarbonyl)oxy)propyl ((R)-2,3-bis(tetradecanoyloxy)propyl) phosphate (10 g, 12.00 mmol, 1.0 equiv) in ethanol (100 ml), and the mixture was stirred at room temperature for 14 h. The mixture was diluted with water (200 ml) and the precipitate was filtered, washed with water (100 ml) and dried under vacuum to afford magnesium-2,3-bis((ethoxycarbonyl)oxy)propyl((R)-2,3-bis(tetradecanoyloxy)propyl) phosphate as an off-white solid (8.0 g, 79% yield). $^1$H-NMR (400 MHz, $CDCl_3$): $\delta_H$ 5.27 (m, 1H), 5.13 (m, 1H), 4.50-4.00 (m, 14H), 2.34-2.28 (m, 4H), 1.60-1.59 (m, 4H), 1.35 (m, 46H), and 0.89 (t, J=6.4 Hz, 6H) ppm. $^{13}$C-NMR (100 MHz, $CDCl_3$): $\delta_H$ 173.50, 173.31, 154.91, 154.60, 74.21, 70.31, 65.84, 64.35, 64.19, 63.96, 63.60, 62.70, 34.15, 34.00, 31.92, 29.75, 29.68, 29.66, 29.62, 29.48, 29.43, 29.37, 29.26, 29.22, 24.91, 22.67, 14.13 and 14.07 ppm.

Example 11—Preparation of calcium-2,3-bis ((ethoxycarbonyl)oxy)propyl ((R)-2,3-bis(tetradecanoyloxy)propyl) Phosphate (Compound 11)

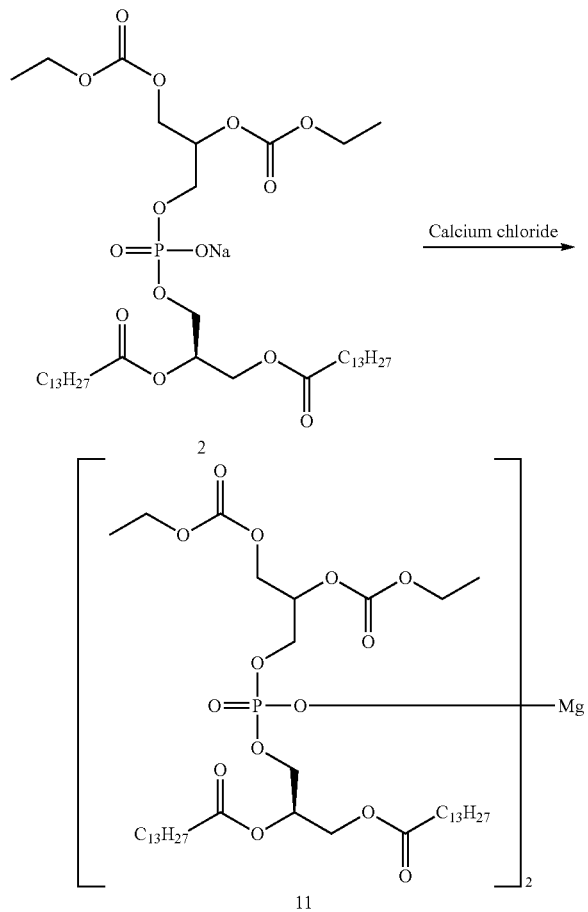

A solution of calcium chloride (0.666 g, 6.00 mmol, 0.5 equiv) in water (10 vol) was added to a solution of sodium 2,3-bis((ethoxycarbonyl)oxy)propyl ((R)-2,3-bis(tetradecanoyloxy)propyl) phosphate (10 g, 12.00 mmol, 1.0 equiv) in ethanol (100 ml) at room temperature and the mixture was stirred at room temperature for 14 h. The mixture was diluted with water (200 ml) and the precipitate was filtered, washed with water (100 ml) and dried under vacuum to afford calcium-2,3-bis((ethoxycarbonyl)oxy)propyl((R)-2,3-bis(tetradecanoyloxy)propyl) phosphate as an off white solid (8.2 g, 83% yield). $^1$H-NMR (400 MHz, CDCl$_3$): $\delta_H$ 5.28 (m, 1H), 5.19 (m, 1H), 4.51-4.40 (m, 2H), 4.36-4.14 (m, 6H), 3.90-4.10 (m, 4H), 2.34-2.28 (m, 4H), 1.59 (m, 4H), 1.33-1.27 (m, 46H), and 0.89 (t, J=6.8 Hz, 6H) ppm. $^{13}$C-NMR: (100 MHz, CDCl$_3$): $\delta_H$ 173.54, 154.99, 74.44, 70.59, 68.70, 65.95, 64.49, 64.26, 63.92, 62.71, 34.17, 34.00, 31.91, 29.74, 29.72, 29.67, 29.61, 29.46, 29.42, 29.37, 29.25, 29.20, 24.88, 24.80, 22.66, 14.11 and 14.05 ppm.

Example 12—Cardiac Response Testing

Efficacy evaluation of the compounds of the present invention involved ECG measurements of adult male Hartley guinea pigs wherein PR, QRS, QT, QTc, JT, RR were recorded. In typical experiments, subcutaneous Kaha TR50B bio potential telemeters were surgically implanted in adult male Hartley guinea pigs weighing 300 to 350 g at enrollment. One lead was sutured to the apex of the heart, while another was sutured to the side of the aorta. The animals were allowed to recover from surgery for 5 days prior to being returned to the testing colony. Following recovery, animals were subjected to two rounds of evaluation as follows:

In Round 1 of the testing, baseline ECG records were obtained for 5 minutes prior to exposing the animals to single oral doses of moxifloxacin (20 mg/kg), administered orally to 8 guinea pigs. ECG signals were acquired continuously for 6 hours post administration of moxifloxacin. The animals were then returned to their housing to washout the drug over 5 to 7 days.

In Round 2 of the testing of the 8 guinea pigs, baseline ECGs were obtained for 5 minutes to compare these baseline intervals with the intervals measured prior to the 1st exposure to moxifloxacin (above). The animals were administered a single oral dose of 2 mg/kg of test compound (selected from Compounds 1-12). Concomitantly, 6 animals were gavaged with the same batch of moxifloxacin (20 mg/kg). Another 2 animals were given moxifloxacin (20 mg/kg) only. The purpose of dosing these animals with moxifloxacin only was to verify whether a 2nd exposure to moxifloxacin would result in enhanced QT prolongation. ECGs were acquired continuously for 6 hours. The animals were then returned to their housing to washout the drug over 5 to 7 days.

ECG analysis over 5 minutes pre-dose and 6 hours post dose consisted in was automated based on pattern recognition algorithms. The analyzed data were binned into 5-minute segments. Intervals such as PR, QRS, QT, QTc, JT and RR were analyzed automatically using AD Instruments LabChart Pro v8. The accuracy of the measurements was verified manually using digital cursors by randomly selecting 3 to 5 segments at any given time postdose. There were no noted discrepancies between automated and manual intervals outside of arrhythmic episodes. The frequency of arrhythmia was quantified and expressed as "% of ECG time spent in abnormal sinus rhythm over entire duration of the recording".

The table below list the protection observed by test compounds against Moxifloxacin-induced QTc prolongation.

| | Moxifloxacin | Test Compound | | | | | | | | | |
|---|---|---|---|---|---|---|---|---|---|---|---|
| | 40 mg/kg | 6 | 4 | 2 | 1 | 5 | 11* | 10* | 7* | 8* | 9* |
| | | Protection indicated as percent (%) of Moxifloxacin effect | | | | | | | | | |
| Protection at 1 h post dose | n/a | 74 | 95 | 95 | 118 | 35 | 83 | 83 | 83 | 74 | 91 |
| Protection at 2 h post dose | n/a | 110 | 88 | 88 | 122 | 113 | 94 | 88 | 100 | 97 | 94 |

| | Moxifloxacin | Test Compound | | | | | | | | | |
|---|---|---|---|---|---|---|---|---|---|---|---|
| | 40 mg/kg | 6 | 4 | 2 | 1 | 5 | 11* | 10* | 7* | 8* | 9* |
| | | Protection indicated as percent (%) of Moxifloxacin effect | | | | | | | | | |
| Protection at 4 h post dose | n/a | 115 | 22 | 22 | 100 | 126 | 91 | 72 | 119 | 100 | 100 |
| Protection at 6 h post dose | n/a | 138 | 90 | 90 | 116 | 176 | 116 | 116 | 147 | 132 | 116 |
| Time of maximal protection | n/a | 2 h | 2 h | 2 h | 2 h | 2 h | 2 h | 2 h | 2 h | 2 h | 2 h |
| Duration of complete protection | n/a | 6 h | 4 h | 4 h | 6 h | 6 h | 6 h | 6 h | 6 h | 6 h | 6 h |
| Onset of protection | n/a | 1 h | 1 h | 1 h | 1 h | 2 h | 1 h | 1 h | 1 h | 1 h | 1 h |
| Maximal prolongation | 29 ms | 3 ms | 8 ms | 4 ms | 0 ms | 0 ms | 8 ms | 2 ms | 4 ms | 2 ms | 3 ms |

*Data for these compounds are preliminary

It will be understood that particular embodiments described herein are shown by way of illustration and not as limitations of the invention. The principal features of this invention can be employed in various embodiments without departing from the scope of the invention. Those skilled in the art will recognize or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

What is claimed is:

1. A method of reducing or eliminating one or more of a cardiac channelopathy, cardiac muscle damage, or a condition resulting from the irregularity or alteration in the cardiac pattern, in a human or animal subject, comprising the step of administering to the human or animal subject one or more of a compound of Formula I

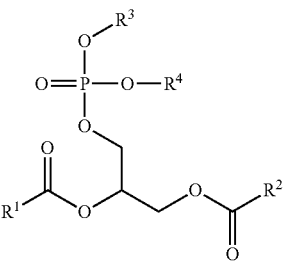

I wherein,
$R^1$ is a $C_1$-$C_{20}$ branched or unbranched hydrocarbon possessing 0-10 double bonds, 0-10 triple bonds or a combination of 0-10 double and triple bonds;
$R^2$ is a $C_1$-$C_{20}$ branched or unbranched hydrocarbon possessing 0-10 double bonds, 0-10 triple bonds or a combination of 0-10 double and triple bonds;
$R^3$ is

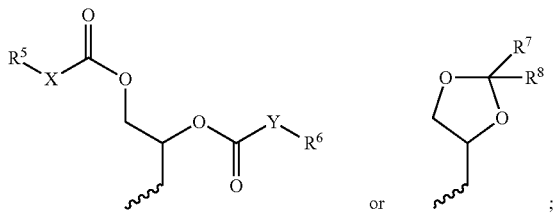

$R^4$ is H or a pharmaceutically acceptable cation, wherein incorporation of said pharmaceutically acceptable cation results in a salt;
$R^5$ is a $C_1$-$C_{10}$ branched or unbranched hydrocarbon optionally substituted with one or more groups selected from OH, OAc, OMe, $NH_2$, NHAc, NHMe, $N(Me)_2$, SH, CN, COOH, $CONH_2$, Cl, Br and I;
$R^6$ is a $C_1$-$C_{10}$ branched or unbranched hydrocarbon optionally substituted with one or more groups selected from OH, OAc, OMe, $NH_2$, NHAc, NHMe, $N(Me)_2$, SH, CN, COOH, $CONH_2$, Cl, Br and I;

$R^7$ is a $C_1$-$C_{20}$ branched or unbranched hydrocarbon possessing 0-10 double bonds, 0-10 triple bonds or a combination of 0-10 double and triple bonds;

$R^8$ is H or a $C_1$-$C_{20}$ branched or unbranched hydrocarbon possessing 0-10 double bonds, 0-10 triple bonds or a combination of 0-10 double and triple bonds;

X is a direct linkage, $CH_2$, O or NH;

Y is a direct linkage, $CH_2$, O or NH; and wherein each stereogenic center is independently R, S or racemic.

2. The method of claim 1, wherein the $R^4$ of the compound of Formula I is H, Li, Na, K, Mg, Ca, Zn, Cs, ammonium or tetraalkylammonium.

3. The method of claim 1, wherein the compound of Formula I exists as a single entity, a solvate, a hydrate, a crystal, an amorphous solid, a liquid or an oil.

4. The method of claim 1, wherein the compound of Formula I reduces or eliminates one or more of a cardiac channelopathy or a condition resulting from the irregularity or alteration in the cardiac pattern caused by the active agent used to treat a disease.

5. The method of claim 1, wherein the compound of Formula I is administered in an amount per unit dose of between about 1 mg and about 1 gram.

6. The method of claim 1, wherein the compound of Formula I is formulated for oral, sublingual, transdermal, suppository, intrathecal, enteral, parenteral, intravenous, intraperitoneal, cutaneous, subcutaneous, topical, pulmonary, rectal, vaginal, or intramuscular administration.

7. The method of claim 6, wherein the compound of Formula I is formulated for oral administration as a tablet, capsule, caplet, pill, powder, troche, lozenge, slurry, liquid solution, suspension, emulsion, elixir or oral thin film (OTF).

8. The method of claim 1, wherein the compound of Formula I is formulated as a solid form, a solution, a suspension, or a soft gel form.

9. The method of claim 8, wherein the solid form further comprises one or more excipients, binders, anti-adherents, coatings, disintegrants, fillers, flavors, dyes, colors, glidants, lubricants, preservatives, sorbents, sweeteners, derivatives thereof, or combinations thereof.

10. The method of claim 9, wherein the compound of Formula I is co-administered with one or more agents that induce a cardiopathy as a side effect.

11. The method of claim 10, wherein the one or more active agent that induce a cardiopathy as a side effect are selected from at least one of: Albuterol, Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Cocaine, Curcumin, Crizotinib, Dabrafenib, Dasatinib, Desipramine, Dexmedetomidine, Dexmethylpheni date, Dextroamphetamine, Amphetamine, Dihydroartemisinin and Piperaquine, Diphenhydramine, Disopyramide, Dobutamine, Dofetilide, Dolasetron, Domperidone, Dopamine, Doxepin, Dronedarone, Droperidol, Ephedrine, Epinephrine, Adrenaline, Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide, Frusemide, Galantamine, Gatifloxacin, Gemifloxacin, Granisetron, Halofantrine, Haloperidol, Hydrochlorothiazide, Ibutilide, Iloperidone, Imipramine, Melipramine, Indapamide, Isoproterenol, Isradipine, Itraconazole, Ivabradine, Ketoconazole, Lapatinib, Levalbuterol, Levofloxacin, Levomethadyl, Lisdexamfetamine, Lithium, Mesoridazine, Metaproterenol, Methadone, Methamphetamine, Methylphenidate, Midodrine, Mifepristone, Mirabegron, Mirtazapine, Moexipril/HCTZ, Moxifloxacin, Nelfinavir, Nicardipine, Nilotinib, Norepinephrine, Norfloxacin, Nortriptyline, Ofloxacin, Olanzapine, Ondansetron, Oxytocin, Paliperidone, Paroxetine, Pasireotide, Pazopanib, Pentamidine, Perflutren, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salbutamol, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone.

12. The method of claim 1, wherein the compound of Formula I reduces or eliminates cardiopathies, selected from QT prolongation, cardiac muscle damage, or AV block, that are drug-induced or caused by a disease or condition.

13. The method of claim 1, wherein the compound is selected from at least one of:

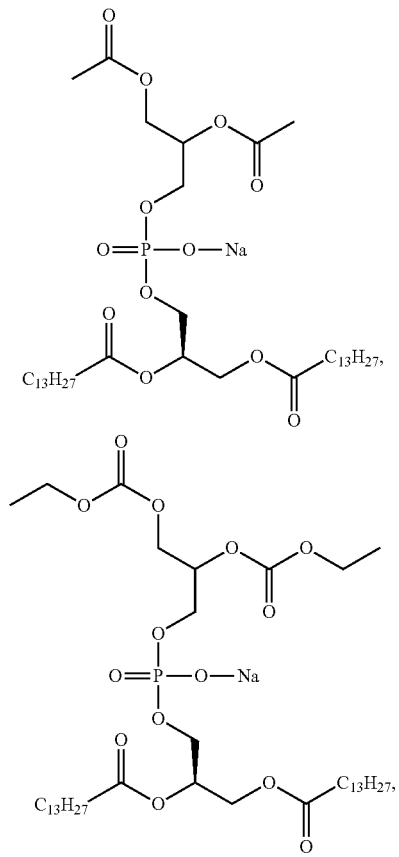

83
-continued
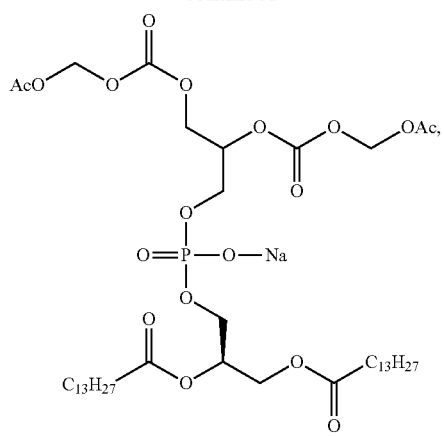
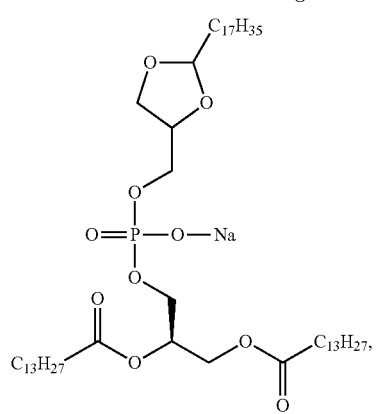
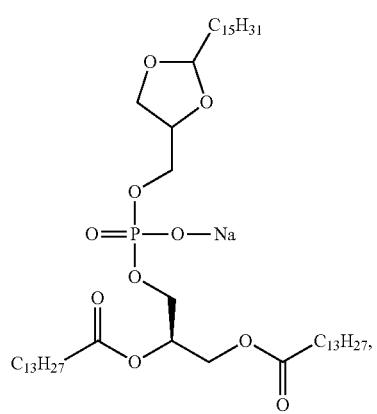
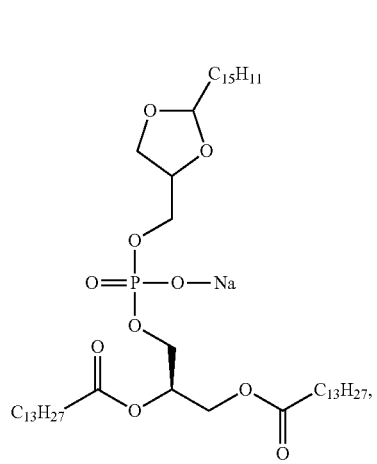
84
-continued
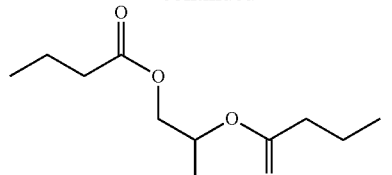
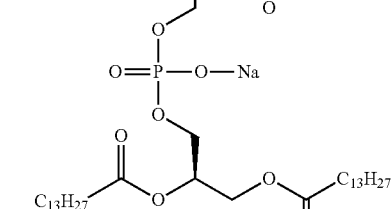
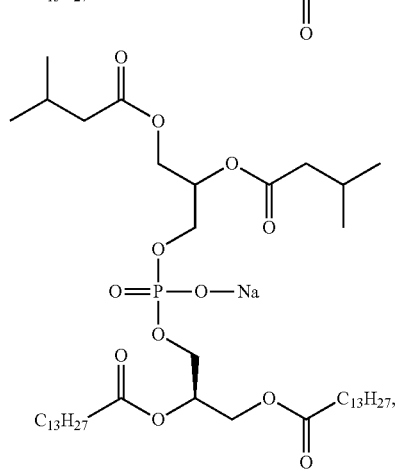
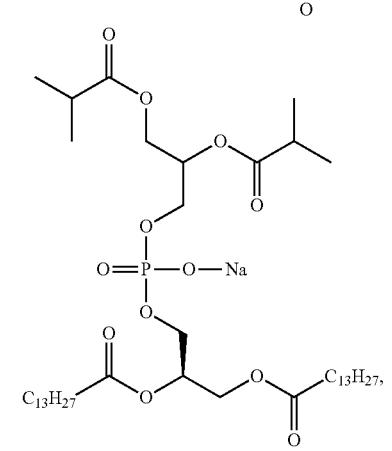
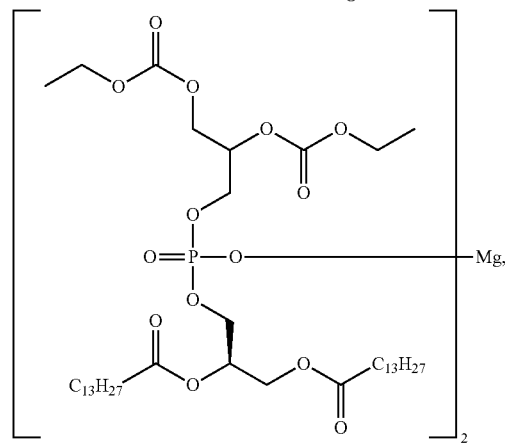

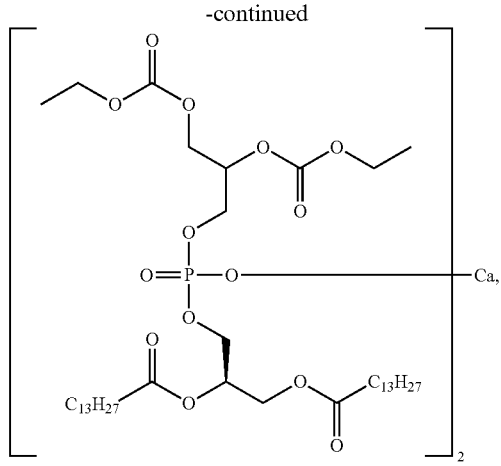
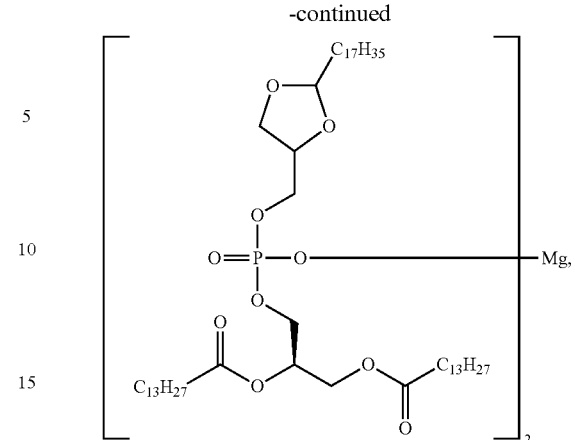
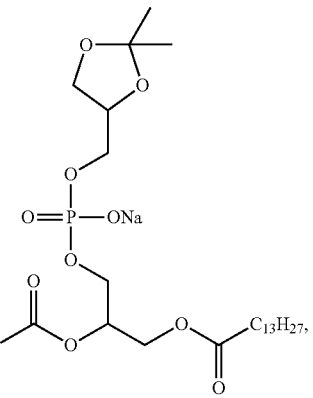
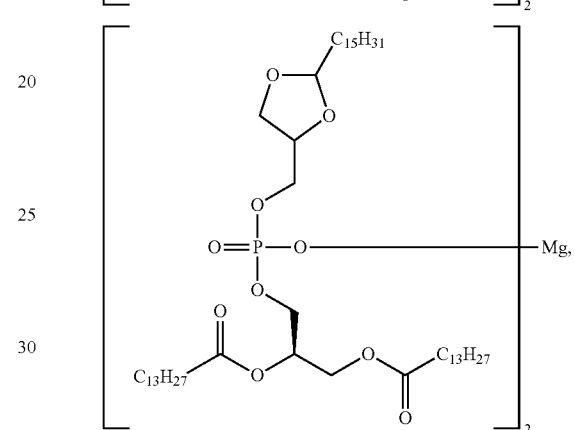
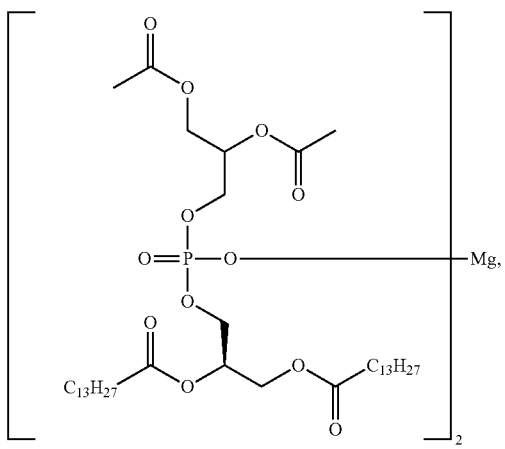
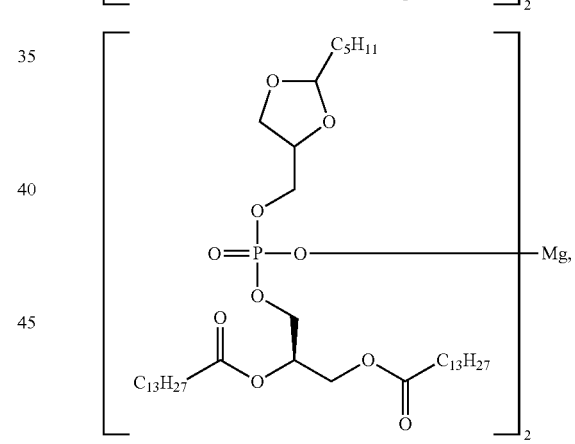
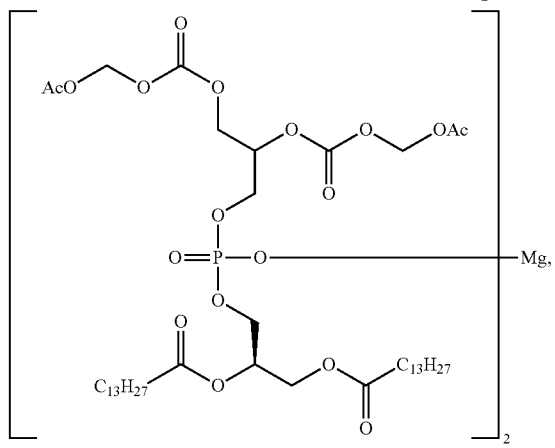
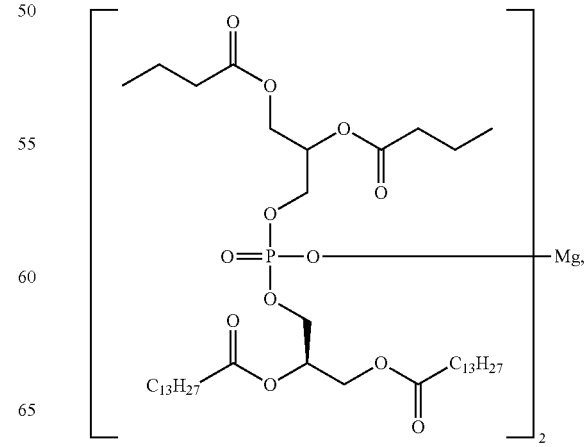

87
-continued
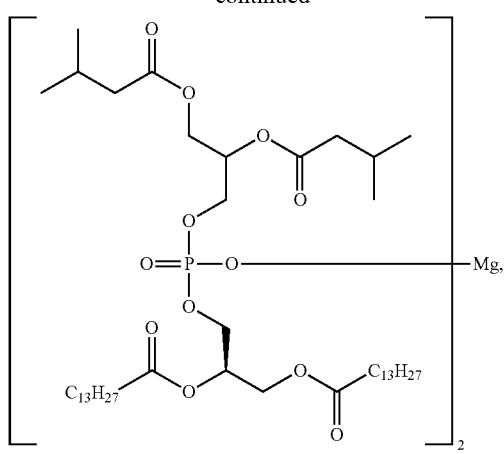
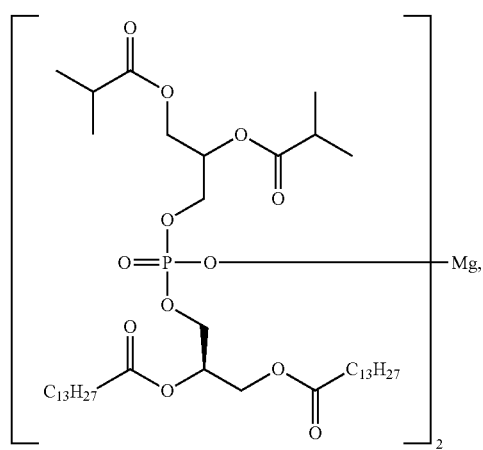
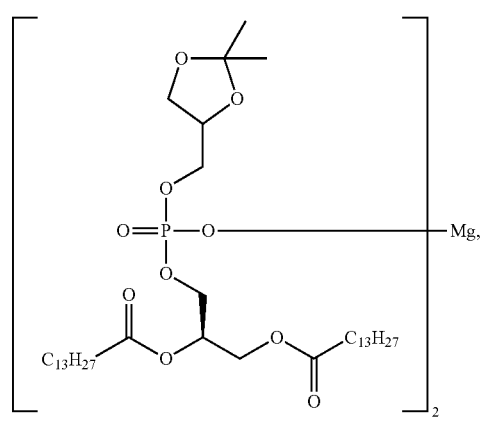
88
-continued
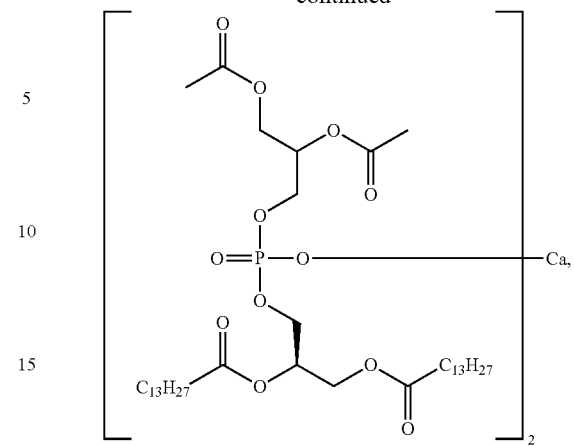
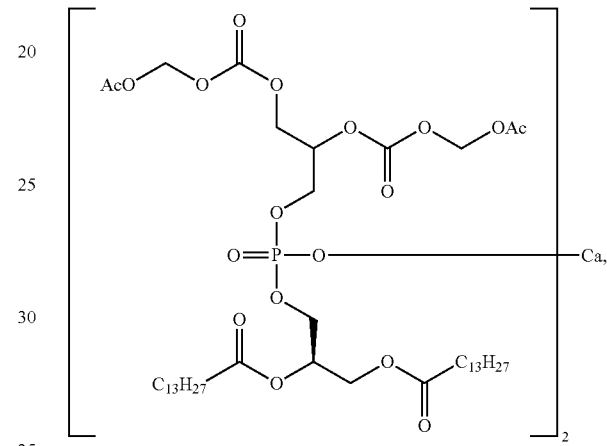
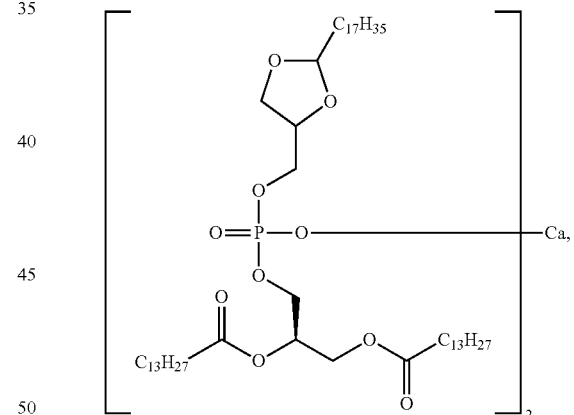
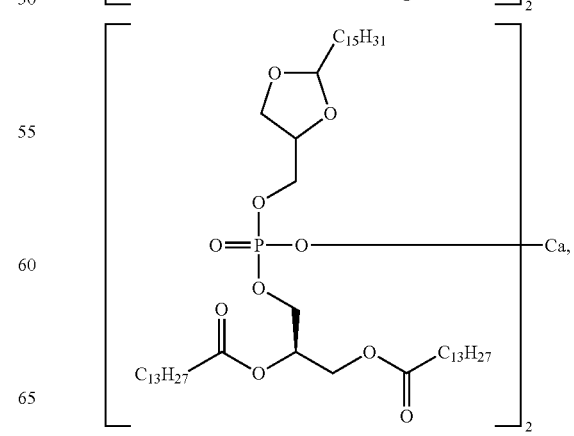

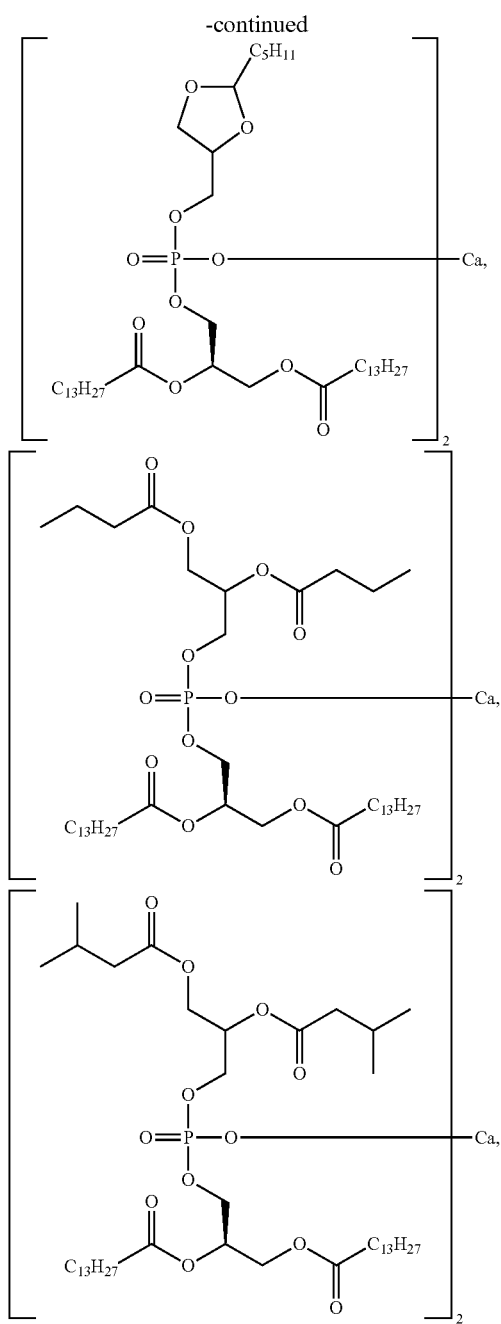
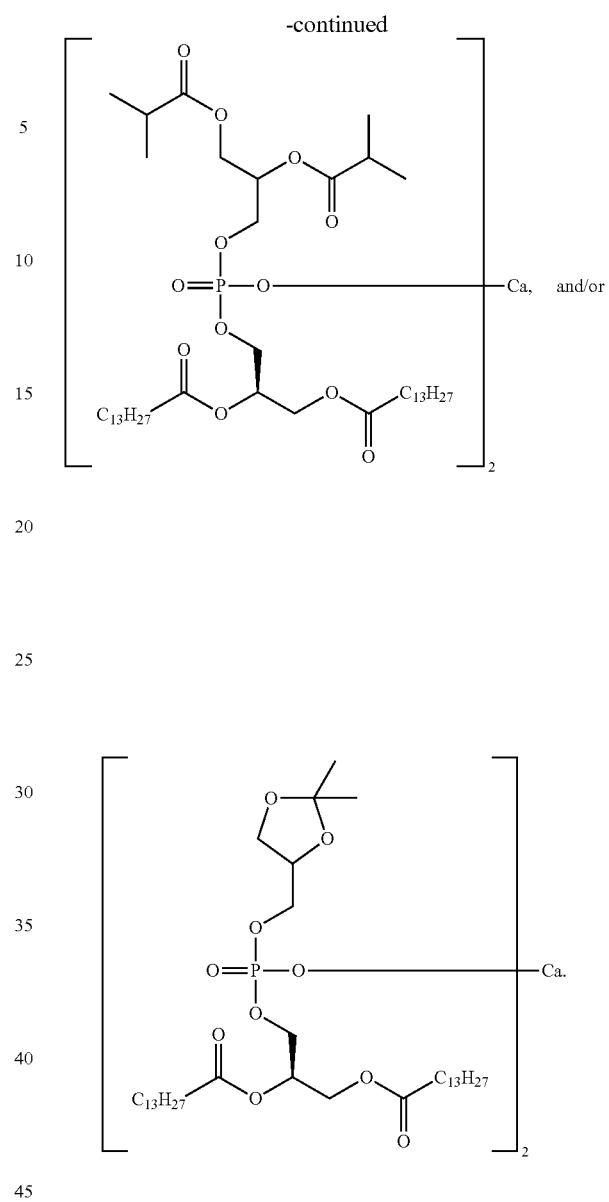
14. The method of claim 1, wherein the method produces compounds that individually exist as a single entity, a solvate, a hydrate, a crystal, an amorphous solid, a liquid, or an oil.
* * * * *